US012642849B2

(12) United States Patent
Tang

(10) Patent No.: US 12,642,849 B2
(45) Date of Patent: Jun. 2, 2026

(54) ALLERGY TREATMENT

(71) Applicant: PROTA THERAPEUTICS PTY LTD, Melbourne (AU)

(72) Inventor: Mimi Lai-Kuan Tang, Parkville (AU)

(73) Assignee: PROTA THERAPEUTICS PTY LTD, Melbourne (AU)

( * ) Notice: Subject to any disclaimer, the term of this patent is extended or adjusted under 35 U.S.C. 154(b) by 0 days.

(21) Appl. No.: 19/302,936

(22) Filed: Aug. 18, 2025

(65) Prior Publication Data

US 2025/0381267 A1    Dec. 18, 2025
US 2026/0130989 A9    May 14, 2026

Related U.S. Application Data

(63) Continuation of application No. 17/787,864, filed as application No. PCT/AU2020/051421 on Dec. 23, 2020.

(30) Foreign Application Priority Data

Dec. 23, 2019    (EP) ..................................... 19219500
Jul. 7, 2020    (AU) ................................ 2020902339

(51) Int. Cl.

| | |
|---|---|
| A61K 39/35 | (2006.01) |
| A61K 9/00 | (2006.01) |
| A61K 35/741 | (2015.01) |
| A61K 35/742 | (2015.01) |
| A61K 35/744 | (2015.01) |
| A61K 35/745 | (2015.01) |
| A61K 35/747 | (2015.01) |
| A61K 36/064 | (2006.01) |
| A61K 39/00 | (2006.01) |
| A61P 37/08 | (2006.01) |

(52) U.S. Cl.
CPC ............ *A61K 39/35* (2013.01); *A61K 9/0053* (2013.01); *A61K 35/741* (2013.01); *A61K 35/742* (2013.01); *A61K 35/744* (2013.01); *A61K 35/745* (2013.01); *A61K 35/747* (2013.01); *A61K 36/064* (2013.01); *A61P 37/08* (2018.01); *A61K 2039/54* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 6,506,380 | B1 | 1/2003 | Isolauri et al. |
| 7,060,687 | B2 | 6/2006 | Hsu et al. |
| 9,402,896 | B2 | 8/2016 | Tang |
| 10,071,157 | B2 | 9/2018 | Tang |
| 10,265,349 | B2 | 4/2019 | Chatila et al. |

| | | | |
|---|---|---|---|
| 2005/0180961 | A1 | 8/2005 | Pecquet et al. |
| 2006/0233772 | A1 | 10/2006 | Herz et al. |
| 2008/0233155 | A1 | 9/2008 | Moingeon et al. |
| 2008/0254058 | A1 | 10/2008 | Glenting et al. |
| 2009/0169582 | A1 | 7/2009 | Chua et al. |
| 2009/0297564 | A1 | 12/2009 | Hernandez et al. |
| 2011/0097361 | A1 | 4/2011 | Tang |
| 2016/0228542 | A1 | 8/2016 | Tang |
| 2019/0070288 | A1 | 3/2019 | Tang |
| 2020/0197515 | A1 | 6/2020 | Tang |

FOREIGN PATENT DOCUMENTS

| | | | |
|---|---|---|---|
| EP | 1364586 | A1 | 11/2003 |
| EP | 1723965 | A1 | 11/2006 |
| EP | 2244734 | B1 | 5/2016 |
| EP | 3097927 | A1 | 11/2016 |
| WO | WO-0137865 | A1 | 5/2001 |
| WO | WO-0166136 | A2 | 9/2001 |
| WO | WO-03099037 | A1 | 12/2003 |
| WO | WO-2006063592 | A1 | 6/2006 |
| WO | WO-2006123230 | A2 | 11/2006 |
| WO | WO-2007123488 | A1 | 11/2007 |
| WO | WO-2009094717 | A2 | 8/2009 |
| WO | WO-2012123759 | A1 | 9/2012 |

OTHER PUBLICATIONS

Schneider et al. A pilot study of omalizumab to facilitate rapid oral desensitization in high-risk peanut-allergic patients.' J Allergy Clin Immunol 2013;132:1368-74.*

Varshney, P. et al. (2011). A Randomized Controlled Study of Peanut Oral Immunotherapy: Clinical Desensitization and Modulation of the Allergic Response, J. Allergy and Clinical Immunology 127(3):654-660.*

Jones, S.M. et al. (Aug. 2009). "Clinical Efficacy and Immune Regulation With Peanut Oral Immunotherapy," J. Allergy Clin. Immunol. 124(2):292-300.*

Hofmann, A.M. et al. (Aug. 2009). "Safety of a Peanut Oral Immunotherapy Protocol in Children With Peanut Allergy," J. Allergy Clin. Immunol. 124:286-291.*

Hsiao, K-C. et al., "Long-term clinical and immunological effects of pro-biotic and peanut oral immunotherapy after treatment cessation: 4-year follow-up of a randomized, double-blind, placebo-controlled trial", The Lancet Child & Adolescent Health. 2017, vol. 1, No. 2, pp. 97-105.

(Continued)

*Primary Examiner* — Nora M Rooney
(74) *Attorney, Agent, or Firm* — Mintz Levin Cohn Ferris Glovsky and Popeo, P.C.

(57) ABSTRACT

The present invention concerns a method of treating peanut allergy in a subject, or a population of subjects, the method comprising administering to said subject or population of subjects a peanut allergen by an oral immunotherapy (OIT) regimen comprising a dose escalation phase in which the peanut allergen is administered in a dose which is increased in increments from an initial dose of the allergen equivalent of 5 mg peanut protein or less to a dose of the allergen equivalent of 200 mg peanut protein or more within 4 to 9 weeks from the administration of the initial dose. The treatment reduces the length of the build-up phase in peanut OIT methods and improves the likelihood or odds of the subject achieving sustained unresponsiveness.

20 Claims, 3 Drawing Sheets

(56) References Cited

OTHER PUBLICATIONS

MacGinnitie, A.J. et al., "Omalizumab facilitates rapid oral desensitization for peanut allergy", The Journal of Allergy and Clinical Immunology. 2017, vol. 139, No. 3, pp. 873-881.

Schneider, L.C. et al., "A pilot study of omalizumab to facilitate rapid oral desensitization in high-risk peanut-allergic patients", The Journal of Allergy and Clinical Immunology. 2013, vol. 132, No. 6, pp. 1368-1374.

Tang, M.L.K. et al., "Administration of a probiotic with peanut oral immunotherapy: A randomized trial", The Journal of Allergy and Clinical Immunology. 2015, vol. 135, No. 3, pp. 737-744.

International Search Report and Written Opinion issued in PCT/AU2020/051421dated Mar. 5, 2021 (8 pages).

Blaiss et al., Current Management and Use of Oral Immunotherapy in the United States for Patients With Peanut Allergy, Allergy and Asthma Proceedings, Oceanside Publications, Inc. 2019: vol. 40, No. 4.: 214-220.

Clark, et al. "Successful Oral Tolerance Induction in Severe Peanut Allergy", vol. Allergy 2009: 64: 1218-1220.

Fujizuka, A. et al. (2011). "Rapid and specific oral immune induction in peanut allergy patients," Allergies 60(9-10):1354, Abstract No. MS22-5).

Ito, N. (2014). "Rapid oral immunotherapy (rush OIT)," Allergies 63(7):961-962.

A Method of Inducing Tolerance to an Allergen, European Patent No. 2244734 B1, Notification Concerning the Date of Oral Proceedings, Mar. 8, 2018, 1 page.

A Method of Inducing Tolerance to an Allergen, European Patent No. 2244734 B1, Patentee's Submissions Opposition by Nestec S.A., May 29, 2018, 1 page.

A Method of Inducing Tolerance to an Allergen, European Patent No. 2244734 B1, Summons to Attend Oral Proceedings, Dec. 13, 2017, 13 pages.

A Method of Inducing Tolerance to an Allergen, European Patent No. 2244734 B1, Communication of a Notice of Opposition mailed Dec. 23, 2016, Notice of Opposition by N.V. Nutricia dated Dec. 14, 2016, 17 pages.

A Method of Inducing Tolerance to an Allergen, European Patent No. 2244734 B1, Patentee's Submissions, Opposition by Nestec S.A, Apr. 19, 2018, 17 pages.

A Method of Inducing Tolerance to an Allergen, European Patent No. 2244734 B1, Communication of a Notice of Opposition mailed Feb. 16, 2017, Notice of Opposition by Nestec S.A. dated Jan. 31, 2017, 20 pages.

A Method of Inducing Tolerance to an Allergen, European Patent No. 2244734 B1, Opponent's Response to Request for Postponement x2, Mar. 5, 2018, 4 pages.

A Method of Inducing Tolerance to an Allergen, European Patent No. 2244734 B1, Patentee's Submissions, Opposition by N.V. Nutricia, Apr. 19, 2018, 5 pages.

A Method of Inducing Tolerance to an Allergen, European Patent No. 2244734 B1, Letter Requesting Postponement of Oral Proceedings, Feb. 27, 2018, 5 pages.

A Method of Inducing Tolerance to an Allergen, European Patent No. 2244734 B1, Patentee Response to Notices of Opposition, Jul. 25, 2017, 52 pages.

A Method of Inducing Tolerance to an Allergen, European Patent No. 2244734 B1, Response to the Preliminary Opinion of the Opposition Division, Apr. 19, 2018, 67 pages.

A Method of Inducing Tolerance to an Allergen, European Patent No. 2244734 B1, Patentee's Submissions, Opposition by Nestec S.A., May 18, 2018, 9 pages.

Appeal Proceedings dated Feb. 8, 2019 in Response to Decision of the Opposition Division dated Sep. 28, 2018, EP Patent No. 2244734; Proprietor: Murdoch Childrens Research Institute; Opponents: N.V. Nutricia and Nestec S.A.; Annex A: correspondence table of claim requests, 1 page.

Appeal Proceedings dated Feb. 8, 2019 in Response to Decision of the Opposition Division dated Sep. 28, 2018, EP Patent No. 2244734; Proprietor: Murdoch Childrens Research Institute; Opponents: N.V. Nutricia and Nestec S.A.; Grounds of Appeal, 41 Pages.

Appeal Proceedings dated Feb. 8, 2019 in Response to Decision of the Opposition Division dated Sep. 28, 2018, EP Patent No. 2244734; Proprietor: Murdoch Childrens Research Institute; Opponents: N.V. Nutricia and Nestec S.A.; Annex C Letter dated Apr. 19, 2018 (response to Summons), 22 pages.

Appeal Proceedings dated Feb. 8, 2019 in Response to Decision of the Opposition Division dated Sep. 28, 2018, EP Patent No. 2244734; Proprietor: Murdoch Childrens Research Institute; Opponents: N.V. Nutricia and Nestec S.A.; Annex D Letter dated May 18, 2018, 3 pages.

Appeal Proceedings dated Feb. 8, 2019 in Response to Decision of the Opposition Division dated Sep. 28, 2018, EP Patent No. 2244734; Proprietor: Murdoch Childrens Research Institute; Opponents: N.V. Nutricia and Nestec S.A.; Annex B Letter dated Jul. 25, 2017 (response to oppositions), 30 pages.

Appeal Proceedings dated Feb. 8, 2019 in Response to Decision of the Opposition Division dated Sep. 28, 2018, EP Patent No. 2244734; Proprietor: Murdoch Childrens Research Institute; Opponents: N.V. Nutricia and Nestec S.A.; Corrected Marked-Up Claim Request—Feb. 2019 to be considered in appeal proceedings, 36 pages.

Appeal Proceedings dated Feb. 8, 2019 in Response to Decision of the Opposition Division dated Sep. 28, 2018, EP Patent No. 2244734; Proprietor: Murdoch Childrens Research Institute; Opponents: N.V. Nutricia and Nestec S.A.; Annex E Letters dated Jul. 25, 2013 and Oct. 22, 2013, 6 pages.

Decision by the Opposition Division at the oral proceedings dated Jun. 19, 2018 revoking European Patent No. 2244734, Proprietor: Murdoch Childrens Research Institute dated Sep. 28, 2018, 166 pages.

Effects of Probiotics on Plasmacytoid Dendritic Cells (pDC), European Patent No. 2244734, Experimental Data in Support of EP 2244734 of Murdoch Childrens Research Institute, accessed Apr. 2018, 4 pages.

Effects of Probiotics on Plasmacytoid Dendritic Cells (pDC), European Patent No. 2244734, Experimental Protocol for Clinical Trial Performed in Support of EP 2244734 of Murdoch Childrens Institute, accessed Apr. 2018, 9 pages.

Extended European Search Report received for European Application No. 09706855.5, mailed on Apr. 19, 2012, 6 pages.

Extended European Search Report received for European Application No. 16167496.5, mailed on Oct. 13, 2016, 10 pages.

International Search Report and Written Opinion received for PCT Application No. PCT/AU2009/000104, mailed on Mar. 6, 2009, 7 pages.

Maternal Supplement to Enhance Immune System of an Infant, European Patent No. 2811845, The Opposition Division Decision at the oral proceedings, Nov. 10, 2017, 26 pages.

Notice of Opposition corresponding to EP2244734 in the name of Murdoch Childrens Research Institute filed on behalf of NV Nutricia dated Dec. 14, 2016, 10 pages.

Notice of Opposition corresponding to EP2244734 in the name of Murdoch Childrens Researcli Institute filed on behalf of Neslec S.A. dated Feb. 3, 2017, 15 pages.

Prosecution History, European Patent Application No. 16167496.5 (3097927): Supplementary Comments dated Jun. 2, 2017 in view of error made in Response dated May 30, 2017 to Search Opinion, 1 page.

Prosecution History, Response Filed May 20, 2014 to Patent Examination Report No. 2 issued Oct. 24, 2013 corresponding to Australian Patent Application No. 2009208390, 14 pages.

Prosecution History, European Patent Application No. 16167496.5 (3097927): Claims 1-11 Clean submitted with Response dated May 30, 2017 to Search Opinion, 2 pages.

Prosecution History, European Patent Application No. 16167496.5 (3097927): Claims 1-12 Clean submitted with Response dated Aug. 1, 2018 to Communication Noting Loss of Rights Pursuant to Rule 112(1) EPC, 2 pages.

(56) References Cited

OTHER PUBLICATIONS

Prosecution History, European Patent Application No. 16167496.5 (3097927): Claims 1-12 marked-up submitted with Response dated Aug. 1, 2018 to Communication Noting Loss of Rights Pursuant to Rule 112(1) EPC, 2 pages.

Prosecution History, European Patent Application No. 16167496.5 (3097927): Response dated Dec. 19, 2018 to EPO Official Letter (Examination Report) dated Nov. 13, 2018, 2 pages.

Prosecution History, Response Filed Sep. 24, 2013 to Patent Examination Report No. 1 issued Jun. 4, 2013 corresponding to Australian Patent Application No. 2009208390, 20 pages.

Prosecution History, European Patent Application No. 16167496.5 (3097927): Claims 1-11 Marked-Up submitted with Response dated May 30, 2017 to Search Opinion, 3 pages.

Prosecution History, Australian Patent Application No. 2009208390: Patent Examination Report No. 2 issued Oct. 24, 2013, 4 pages.

Prosecution History, European Patent Application No. 16167496.5 (3097927): EPO Official Letter (Examination Report) dated Nov. 13, 2018 Communication pursuant to Article 94(3) EPC, 4 pages.

Prosecution History, Notice of Acceptance issued Jul. 3, 2014 in Australian Patent Application No. 2009208390, 5 pages.

Prosecution History, European Patent Application No. 16167496.5 (3097927): Response dated May 30, 2017 to Rule 69 EPC Communication and Search Opinion, 5 pages.

Prosecution History, European Patent Application No. 16167496.5 (3097927): EPO Official Letter (Examination Report) dated Oct. 10, 2017 Communication pursuant to Article 94(3) EPC, 6 pages.

Prosecution History, European Patent Application No. 16167496.5 (3097927): Response dated Aug. 1, 2018 to Communication Noting Loss of Rights Pursuant to Rule 112(1) EPC, 9 pages.

Prosecution History, Australian Patent Application No. 2009208390: Patent Examination Report No. 1 issued Jun. 4, 2013, 4 pages.

Akdis et al. (Jun. 7, 2004) "Immune Responses in Healthy and Allergic Individuals are Characterized by a Fine Balance between Allergen-specific T Regulatory 1 and T Helper 2 Cells", The Journal of Experimental Medicine, 199(11):1567-1575.

Akdis, C.A. et al., "Mechanisms of allergen-specific immunotherapy and immune tolerance to allergens." World Allergy Organization Journal 8.1 (2015): 1-12.

Almeida et al. (2007) "Microbial Population Present in Fermented Beverage 'Cauim' Produced by Brazilian Amerindians", Int. J. Food Microbiol., 120(1-2):146-151.

Anagnostou, K. et al. "Assessing the efficacy of oral immunotherapy for the desensitisation of peanut allergy in children (Stop II): a phase 2 randomised controlled trial." The Lancet 383.9925 (2014): 1297-1304.

Attwood TK. (2000) "The Babel of Bioinformatics", Science, 290(5491):471-473.

Belz G (Jul. 21, 2017) "The Belz Declaration (first) in European Patent No. 2244734", Melbourne Australia, 38 pages.

Belz G (Apr. 16, 2018) "The Belz Declaration (second) in European Patent No. 2244734", Melbourne Australia, 3 pages.

Belz G. (May 18, 2018) "The Belz Declaration (third) in European Patent No. 2244734", Melbourne Australia, 5 pages.

Blumchen et al. (Jul. 2010) "Oral Peanut Immunotherapy in Children with Peanut Anaphylaxis", The Journal of Allergy and Clinical Immunology, 126(1):82-91.

Blumenthal et al. (2004) "Definition of an Allergen (Immunobiology)", Allergens and Allergen Immunotherapy, 3rd edition, 37-51.

Bruzzese et al. (Dec. 1, 2006) "Impact of Prebiotics on Human Health,", Digestive and Liver Disease, 38(2):S283-S287.

Buchanan et al. (2007) "Egg Oral Immunotherapy in Nonanaphylactic Children with Egg Allergy", Journal of Allergy and Clinical Immunology, 119(1):199-205.

Bucker et al. (2006) "Lactic Fermentation of Peanut Milk", Journal of Food Science, 44(5):1534-1538.

Canonica et al. (Mar. 2003) "Noninjection Routes for Immunotherapy", The Journal of Allergy and Clinical Immunology, 111(3):437-448.

Chin et al. (2000) "Immune Response to Orally Consumed Antigens and Probiotic Bacteria", Immunology and Cell Biology, 78(1):55-66.

Christensen et al. (2002) "Lactobacilli Differentially Modulate Expression of Cytokines and Maturation. Surface Markers in Murine Dendritic Cells", The Journal of Immunology, 168(1):171-178.

Ciprandi et al. (2005) "Baciflus Clausii Effects in Children witli Allergic Rhinitis", Allergy, 60(5):702-703.

Colonna, M. et al., "Plasmacytoid dendritic cells in immunity." Nature immunology 5.12 (2004): 1219-1226.

Dejonge et al. (2008) "Lactobacillus casei Shirota does not Decrease the Food Allergic Response to Peanut Extract in Brown Norway Rats", Toxicology, 249:140-145.

Foligne et al. (2007) "Correlation Between in vitro and in vivo Immunomodulatory Properties of Lactic Acid Bacteria", World Journal of Gastroenterology, 13(2):236-243.

Frischmeyer-Guerrerio et al. (Jan. 2011) "Dendritic Cell and T Cell Responses in Children with Food Allergy", Clinical & Experimental Allergy, 41(1):61-71(18 pages).

Garssen J (Apr. 19, 2018) "The Garrsen Declaration in European Patent No. 2244734", 7 pages.

Gilliet et al. (Aug. 2008) "Plasmacytoid Dendritic Cells: Sensing Nucleic Acids in Viral Infection and Autoimmune Diseases", Nature Reviews: Immunology, 8(8):594-606.

Glenting et al. (2007) "Production of Recombinant Peanut Allergen Ara h 2 using Lactococcus lactis", 66(28):1-10, 1-10.

Goubier et al. (Sep. 19, 2008) "Plasmacytoid Dendritic Cells Mediate Oral Tolerance", Immunity, 29(3):464-475.

Ishida et al. (2005) "Effect of Milk Fermented with Lactobacillus acidophilus Strain L-92 on Symptoms of Japanese Cedar Pollen Allergy: A Randomized Placebo-Controlled Trial", Biosci. Biotechnol. Biochem, 69(9):1652-1660.

Isolauri et al. (2000) "Probiotics in the Management of Atopic Eczema", Clin Exp Allergy, 30(11):1604-1610.

Jahnsen et al. (2000) "Experimentally Induced Recruitment of Plasmacytoid (CD123high) Dendritic Cells in Human Nasal Allergy", The Journal of Immunology, 165(7):4062-4068.

Justicia et al. (Feb. 2008) "Higher Evidence for Specific Immunotherapy than Reported in the ARIA Update", The Journal of Allergy and Clinical Immunology119), 121(2): p. 536.

Karlsson et al. (Jun. 21, 2004) "Allergen-Responsive CD4+ CD25+ Regulatory T Cells in Children Who Have Outgrown Cow's Milk Allergy", Journal of Experimental Medicine, 199(12):1679-1688.

Kohler et al. (2007) "Bacterial-Enterocyte Crosstalk: Cellular Mechanisms in Health and Disease", Journal of Pediatric Gastroenterology and Nutrition, Feb. 2003, 36(2):175-185.

Kukkonen et al. (Jan. 2007) "Probiotics and Prebiotic Galacto-oligosaccharides in the Prevention of Allergic Diseases: A randomized, Double-blind, Placebo-controlled Tria", J. Allergy Clin. Immunol., 119(1):192-198.

Latvala et al. (Sep. 28, 2008) "Potentially Probiotic Bacteria Induce Efficient Maturation but Differential Cytokine Production in Human Monocyte-Derived Dendritic Cells", World Journal of Gastroenterology, 14(36):5570-5583.

Lee et al. (2007) "Selection of Anti-Allergic Lactobacillus in Murine Model of Peanut Allergy", Pediatric Allergy and Respiratory Disease, 17(3):260-270.

Maassen et al. (2000) "Strain-Dependent Induction of Cytokine Profiles in the Gut by Orally Administered Lactobacillus Strains", Vaccine, 18(23):2613-2623.

Majamaa et al. (1997) "Probiotics: A novel Approach in the Management of Food Allergy", Journal of Allergy and Clinical Immunology, 99(2):179-185.

Matsuzaki et al. (2000) "Modulating Immune Responses with Probiotic Bacteria", Immunology and Cell Biology, 78(1):67-73.

Medina et al. (2007) "Differential Immunomodulatory Properties of Bifidobacterium Logum Strains: Relevance to Probiotic Selection and Clinical Applications", Clinical and Experimental Immunology, 150(3):531-538.

Menard et al. (2006) "Stimulation of Immunity without Alteration of Oral Tolerance in Mice Fed with Heat-Treated Fermented Infant Formula", Journal of Pediatric Gastroenterology & Nutrition, 43(4):451-458.

(56) References Cited

OTHER PUBLICATIONS

Moro et al. (2006) "A mixture of Prebiotic Oligosaccharides reduces the Incidence of Atopic Dermatitis during the First Six Months of Age", Arch Dis Child, 91(10):814-819.

Mowat et al. (2004) "Oral Tolerance: Overview and Historical Perspectives", Annals of the New York Academy of Sciences, 1029:1-8.

Nash et al. (Jan. 2007) "Oral Peanut Immunotherapy for Peanut Allergic Patients", The Journal of Allergy and Clinical Immunology, S158 Abstracts, No. 622, 1 page.

Nelson et al. (1997) "Treatment of Anaphylactic Sensitivity to Peanuts by Immunotherapy with Injections of Aqueous Peanut Extract", The Journal of Allergy and Clinical Immunology, 99(6):744-751.

Ngo et al., (1994) "Computational Complexity, Protein Structure Prediction, and the Levinthal Paradox", The Protein Folding Problem and Tertiary Structure Prediction, Ed. K. Merz and S. Le Grand. Boston: Birkhauser, 491-495.

Nials et al. (2008) "Mouse Models of Allergic Asthma: Acute and Chronic Allergen Challenge", Disease Models & Mechanisms, 1(4-5):213-220.

Novak et al. (Apr. 7, 2008) "The Immune Privilege of the Oral Mucosa", Trends in Molecular Medicine, 14(5):191-198.

Palisade Group of Clinical Investigators. "AR101 oral immunotherapy for peanut allergy." New England Journal of Medicine 379.21 (2018): 1991-2001.

Pan et al. (2006) "Comparison of Efficacy of a Novel Probiotic from Koji Fermentation (ImmuSoy) with LGG on Peanut Allergy", Journal of Allergy and Clinical Immunology, 117(2):S327 (Abstract).

Passalacqua et al. (2007) "Allergic Rhinitis and its Impact on Asthma update: Allergen Immunotherapy", The Journal of Allergy and Clinical Immunology, 119(4):881-891.

Patriarca et al. (2003) "Oral Desensitizing Treatment in Food Allergy: Clinical and Immunological Results", Alimentary Pharmacology & Therapeutics, 17(3):459-465.

Perez-Machado et al. (2003) "Reduced Transforming Growth Factor-beta1-producing T Cells in the Duodenal Mucosa of Children with Food Allergy", European Journal of Immunology, 33:2307-2315.

Pessi et al. (2000) "Interleukin-10 Generation in Atopic Children Following Oral Lactobacillus rhamnosus GG", Clinical and Experimental Allergy, 30(12):1804-1808.

Prescott et al. (2008) "Supplementation with Lactobacillus rhamnosus or Bifidobacterium lactis Probioticsin Pregnancy increases Cord Blood Interferon-gamma and Breast Milk Transforming Growth Factor-beta and Immunoglobin A Detection", Clinical and Experimental Allergy, 38(10):1606-1614.

Prioult et al. (Sep. 2003) "Effect of Probiotic Bacteria on Induction and Maintenance of Oral Tolerance to B-Lactoglobulin in Gnotobiotic Mice", Clinical and Diagnostic Laboratory Immunology, 10(5):787-792.

Rautava et al. (2002) "Probiotics During Pregnancy and Breast-Feeding Might Confer Immunomodulatory Protection Against Atopic Disease in the Infant", The Journal of Allergy and Clinical Immunology, 109(1):119-121.

Repa et al. (2003) "Mucosal co-application of Lactic acid Bacteria and Allergen induces Counter-regulatory Immune responses in a Murine Model of Birch Pollen Allergy", Vaccine, 22(1):87-95.

Salminen SJ. (Jul. 20, 2017) "The Salminen Declaration in European Patent No. 2244734", Turku Finland, 9 pages.

Schaffner et al. (1986) "Fermentation of Aqueous Plant Seed Extracts by Lactic Acid Bacteria", Appl. Environ. Microbiol., 51(5):1072-1076.

Scurlock et al. (Feb. 2005) "Safety Oral Peanut Immunotherapy for Peanut Allergic Patients", The Journal of Allergy and Clinical Immunology, S246 Abstracts, No. 979, 1 page.

Servin et al. (2003) "Adhesion of Probiotic Strains to the Intestinal Mucosa and Interaction with Pathogens", Best Practice & Research Clinical Gastroenterology, 17(5): 741-754.

Skolnick et al. (2000) "From Genes to Protein Structure and Function: Novel Applications of Computational Approaches in the Genomic Era", Trends in Biotechnology, 18(1):34-39.

Smith et al. (2000) "Oral Tolerance", American Journal of Respiratory and Critical Care Medicine, 162:S175-S178.

Staden et al. (2007) "Specific Oral Tolerance Induction in Food Allergy in Children: Efficacy and Clinical Patterns of Reaction", Allergy, 62(11):1261-1269.

Steinman et al. (2003) "Tolerogenic Dendritic Cells", Annual Review of Immunology, 21:685-711.

Strentebjerg-Olesen, et al. (Dec. 1999) "Type 1 Fimbriation and Phase Switching in a Natural *Escherichia coli* FimB Null Strain, Nissle 1917", Journal of Bacteriology, 181(24):7470-7478.

Sturm et al. (Mar. 2005) "*Escherichia coli* Nissie 1917 Distinctively Modulates T-Cell Cycling and Expansion via Toll-Like Receptor 2 Signaling", Infection and Immunity, 73(3):1452-1465.

Tang M.L. (May 18, 2018) "The Tang Declaration in European Patent No. 2244734", Melbourne Australia, 7 pages.

Vandenheuvel et al., (Jan. 1998) "Functional and Phenotypic Differences of Monocyte-Derived Dendritic Cells from Allergic and NonAllergic Patients,", The Journal of Allergy and Clinical Immunology, 101(1 Pt 1):90-95.

Vickery, B.P. et al., "Sustained unresponsiveness to peanut in subjects who have completed peanut oral immunotherapy." Journal of allergy and clinical immunology 133.2 (2014): 468-475.

Vinderola CG. (Jul. 24, 2017) "The Vinderola Declaration in European Patent No. 2244734", Santa Fe Argentina, 12 pages.

Von Der Weid et al. (Jul. 2001) "Induction by a Lactic Acid Bacterium of a Population of CD4+ T Cells with Low Proliferative Capacity That Produce Transforming Growth Factor beta and Interleukin-10", Clinical and Diagnostic Laboratory Immunology, 8(4):695-701.

Wahn U (Apr. 18, 2018) "The Wahn Declaration in European Patent No. 2244734", Kleinmachnow Germany, 5 pages.

Wallace et al. (2003) "Interactions of Lactic Acid Bacteria with Human Intestinal Epithelial Cells: Effects on Cytokine Production", Journal of Food Protection., 66(3):466-472.

Wood, R.A. "Oral Immunotherapy for Food Allergy." J Investig Allergol Clin Immunol. 2017;27(3):151-159.

Yazdanbakhsh et al. (Apr. 19, 2002) "Allergy, Parasites and the Hygiene Hypothesis", Science's Compass: Review: Immunology, 296 (5567):490-494 (12 pages).

* cited by examiner

A  Cumulative dose taken during buildup

B  Average dose taken each week

Adverse events

Participants who had 4 AE
Participants who had 3 AE
Participants who had 2 AE
Participants who had 1 AE
Participants who had 0 AE

ALLERGY TREATMENT

CROSS-REFERENCE TO RELATED APPLICATIONS

This application is a continuation of U.S. patent application Ser. No. 17/787,864, filed Jun. 21, 2022, which is a U.S. National Phase Application of PCT International Application No. PCT/AU2020/051421, filed Dec. 23, 2020, which is an International Application of and claims the benefit of priority to European Patent Application No. 19219500.6, filed Dec. 23, 2019 and Australian Patent Application No. 2020902339, filed Jul. 7, 2020, each of which is incorporated herein in their entirety for all purposes.

FIELD

The present invention relates to oral immunotherapy dosage regimens for the treatment of peanut allergy. More particularly, the present invention relates to oral immunotherapy regimens for the treatment of peanut allergy which comprise the administration of a peanut allergen to a subject, in which the dose of peanut allergen is increased rapidly during the dose escalation phase. Even more particularly, the present invention relates to oral immunotherapy regimens for the treatment of peanut allergy which comprise the administration of a probiotic and a peanut allergen to a subject, in which the dose of peanut allergen is increased rapidly during the dose escalation phase.

BACKGROUND

A number of approaches have been explored for the treatment of food allergy. These typically involve a course of immunotherapy comprising the regular and gradual exposure of a subject to increasing doses of the allergen to which they are allergic. Treatment outcomes include desensitization and sustained unresponsiveness (SU). Desensitization is defined as a transient increase in the threshold dose required to trigger an allergic reaction. This protection is only able to be maintained if there is continuing regular exposure to the food allergen, such as with continued treatment. Sustained unresponsiveness is defined as the sustained ability to ingest a food allergen in standard serve amounts without reaction that is maintained without the need for continuing regular allergen exposure. This may reflect a state of tolerance, defined as the ability to eat any amount of allergen ad libitum without reaction and without the need for continuing regular allergen exposure. In terms of clinical benefit to the patient, desensitization offers protection against accidental exposure to small amounts of allergen provided the treatment is continued indefinitely, whereas SU offers long-lasting protection without the need for continuing treatment thus allowing the patient to incorporate the allergen into their normal diet.

Sublingual immunotherapy (SLIT) with food allergen(s) has been shown to induce desensitization in a subset of patients with food allergy, but it has limited efficacy and has not been shown to be effective at inducing SU.

Oral immunotherapy (OIT) with food allergen(s) is effective at inducing desensitization in a high proportion of patients but has only been shown to induce SU in a small subset of patients (Wood, JACI; vol. 27(3): 151-159, 2017, Vickery et al., JACI; 133(2): 468-75, 2014).

Typically, OIT with food allergens (i.e. for the treatment of food allergy) involves orally administering regular doses of the food allergen in increasing amounts to food allergic subjects. OIT protocols typically include three phases of treatment-rush, build-up and maintenance. The rush phase generally involves a number of escalating allergen doses (e.g. 6-8 doses) given over one day starting at a very low dose that the subject can tolerate. The build-up phase generally involves administering a daily dose of the food allergen, typically commencing at the highest tolerated dose of the rush phase (or the cumulative tolerated dose in the rush phase if all rush phase doses are tolerated), with increases in the dose every 1-2 weeks. The maintenance phase continues the treatment at the highest dose reached during build-up phase and provides the same dose of the food allergen daily, often for months to years or indefinitely.

Adverse reactions occur commonly during dosing. In particular, there is a high risk of severe allergic reactions during the dose escalation phases, particularly during the build-up phase. For this reason, the rush phase and each dose increase during the build-up phase are typically performed under observation in hospital; although, reactions can also occur to doses taken at home during build-up or maintenance phases.

Studies on peanut OIT have found that adverse events (AE) occur more commonly during the build-up phase, both on the day of dose increase and during home dosing. Severe reactions are rare but do occur. The most limiting side effect is that 10-20% of subjects experience significant gastrointestinal reactions that lead them to discontinue the therapy and failure to complete the build-up phase. Peanut OIT has also been associated with an increased incidence of eosinophilic oesophagitis, an inflammatory intestinal condition, which requires cessation of OIT treatment. Approaches to minimise the likelihood of AE have been explored, including starting the OIT regimen at a very low dose and applying a very gradual schedule of dose increases during the build-up phase or administering the anti-IgE antibody omalizumab (Xolair™) prior to and during OIT. This latter approach, whilst effective in reducing the likelihood of AE, involves subcutaneous injection of the antibody on multiple occasions, which makes it less attractive to patients. It is also costly. Further, studies administering omalizumab prior to and during peanut OIT show increased peanut specific IgE levels in subjects who had received the omalizumab after omalizumab is withdrawn (see Macginnitie et al., (2017) J Allergy Clin Immunol. 139:873-81). Since elevated peanut sIgE levels are indicative of continuing peanut allergy, this suggests that administration of omalizumab together with OIT fails to result in sustained unresponsiveness despite supporting a more rapid dose escalation and desensitisation.

While in this study one of 8 subjects treated with a sham injection rather than omalizumab prior to and during peanut OIT was able to tolerate the rapid rush updosing schedule for peanut OIT (doses of 0.5, 1, 2, 4, 8, 15, 30, 60, 120 and 250 mg peanut protein 30 minutes apart over one day) and then advance through a dose escalation schedule involving an attempted dose increase every week of 375, 500, 625, 750, 1000, 1250, 1625 and 2000 mg peanut protein, reaching the primary endpoint of tolerating 2000 mg peanut protein by 20 weeks, it is probable that this subject did not in fact have clinical peanut allergy at study entry. This is because the criteria for a positive peanut challenge (which was used to confirm peanut allergy at study entry) included the presence of multiple mild (Grade 1) subjective symptoms, which are commonly reported by allergic patients and do not provide objective evidence of current food allergy; for example the single placebo patient may have simply developed a few areas of faint erythema, occasional scratching, occasional sniffing, mild itching of the nose, mild complaint of nausea, which would not in fact confirm clinical allergy. This would also be consistent with the results of other studies of peanut OIT (without adjunctive omalizumab) that reported much longer times e.g. 41 to 44 weeks for patients to reach a final dose of 800 mg to 4000 mg of peanut protein e.g. Anagnostou et al., (2014) Lancet; 383:1297-304. In the Macginnitie study, the very low likelihood of the placebo subjects successfully reaching 2000 mg peanut protein by 20 weeks reinforces the current standard approach to adopt a slow peanut OIT dosing schedule with small incremental dose increases and teaches away from moving to a faster dose escalation approach. It is also possible that this placebo subject resolved their peanut allergy just prior to the study. Spontaneous resolution of peanut allergy occurs in about 20% of peanut allergy sufferers over a lifetime. Additionally, some subjects might pass a challenge because they have a higher threshold but are still allergic.

Schneider et al., (2013) J. Allergy Clin Immunol. 132: 1368-74 describe a further study of omalizumab treatment prior to and during peanut OIT in patients with high levels of peanut-specific IgE who were at risk of developing significant peanut-induced allergic reactions. The Schneider study showed similar results to previous studies, namely that omalizumab treatment prior to and during peanut OIT reduced the number of AEs and allowed the subjects to tolerate rapid updosing with peanut, suggestive of desensitisation. However, elevated levels of peanut IgE were found to persist in subjects on maintenance OIT, suggesting that the peanut-specific allergic response was maintained. Immune tolerance to peanut requires peanut-specific IgE levels to be at non-allergic levels. It appears that omalizumab treatment prior to and during peanut OIT allows fast updosing of peanut allergen to up to 2000 mg with fewer AEs but prolonged OIT at maintenance dose is required to reduce peanut specific IgE levels once omalizumab treatment has stopped.

The standard dose escalation or updosing protocol for peanut OIT in the absence of pre-treatment with omalizumab or similar anti-IgE antibodies therefore provides gradual dose increases and a prolonged build-up phase to minimise adverse reactions. Typically, a number of incremental dose increases are administered on the first day of treatment (rush day) at 20-30 minute intervals and dose increases during the build-up phase are performed every 2 weeks. Smaller incremental increases in dose during the build-up phase and longer duration on each dose (e.g. 2 weeks or longer) are considered to reduce the likelihood of adverse reactions. However, as dose increases are conducted in hospital or at a specialist facility, this results in an increased number of hospital or physician visits, which results in reduced compliance, increased likelihood of treatment withdrawals (a patient failing to complete therapy), and increased costs associated with delivery of treatment. A long dose escalation period (rush and build-up phases), which reduces the likelihood of adverse reactions is also disruptive and costly for patients and families, potentially increasing the likelihood of withdrawal due to inconvenience.

The length of time it takes to reach a selected maximum dose will be affected by both the starting and finishing doses to be achieved. For example, starting from the same dose, it will take less time to reach a dose of 200 or 300 mg peanut protein than to reach 800 mg or 2000 mg peanut protein or higher. For example, dose escalation phases for peanut OIT have been used in which the time taken to reach the maximum dose ranged from 20 weeks to reach 300 mg peanut protein to 44 weeks to reach 4000 mg, e.g. see the PALISADE Study led by Vickery, N Engl. J Med. (2018) November 22; 379(21): 1991-2001.

In any typical OIT regimen, if there is a reaction to a dose which is deemed not acceptable in the study, the dose is either reduced or continued at the same dose for an additional length of time, e.g. additionally two weeks, until the dose is tolerated without reactions, before resuming the prescribed dosing regimen. If adverse reactions occur on the rush day, the build-up phase is commenced at the last tolerated dose on the rush day and remaining rush day doses are incorporated into the build-up phase, which lengthens the time to reach the maintenance dose. Similarly, if a reaction occurs on the day of dose increase during the build-up phase (to the increased dose), the dose is not increased but is continued at the same dose for an additional period, e.g. additional two weeks, before resuming the prescribed dosing regimen. If reactions occur at home, the dose is either reduced or continued for an additional length of time, until the dose is tolerated without reactions, before resuming the prescribed dosing regimen. Therefore, the actual duration of time for a subject to increase from an initial OIT dose to a maximum OIT dose is typically longer than what is described in the proposed OIT schedule.

Using a low maximum dose (e.g. 800 mg or less) may reduce the duration of build-up to minimise inconvenience and expense, however a lower maximum dose is less effective in inducing either desensitization or SU than a higher maximum dose.

It is well known that rapid dose escalation during the build-up phase in OIT regimen is associated with frequent adverse events. Further, the number of adverse events may typically delay the time to reach the maintenance dose. As a consequence, to reduce the likelihood of adverse events during the build-up phase, it is standard in the field to adopt a gradual dose escalation protocol where doses are increased in small increments over a longer time frame, using a slower and more prolonged build-up phase to minimise adverse reactions, such as a time frame of 32 weeks or more.

There exists a need to improve the safety and tolerability of peanut OIT, increase compliance with peanut OIT and reduce treatment costs, whilst maintaining a high maximum dose to achieve higher rates and level of desensitization as well as higher rates of SU, to provide a safe, tolerable and effective treatment for peanut allergy. The ability to reach a high maintenance dose in a reduced time frame without a corresponding increase in adverse events, allows fewer visits to hospital for dose increases and will dramatically improve the feasibility of administering peanut OIT by allowing a high maintenance OIT dose that is effective in achieving desensitization or SU against peanut allergens to be reached in a reduced time frame. It is an aim of a preferred embodiment of the present invention to satisfy at least one of these needs.

SUMMARY

Surprisingly it has now been found that the build-up phase of peanut OIT may be reduced relative to existing known peanut OIT protocols which do not include pre-treatment with anti-IgE antibody, contrary to current teaching. It has been found that it is possible to increase the dose of peanut allergen that is to be administered to a subject having an allergy to peanut allergen at a faster rate than was previously considered possible unless pre-treating with anti-IgE antibody, without increasing the incidence of adverse events or the drop-out rate. The present invention therefore provides a treatment regimen for peanut allergy that can be tolerated and is safe in subjects (particularly children), which allows a faster time to reach maintenance, thereby allowing a higher dose of peanut allergen to be administered to a subject within shorter time periods than is currently considered possible without the administration of costly anti-IgE antibody.

Furthermore, this rapid dose escalation has unexpectedly been found to be associated with an increased likelihood of achieving sustained unresponsiveness in a subject following completion of treatment. Accordingly, this provides an improved oral immunotherapy dosage regimen for the treatment of peanut allergy comprising the administration of a peanut allergen and optionally a probiotic, wherein the treatment comprises a dose escalation phase in which the allergen is to be administered in a dose which is increased from an initial dose at a faster rate than is currently considered possible without pre-treatment with anti-IgE antibody.

In a first aspect the present invention provides a method of treating peanut allergy in a subject, said method comprising administering to said subject a peanut allergen by an oral immunotherapy regimen comprising a dose escalation phase, wherein the peanut allergen is administered in a dose which is increased in increments from an initial dose of the allergen equivalent of 5 mg peanut protein or less to a dose of the allergen equivalent of 200 mg peanut protein or more within 4 to 9 weeks from the administration of the initial dose, and the peanut allergen is administered orally.

In a preferred embodiment the method of the first aspect further comprises administering a probiotic orally at least once every week during the peanut allergen dose escalation phase.

A particularly preferred embodiment is that the subject is aged less than 10 years old, and preferably less than 5 years old and especially between 1 and 5 years old.

Alternatively expressed, the present invention provides a peanut allergen for use in the treatment of peanut allergy in a subject, wherein the treatment comprises an oral immunotherapy regimen comprising a dose escalation phase in which the peanut allergen is to be administered in a dose which is increased in increments from an initial dose of the allergen equivalent of 5 mg peanut protein or less to a dose of the allergen equivalent of 200 mg peanut protein or more within 4 to 9 weeks from the administration of the initial dose, and the peanut allergen is to be administered orally.

A preferred embodiment further comprises a probiotic to be administered orally at least once every week during the peanut allergen dose escalation phase.

Alternatively expressed, the present invention provides the use of a peanut allergen in the manufacture of a medicament for the treatment of peanut allergy in a subject, wherein said medicament is for administration in an oral immunotherapy regimen comprising a dose escalation phase in which the peanut allergen is to be administered in a dose which is increased in increments from an initial dose of the allergen equivalent of 5 mg peanut protein or less to a dose of the allergen equivalent of 200 mg peanut protein or more within 4 to 9 weeks from the administration of the initial dose and the peanut allergen is to be administered orally.

In a preferred embodiment the medicament is for administering to a subject being orally administered a probiotic at least once every week during the peanut allergen dose escalation phase.

In a preferred embodiment the subject has not received an anti-IgE antibody prior to commencing the OIT regimen or during the dose escalation phase.

In a preferred embodiment the method of the first aspect does not comprise administration of an anti-IgE antibody to the subject.

In a preferred embodiment the method of the first aspect does not involve injection.

In a preferred embodiment the method of the first aspect, all therapeutic agents are administered parenterally, preferably orally.

In a preferred embodiment the only therapeutic agent in the method of the first aspect is the peanut allergen and optionally a probiotic.

In one embodiment the treatment is capable of decreasing peanut sIgE levels in the subject from pre-treatment sIgE levels.

In one embodiment peanut sIgE levels in the subject are decreased at the end of the dose escalation phase compared to pre-treatment sIgE levels.

In one embodiment peanut sIgE levels in the subject are decreased at the end of the oral immunotherapy regimen compared to pre-treatment sIgE levels In one embodiment peanut sIgE levels in the subject are decreased from 20 weeks from the administration of the initial dose compared to pre-treatment sIgE levels.

In one embodiment peanut sIgE levels in the subject are decreased from 18 months from the administration of the initial dose compared to pre-treatment sIgE levels.

In one embodiment the decrease in peanut sIgE levels in the subject compared to pre-treatment sIgE levels is up to a 10% decrease, up to a 20% decrease, up to a 30% decrease, up to a 40% decrease, or up to a 50% decrease or more. Preferably the decrease is at least 20% and more preferably 20-50% or more.

In a preferred embodiment the method of treating peanut allergy in a subject consists of administering peanut allergen only or peanut allergen plus probiotic only.

The present invention also provides a probiotic and a peanut allergen as a combined preparation for simultaneous, separate or sequential use in treating peanut allergy in a subject, wherein the treatment comprises an oral immunotherapy regimen as described hereinbefore.

The preferred embodiments described hereinafter in relation to the methods described herein similarly apply to the uses described herein.

The present invention therefore provides a treatment for peanut allergy which allows the rapid escalation of the dose of peanut allergen that is administered to a subject, from a low initial dose.

Surprisingly, it was found that a more rapid dose escalation of OIT without prior or concurrent treatment with anti-IgE antibody, did not lead to an increase in adverse events provided the dose escalation was not too rapid. Further, contrary to studies using prior or concurrent treatment with anti-IgE antibody which led to increased levels of peanut sIgE compared to baseline upon withdrawal of anti-IgE antibody treatment, the rapid updosing schedule of the invention was capable of reducing peanut specific IgE levels in serum. This also contrasts with studies of OIT alone where initial dosing with OIT leads to increase from baseline (pre-treatment levels) in blood peanut sIgE levels. These findings suggest that treatment with both OIT alone and OIT together with a probiotic according to the dose escalation schedule described herein can modulate the underlying peanut specific allergic immune response.

Furthermore, without wishing to be bound by theory, it is believed that the administration of a probiotic allows administration of OIT using a faster dose escalation regimen with reduced adverse effects during the dose escalation phase of an OIT regimen, thereby improving tolerability and safety of a faster dose escalation regimen of OIT, resulting in fewer study withdrawals as well as fewer reactions to treatment.

It is believed that the reduced side effects despite more rapid dose escalation of OIT that is achieved by addition of probiotic relates to induction of tolerogenic dendritic cells by probiotics which in turn inhibits the allergic response to the peanut allergen (that is administered in the OIT treatment). The side effects which may be decreased include gastrointestinal side effects including abdominal pain, vomiting and eosinophilic esophagitis, respiratory symptoms and systemic allergic reactions, such as anaphylaxis.

DETAILED DESCRIPTION

As used herein the terms "treat", "treated", or "treating" refer to both therapeutic treatment and prophylactic or preventative measures, wherein the object is to protect against (partially or wholly) or avoid an increase in (e.g., lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this application, beneficial or desired clinical results include alleviating at least one symptom, or reducing the risk, occurrence or severity of allergic response. In a particular embodiment, it includes desensitizing the subject, achieving sustained unresponsiveness or achieving tolerance to a particular allergen, such as a peanut allergen.

As used herein the term "therapeutic agent" refers to an agent that provides therapeutic treatment and prophylactic or preventative measures, wherein the object is to protect against (partially or wholly) or avoid an increase in (e.g., lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this application, beneficial or desired clinical results include alleviating at least one symptom, or reducing the risk, occurrence or severity of allergic response. In a particular embodiment, it includes desensitizing the subject, achieving sustained unresponsiveness or achieving tolerance to a particular allergen, such as a peanut allergen.

"Desensitization" refers to a transient increase in the amount of allergen a subject may tolerate without reaction (i.e. the reaction threshold) that is lost when immunotherapy or regular allergen exposure is discontinued.

"Sustained unresponsiveness" or "SU" as used herein describes the sustained ability of a subject to tolerate an allergen (e.g. a standard serving amount or complete a diagnostic food challenge to test for presence of allergy) after stopping immunotherapy for a period of at least 2-4 weeks without requiring regular and frequent exposure to the antigen (e.g. as might be required if a subject is merely desensitized to an allergen).

"Tolerance" as used herein, by contrast, refers to the long-lasting (e.g. years) or permanent ability of a subject to ingest any amount of an allergen via the oral route without reaction, which does not require continued allergen exposure to maintain such a state. In certain embodiments, the present invention therefore provides the treatment of an allergy to a peanut allergen which provides sustained unresponsiveness or tolerance, whereas in other embodiments, it may provide desensitization of a subject to a peanut allergen to which they are allergic.

"Allergy" as used herein refers to acquired hypersensitivity to an allergen. Subjects having an allergy to an allergen may be referred to as allergic subjects, and these terms are used interchangeably herein. The invention is concerned solely with peanut allergy. "Peanut allergy" is an adverse response to one or more peanut allergens triggered by an immunological reaction to the allergen(s). A peanut allergy may also be considered an allergy to a peanut allergen. A peanut allergy should be distinguished from non-immune-mediated adverse responses to peanut, such as intolerance and toxin-mediated reactions (e.g. to aflatoxin). Peanut allergy may be IgE-mediated, Non-IgE mediated or mixed IgE/Non-IgE mediated. In a preferred embodiment the peanut allergy is IgE mediated.

The terms "subject," "individual" or "patient" are used interchangeably and as used herein are intended to include human and non-human animals.

As used herein an "oral immunotherapy regimen" refers to the treatment regimen to be used for the treatment of peanut allergy. This treatment regimen comprises the oral administration of immunotherapy over a period of time using a plurality of doses of peanut allergen. The immunotherapy involves the administration of peanut allergen in increasing doses over weeks, months or years with the aim of stimulating the immune system to develop desensitization, sustained unresponsiveness or tolerance with the aim of alleviating an allergic response. The doses of the peanut allergen to be administered are as discussed hereinafter in more detail. The probiotic may also be administered orally during the regimen as discussed hereinafter. As used herein, oral administration refers to administration by mouth, and not sublingual or buccal administration.

The "dose escalation phase" in the oral immunotherapy regimen refers to a period of that regimen during which the dose of peanut allergen is incrementally increased in intervals. This dose escalation phase may include a rush phase and a build-up phase. After the dose escalation phase, the oral immunotherapy regimen may include a maintenance phase. These phases are discussed in more detail hereinafter.

In the method according to the invention, during the dose escalation phase the peanut allergen is to be administered in a dose which is increased in increments from an initial dose of 5 mg or less peanut protein (or allergen equivalent) to 200 mg or more peanut protein (or allergen equivalent) in 4 to 9 weeks. As referred to herein, the initial dose is any dose during the dose escalation phase which is 5 mg or less peanut protein (or allergen equivalent). As discussed hereinafter, the initial dose is the dose used to calculate time frames for the administration of the subsequent increased doses of the allergen in the dose escalation phase. However, this may or may not be the first dose in the dose escalation phase. In a preferred embodiment the initial dose is the first dose of the dose escalation phase and/or the first dose of the oral immunotherapy regimen. However, one or more lower doses of the allergen may be administered to the subject before the recited initial dose is administered. According to such embodiments, the point at which the initial dose is to be administered serves as a suitable point from which to calculate time frames for the administration of the subsequent increased doses of the allergen in the dose escalation phase. Put another way, the initial dose may be considered to be a threshold dose of the allergen, and the elapsed times for the administration of subsequent higher doses of the allergen during a dose escalation phase may be calculated from the point at which this threshold is crossed (i.e. the time from which the recited initial dose is administered). The rapid increase in the dose of peanut allergen to be administered to a subject following the administration of the initial dose of the peanut allergen may form only part of the dose escalation phase (i.e. the total length of the dose escalation phase may be longer than 9 weeks). Thus, the dose escalation phase may comprise further increasing the dose of peanut protein to be administered to a higher level (i.e. higher than 200 mg).

Accordingly, in certain embodiments, the dose escalation phase may be 9, 10, 11, 12, 13, 14, 15, 16, 17, 18, 19, 20, 21, 22, 23, or 24 weeks or less (but more than 4 weeks) if doses higher than 200 mg are to be achieved. The dose escalation phase may also comprise further incremental increases in the dose of the peanut allergen and in certain embodiments, a dose of the peanut allergen equivalent of about 300, 400, 500, 600, 700, 800, 900, 1000, 1100, 1200, 1300, 1400, 1500, 1600, 1700, 1800, 1900 or 2000 mg or more of peanut protein may be administered. (As used herein "about" refers to doses which vary by +10%.)

Thus, according to certain embodiments of the present invention, the dose escalation phase may comprise administering a dose of the allergen equivalent of 200 mg peanut protein or more within 4 to 9 weeks (preferably 8, 7 or 6 weeks or less (but more than 4 weeks), preferably more than 5, 6 or 7 weeks, for example from 4-8, 4-7, 5-9, 5-8, 5-7, 6-9, 6-8, 6-7 or 7-9 weeks) from the administration of the initial dose of the allergen equivalent of 5 mg peanut protein or less, in combination with one or more (in any combination) of:

a) administering a dose of the allergen equivalent of 400 mg peanut protein or more within 11 weeks or less (preferably 10, 9 or 8 weeks or less (but more than 4 weeks), preferably more than 6, 7, 8 or 9 weeks, for example from 6-11, 6-10, 6-9, 7-11, 7-10, 7-9, 8-11, 8-10, 8-9 or 9-11 weeks) from the administration of the initial dose, b) administering a dose of the allergen equivalent of 800 mg peanut protein or more within 13 weeks or less (but more than 4 weeks) (preferably 12, 11 or 10 weeks or less (but more than 4 weeks), preferably more than 8, 9, 10 or 11 weeks, for example from 8-13, 8-12, 8-11, 9-13, 9-12, 9-11, 10-13, 10-12, 10-11 or 11-13 weeks) from the administration of the initial dose, c) administering a dose of the allergen equivalent of 1200 mg peanut protein or more within 16 weeks or less (but more than 4 weeks) (preferably 15, 14 or 13 weeks or less (but more than 4 weeks), preferably more than 11, 12, 13 or 14 weeks, for example from 11-16, 11-15, 11-14, 12-16, 12-15, 12-14, 13-16, 13-15, 13-14 or 14-16 weeks) from the administration of the initial dose, d) administering a dose of the allergen equivalent of 1600 mg peanut protein or more within 20 weeks or less (but more than 4 weeks) (preferably 19, 18 or 17 weeks or less (but more than 4 weeks), preferably more than 14, 15, 16, 17 or 18 weeks, for example from 14-20, 14-19, 14-18, 15-20, 15-19, 15-18, 16-20, 16-19, 16-18, 17-20, 17-19 or 18-20 weeks) from the administration of the initial dose, and/or e) administering a dose of the allergen equivalent of 2000 mg peanut protein or more within 24 weeks or less (but more than 4 weeks) (preferably 23, 22, 21, 20, 19 or 18 weeks or less (but more than 4 weeks), preferably more than 16, 17 or 18, 19, 20, 21 or 22 weeks, for example from 16-24, 16-23, 16-22, 16-21, 16-20, 17-24, 17-23, 17-22, 17-21, 17-20, 18-24, 18-23, 18-22, 18-21, 18-20, 19-24, 19-23, 19-22, 19-21, 20-24, 20-23, 20-22, 21-24, 21-23 or 22-24 weeks) from the administration of the initial dose. As recited above, a) to e) are typically not performed separately, but may occur cumulatively, e.g. any or all of a) to d) may be performed during performance of e).

In an alternative embodiment any combination of a) to e) may be performed (as described above) independently of the step of achieving a dose of the allergen equivalent of 200 mg peanut or more within 4 to 9 weeks from the administration of the initial dose, i.e. this first dose escalation to 200 mg is not necessarily achieved within 4 to 9 weeks from the administration of the initial dose. Thus, for example, if treatment a) is to be used, the use in the treatment of peanut allergy may comprise an oral immunotherapy regimen comprising a dose escalation phase in which the peanut allergen is to be administered in a dose which is increased in increments from an initial dose of the allergen equivalent of 5 mg peanut protein or less, to a dose of the allergen equivalent of 400 mg peanut protein or more within 11 weeks (e.g. 6 to 11 weeks) or less (but more than 4 weeks) from the administration of the initial dose, and the peanut allergen is to be administered orally, and this may not necessarily include reaching a dose of 200 mg within 4 to 9 weeks. Similar considerations apply to treatments b) to e) which may be used alone or in combination. The preferred aspects relating to these embodiments as described herein similarly apply to these aspects of the invention.

In a particular representative embodiment, the peanut allergen dose may be increased in increments to a dose of the allergen equivalent of 800 mg peanut protein or more within 13 weeks or less (but more than 4 weeks) (preferably 12, 11 or 10 weeks or less, or as described above, preferably 8 to 13 weeks) from the administration of the initial dose. In a further representative embodiment, the peanut allergen dose may additionally or alternatively be increased in increments to a dose of the allergen equivalent of 2000 mg peanut protein or more within 24 weeks or less (but more than 4 weeks) (preferably 23, 22, 21, 20, 19 or 18 weeks or less (but more than 4 weeks), or as described above, preferably 16 to 24 weeks) from the administration of the initial dose.

In particular embodiments, the dose escalation phase may comprise administering a dose of the allergen equivalent of 200 mg peanut protein or more within 6-9 weeks (e.g. within 7, 8 or 9 weeks) from the administration of the initial dose of the allergen equivalent of 5 mg peanut protein or less, in combination with one or more (in any combination) of:

a) administering a dose of the allergen equivalent of 400 mg peanut protein or more within 7-11 weeks from the administration of the initial dose, b) administering a dose of the allergen equivalent of 800 mg peanut protein or more within 9-13 weeks from the administration of the initial dose, c) administering a dose of the allergen equivalent of 1200 mg peanut protein or more within 11-16 weeks from the administration of the initial dose, d) administering a dose of the allergen equivalent of 1600 mg peanut protein or more within 14-20 weeks from the administration of the initial dose, and/or e) administering a dose of the allergen equivalent of 2000 mg peanut protein or more within 16-24 weeks, preferably 16-20 weeks from the administration of the initial dose.

As described hereinbefore in alternative embodiments of the invention these treatment steps may be carried out independently of the initial step.

According to particular representative embodiments, between the administration of the initial dose of 5 mg or less and dose of 200 mg or more peanut protein, the dose escalation phase may comprise administering a dose of the allergen equivalent of 25 mg peanut protein or more within 2 weeks or less (preferably 1 week or less) from the administration of the initial dose, a dose of the allergen equivalent of 50 mg peanut protein or more within 5 weeks or less (preferably 2 weeks or less) from the administration of the initial dose, and/or a dose of the allergen equivalent of 100 mg peanut protein or more within 7 weeks or less (preferably 5 weeks or 4 weeks) from the administration of the initial dose.

Doses as referred to herein refer to dose amounts or dose administrations. For example, a dose of 5 mg may be administered on multiple occasions, i.e. multiple administrations. It is clear from the context used whether the dose refers to an amount or administered dose.

The initial dose of the allergen to be administered to a subject is the allergen equivalent of 5 mg peanut protein or less. Thus, in certain embodiments, the initial dose to be administered to a subject may be the allergen equivalent of about 4 mg, 3 mg, 2 mg, 1 mg peanut protein or less, e.g. about 0.9 mg, 0.8 mg, 0.7 mg, 0.6 mg, 0.5 mg, 0.4 mg, 0.3 mg, 0.2 mg or 0.1 mg peanut protein or less. In a particular representative embodiment, the initial dose may be the allergen equivalent of 2 mg peanut protein or less. Preferably the initial dose is at least 0.1, 0.5 or 1 mg peanut protein (or allergen equivalent). In preferred aspects, the initial dose is 0.1 to 5 mg, 0.1 to 3 mg or 0.5 to 5 mg peanut protein (or allergen equivalent), or any other range combining an upper and lower limit for the dose mentioned above. Without wishing to be bound by theory, it is believed that a low initial dose of allergen may be tolerated by the majority of subjects with a peanut allergy and permits the rapid increase in the dose of the allergen that is to be administered to the subject during the dose escalation phase.

During the course of the dose escalation phase, the dose of the allergen to be administered to the subject is increased in increments from the initial dose. As referred to herein the "increments" are the increases in dose during the dose escalation phase. Preferably these increments are regular in nature, e.g. doubling over a specific unit of time (e.g. every 10-18 days, e.g. every 2 weeks). However, periods of rapid increase (in increments) are also contemplated (e.g. a rush phase as discussed hereinafter). In a preferred embodiment the same dose may be administered to the subject over a period of time before the dose is increased, i.e. such that a step-wise dosing increase is achieved in which multiple doses are administered at a common dose amount before an increase is made. This is common in oral immunotherapy regimens. When multiple doses at a common dose amount (e.g. 200 mg) are used, the first administration of that dose amount is used to calculate the time taken to go from the initial dose to that dose amount. (This applies to both the initial dose and subsequent dose amounts, i.e. the first administration of the relevant dose amount is used to calculate the relevant time periods.)

Increasing the dose in increments allows the dose to be increased gradually over time, thereby minimising the risk that subjects suffer an adverse event to the allergen. Without wishing to be bound by theory, it is believed that as a subject is exposed to increasing doses of the peanut allergen to which they are allergic, they are capable of tolerating gradually increasing doses of the allergen. Thus, an increase from a tolerated dose of the allergen is less likely to cause an adverse event during a dose escalation phase. The dose is therefore increased multiple times, or in multiple increments during the course of the dose escalation phase in the specified dosage regimen. As described above, the dose may typically be increased in increments after a period (e.g. 2 weeks) of dosing (administering) at the same dose. Thus, according to certain embodiments, the dose may be increased in increments every 2 weeks or more following a plurality of doses at the same dose (e.g. 5 or more doses at the same dose).

The factor by which the dose of the allergen that is to be administered to the subject is increased between successive doses (administrations or successive increments) may depend on factors such as the frequency of the administration of the allergen, and the frequency with which the dose is to be increased.

Accordingly, in certain embodiments the dose escalation phase may comprise a series of increases in the dose from the initial dose of 5%, 10%, 15%, 20%, 25%, 30%, 40%, 50%, 60%, 70%, 80%, 90% or 100% (or more for each of the preceding percentages, e.g. 5% or more) for each increase. As noted above, the dose (amount) may be held at the same level for a number of doses (administrations) before being increased as described herein.

In a particular representative embodiment, the dose escalation phase may comprise a series of roughly doubling dose increments from the initial dose to higher doses recited herein, and in a particularly preferred embodiment, may comprise a series of roughly doubling dose increments from the initial dose to the dose of 200 mg, 400 mg, 800 mg, 1000 mg and/or 2000 mg of peanut protein (or allergen equivalent) or more, particularly within the indicated preferred timeframes outlined above. As referred to herein "roughly" denotes the measurement or timing of a dose that is not mathematically precise and includes 10% or 20% variance in measurement or timing of a dose. Synonyms for roughly include, but are not limited to, approximately, about or around, which when used herein have the same definition as "roughly". For higher doses, e.g. 800 mg or more, doses may be increased at a slower rate, e.g. at around 25-50% relative to the previous dose (amount), per increment.

The dose (amount) of the allergen may be increased at least monthly, i.e. the dose may be increased every four weeks (e.g. 24-32 days), three weeks (e.g. 17 to 24 days), two weeks (bi-weekly) (e.g. 10 to 18 days) or weekly (e.g. 3-11 days). The dose may alternatively be increased more frequently, e.g. every six days, five days, four days, three days, two days or daily. In other embodiments, the dose of the allergen may be increased multiple times within a single day, i.e. a subject may be administered multiple increasing doses of the allergen within a single day. Thus, the dose of the allergen may be increased every 12 hours, 6 hours, 4 hours, 3 hours, 2 hours, 1 hour, 45 minutes, 30 minutes, 20 minutes, 15 minutes or 10 minutes. The dose of the allergen may be increased at any convenient intervals, and optionally the elapsed time between successive increases in the dose of the allergen may be varied at different points during the dose escalation phase. Thus, by way of representative example, the dose escalation phase may comprise a series of dose increases whereby the dose of the allergen is increased every 30 minutes for up to 12 hours, followed by increases in the dose of the allergen every two weeks (e.g. 10 to 18 days).

In a preferred embodiment, increasing the dose of the allergen in increments may be stepwise, i.e. the dose escalation phase may comprise at least a period of periodically and/or repeatedly administering a particular dose of the allergen to a subject for a period of time, followed by periodically and/or repeatedly administering a higher particular dose of the allergen to the subject for a period of time. In a particularly preferred embodiment, the dose escalation phase may comprise at least a period in which a particular dose of the allergen may be administered to a subject periodically (preferably daily) for a period of at least one week, e.g. up to and including two weeks, (e.g. for four weeks (e.g. 24-32 days), three weeks (e.g. 17 to 24 days), two weeks (bi-weekly) (e.g. 10 to 18 days) or weekly (e.g. 3-11 days)) following which the dose of the allergen may be increased. The dose of the allergen may, therefore, be increased every 1-2 weeks, e.g. in two-weekly increments.

Alternatively, each dose of the allergen that is to be administered to the subject may be a higher dose than the previous dose. Thus, according to such an embodiment, more discrete doses (amounts) of the allergen may be administered to the subject, however, preferably, such an embodiment may comprise increasing each dose (amount) by a smaller increment than the stepwise embodiment referred to above. However, the net effect of increasing the dose of the allergen that is to be administered to the subject in increments is that the particular higher doses of the allergen may be reached within particular time periods, as recited herein.

In a preferred feature, the doses and timing are roughly as set forth in Example 1 and Example 3, provided herein.

According to certain embodiments, the dose escalation phase may comprise a rush phase. A "rush phase" of a dosage regimen refers particularly to a phase in which the dose of the allergen is rapidly escalated in short intervals from an initial dose over a short period of time, typically in a clinical setting such as a hospital or under clinical supervision in the event that a subject suffers from an adverse effect from being administered the allergen. According to a preferred embodiment, the rush phase is at the start of the dose escalation phase, and optionally may comprise the initial dose.

According to a particularly preferred embodiment of the present invention, the rush phase may be completed within 1-7 days (e.g. with the timing discussed hereinbefore), and subjects may be administered doses of the allergen equivalent of roughly 0.1 mg, 0.2 mg, 0.4 mg, 0.8 mg, 1.5 mg, 3 mg, 6 mg and 12 mg peanut protein, wherein preferably the doses are to be administered every 15-30 minutes until the dose of 12 mg is reached. Preferably, such doses may be administered following a single dose of a probiotic.

Thus, in one particular representative embodiment, the dose escalation phase may comprise a rush phase in which the peanut allergen is to be administered in a dose which is increased in increments from the initial dose to a dose of the allergen equivalent of 12 mg peanut protein or more within 1 week or less (e.g. 1 hour to 1 week) from the administration of the initial dose.

In a preferred embodiment the rush phase may be completed in 12 hours or less (e.g. 1 to 12 hours).

In a preferred embodiment the maximum dose of peanut allergen administered in the rush phase is 100 mg or less, more preferably 50 mg or less or 25 mg or less. In a specific 1-day rush phase the maximum dose of peanut allergen administered is 24 mg.

A rush phase may comprise the administration of at least one dose (administration) of probiotic. A rush phase of 1 week or less may comprise the administration of a single dose of probiotic or more than one dose of probiotic. In a rush phase longer than 1 day (e.g. a rush phase of 2 days or more), it may be preferable for two or more doses (administrations) of a probiotic to be administered, e.g. for a dose of probiotic to be administered on each day of a rush phase. Preferably, the rush phase may comprise the administration of the probiotic on a first or only day, i.e. in certain embodiments, the probiotic is to be administered on the first (or only) day of a rush phase. Furthermore, preferably the probiotic may be administered prior to the administration of the allergen in a rush phase or may be administered prior to the administration of the allergen on a day of rush phase. Following the completion of the rush phase, the probiotic may be administered on an at least weekly basis in the remainder of the dose escalation phase and/or maintenance phase as described hereinafter.

Thus, in a preferred embodiment the probiotic is administered at least once during the rush phase and at least once every week thereafter. Administration of the probiotic during the remainder of the dose escalation phase is discussed further hereinafter.

During the dose escalation phase, the timing for administration of the doses (administrations and amount) is selected (based on the above described timings) to take into account the reaction of the subject to which the peanut allergen is administered before any dose increment is performed. Thus, the oral dose (amount) of peanut allergen (e.g. by way of daily administration) may be increased according to the timing above (e.g. after two weeks or less) if the patient has not suffered from repeated adverse allergic reactions, required anti-allergy treatment, suffered from concurrent illness or received a vaccination in the week preceding the proposed increment or experienced other cofactors known to increase the likelihood of adverse reaction to OIT such as an acute exacerbation of asthma or hay fever, menstruation, or exercise within 2-4 hours of a dose of OIT.

Adverse allergic reactions may include acute exacerbation of allergic signs or symptoms.

If the individual has suffered from an adverse allergic reaction, received anti-allergy treatment or suffered from a concurrent illness in the week preceding the proposed dose increment, then the same dose (without increment) may be maintained (e.g. for 2 additional weeks) before further incremental dose increases.

The individual may be monitored for adverse reactions for 2 hours following the administration of each incremental dose increase of allergen. For example, the patient may be assessed prior to administration and parameters such as pulse, blood pressure, peak expiratory flow rate in 1 second and oxygen saturation measured. The increased incremental dose is then administered, and the patient monitored for the development of allergic symptoms and/or changes in any of the measured parameters. Allergic symptoms may be treated with conventional medication as required.

If an individual suffers a severe adverse reaction to the administration of an incremental dose increase of peanut allergen, for example wheezing or other allergic symptoms assessed as serious by a clinician (such as recurrent severe abdominal pain lasting for more than 20 minutes, wheezing, throat tightening, hypotension, collapse and nausea/vomiting or recurrent hives and angioedema, the dose (e.g. daily dose) may be reduced to the previous dose used before the incremental increase. After a further period (e.g. 2 weeks) at the previous dose, the dose may then be increased again to the next incremental dose.

In the dose escalation phase as used herein, the dose of allergen to be administered to the subject is increased over time. The point at which the dose of the allergen to be administered to the subject is no longer increased marks the end of the dose escalation phase. The dose (amount) that is reached at the end of the dose escalation phase may therefore be considered to be the 'final' dose (amount) of the allergen during the dose escalation phase (which does not necessarily equate to the final dose (amount) of the OIT regimen), and the length of the dose escalation phase is the time to reach the final dose (amount) from the administration of the initial dose. Generally, this final dose equates to the maximum dose reached during the dose escalation phase. In determining the timing of the end of the dose escalation phase, if a plurality of doses is administered at the same dose, the final dose corresponds to the first dose administration of the final dose (amount) in the dose escalation phase. Further doses (amounts or administered) of the peanut allergen may be administered to the subject (e.g. in a maintenance phase as described elsewhere herein).

In certain embodiments, the dose escalation phase may be 24 weeks or less, e.g. 22 weeks or less, 20 weeks or less, 18 weeks or less, 16 weeks or less, 14 weeks or less, 12 weeks or less or 10 weeks or less. Preferably the dose escalation phase is or is at least 8, 10, 12, 14, 16, 18 or 20 weeks. Preferably the dose escalation phase is 8 to 24 weeks. It is not excluded, however, that the total length of a dose escalation phase may be longer than e.g. 24 weeks, provided that the dose escalation phase is increased as recited in the treatment of the invention (i.e. such embodiments may comprise an initial rapid increase in the dose of the allergen followed by a more gradual increase). Thus, longer dose escalation phases of 24 weeks or more, e.g. 26 weeks or more, 28 weeks or more, 30 weeks or more, 32 weeks or more, 36 weeks or more, 40 weeks or more, 44 weeks or more, 48 weeks or more or 52 weeks or more are encompassed by the present invention. Similarly, treatments which comprise a dose escalation phase followed by a prolonged period of administration of a particular dose (amount) of an allergen, and a subsequent further dose escalation phase are also encompassed. It is to be understood that the dose escalation phase also includes 1 day of the rush-phase prior to the commencement of build-up phase. For example, a build-up phase of about 9 weeks means 9 weeks and 1 day. Similarly, a build-up phase of about 16 weeks means 16 weeks and 1 day.

The final dose (amount) of the peanut protein in the OIT regimen may depend, to an extent, on the duration of the dose escalation phase, as typically a longer dose escalation phase allows a higher dose of peanut protein to be reached. According to certain embodiments, the final dose (amount) equates to a dosage which is likely to be encountered in normal non-elimination diets such that they may be safely ingested without suffering from an adverse event. According to other embodiments, the final dose may equate to a dosage that protects against accidental exposure to small amounts of peanut protein while remaining on an allergen-elimination diet.

Depending on the rate of incremental dose increase, a shorter dose escalation phase may be associated with a lower final dose than a longer dose escalation phase. Accordingly, by way of a representative example, if the dose escalation phase according to the present invention is 4 to 9 weeks (e.g. 5-9 weeks), a final dose of the allergen equivalent of 200 mg peanut protein or more may be achieved, whereas if the dose escalation phase according to the present invention is 24 weeks or less (e.g. 16-24 weeks), a final dose of the allergen equivalent of 2000 mg peanut protein or more may be achieved.

In certain representative embodiments, following the completion of the dose escalation phase, the treatment of the present invention may comprise a maintenance phase. A "maintenance phase" as used herein refers to the phase in which the dose of immunotherapy (in this case the peanut allergen) is maintained until immunotherapy is discontinued. The maintenance phase is characterised in that the amount of the allergen that is to be administered is at a set dose, i.e. a maintenance dose. In particular representative embodiments, the maintenance dose is about (e.g. +/−10%) the final dose (amount) reached at the end of the dose escalation phase. The final dose, and thus the length of the dose escalation phase, may therefore influence the maintenance dose of the allergen that is to be administered in a maintenance phase following completion of a dose escalation phase. In certain embodiments, if the subject experiences a serious adverse reaction during the maintenance phase, the final dose (amount) or maintenance dose may be decreased to the immediately preceding dose in the build-up phase for a period of time, e.g., about two weeks, and if no further serious adverse reactions occur, the maintenance dose is re-instated at its original dose (amount).

The maintenance dose may be any dose that is effective for the treatment of peanut allergy or allergy to a peanut allergen. Preferably according to the present invention, the maintenance dose is the allergen equivalent of at least 200 mg peanut protein, preferably at least 400 mg or 800 mg, or particularly preferably at least 2000 mg peanut protein. A maintenance dose may be selected from the allergen equivalent of about 200, 300, 400, 500, 600, 700, 800, 900, 1000, 1100, 1200, 1300, 1400, 1500 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100 or 4200 mg peanut protein. Preferred maintenance doses are from 200 mg to 4000 mg, preferably from 800 mg to 2000 mg peanut protein (or allergen equivalent).

The duration of the maintenance phase may be determined by factors such as the outcome that one is aiming to achieve with OIT. For example, whether one is aiming to achieving sustained unresponsiveness or oral tolerance, which allow the subject to discontinue OIT and assume ad libitum intake of allergen in the diet; or desensitization which requires continuing regular exposure to the allergen in order to maintain protection against accidental ingestion of limited amounts of allergen. Studies suggest that a longer overall duration of OIT increases the likelihood of achieving sustained unresponsiveness. Shorter duration of OIT will typically induce desensitization, however only a small subset of treated subjects will achieve sustained unresponsiveness or tolerance. Desensitised subjects must continue with regular peanut allergen exposure, such as with continued OIT treatment or regular ingestion of the peanut allergen, indefinitely to maintain the level of protection that has been achieved.

Typically, in oral immunotherapy regimens of the art, the duration of the maintenance phase is at least 12 months or more, e.g. 18 months, 24 months, 36 months, 48 months or 60 months, as a longer maintenance phase may increase the likelihood of achieving sustained unresponsiveness, and such durations may be used in accordance with the invention. According to certain embodiments of the present invention, the duration of the maintenance phase may be at least 12, 24, 36, 48 or 60 months (up to 5 years) following the completion of the dose escalation phase.

However shorter maintenance phases e.g. of less than 12 months may also be used in certain embodiments and it may be advantageous to reduce the duration of the maintenance phase in conjunction with the shortened dose escalation phase that is the subject of the present invention, in order to dramatically reduce the overall length of treatment. Thus, according to certain embodiments the duration of the maintenance phase may be 24 or 12 months or less, e.g. 48, 44, 40, 36, 32, 30, 28, 26, 24, 22 or 20 weeks or less following the completion of the dose escalation phase, preferably at least 10, 15 or 20 weeks in length. In a further aspect the maintenance phase may be 18, 16, 14, 12, 10, 8, 6 or 4 weeks or less.

Preferably, the maintenance phase is at least 2 weeks in length, e.g. 3, 4, 6, 8, 10, 12, 14, 16, 18, 20, 22, 24, 26, 28, 30, 32, 34, 36, 38, 40, 42, 44, 46, 48, 50 or 52 weeks or more in length. In alternative preferred embodiments, the maintenance phase may be 56, 60, 64, 68, 72, 76, 80, 84, 88, 92, 96, 100 or 104 weeks or more in length.

Upper and lower limits for the range of times for the maintenance phase may be obtained from the values described herein. In particular, the duration of the maintenance phase may preferably be from 2-104 weeks, e.g. 20-104 weeks, more preferably 40-80 weeks, and most preferably 52-68 weeks.

In some embodiments, the maintenance phase occurs over a period of about 5 months to about 5 years. In some embodiments, the maintenance phase comprises orally administering once daily to a subject in need thereof a peanut protein comprising about 200 mg to about 4200 mg of peanut protein or an allergen equivalent thereof and optionally a probiotic, wherein the daily dose of the peanut protein is equal to the last dose achieved during the build-up phase and is maintained over the entire maintenance period. In some embodiments, if the subject experiences an adverse reaction to the peanut protein, the maintenance dose is decreased to the immediate preceding lower incremental dose for a period of time and then increased back to the original maintenance dose. In some embodiments, the maintenance phase follows a build-up phase, which follows a rush phase.

According to one preferred embodiment, the therapy of the present invention may comprise a dose escalation phase comprising a rush phase, and a maintenance phase, wherein in the dose escalation phase the dose of the peanut allergen is increased to at least 2000 mg within 24 weeks or less (e.g. 16-24 weeks), preferably 20 weeks or less (e.g. 16-20 weeks) from the administration of the initial dose, wherein the maintenance dose is about 2000 mg or more, and wherein the maintenance phase is 62 weeks or less (e.g. 10-40 weeks). Preferably according to such an embodiment, the dose of the peanut allergen may be increased from the allergen equivalent of 0.1 mg peanut protein to 12 mg peanut protein in the rush phase consisting of one day or less. In yet further embodiments, the dose of the peanut allergen may be increased roughly every two weeks following the completion of the rush phase until the maintenance dose is reached.

The level of anti-peanut IgE in the serum of the patient or as measured by skin prick test may be assessed before, during or after the oral immunotherapy regimen described herein. Anti-peanut IgE levels in a patient before treatment may be predictive of the amount of desensitization which may occur. For example, low levels of anti-peanut IgE may be indicative that the treatment will be well tolerated and effective in the individual, for example there may be fewer dose alterations due to reactions to OIT (preferably none) and the patient is more likely to tolerate a larger amount of peanut at the end of OIT, if they were to be challenged after the treatment. In some embodiments, the number of incremental dosages required to reach the maximum dose of peanut protein may be reduced for individuals with low initial levels of anti-peanut IgE. Thus, the level of anti-peanut IgE in the serum of the patient or by the skin prick test may be measured in advance of the dose escalation phase, e.g. before commencing the rush phase.

IgE levels may also be measured before, during or after the dose escalation phase and/or before, during or after the maintenance phase of the treatment.

The level of anti-peanut IgE in the blood is a surrogate marker for clinical peanut reactivity and may be indicative of the efficacy of the treatment. Typically, the level of anti-peanut IgE rises initially during OIT treatment and then gradually drops to lower levels. Following the treatment, levels of anti-peanut IgE in the blood may increase or remain unchanged from pre-treatment levels (with desensitisation), reduce from pre-treatment levels (with sustained unresponsiveness) or be abolished (with tolerance).

The administration of the maintenance phase dose during the maintenance phase may be continued until the anti-peanut IgE level in the patient serum or plasma is minimised and the patient is no longer reactive to peanut protein. For example, anti-peanut IgE levels may be reduced to zero, substantially zero, or very low levels. Conveniently, a level of less than 0.35 kU/L in serum is achieved.

Thus, in a preferred embodiment, the level of IgE reactive to specific allergen(s), such as Ara h2, is measured, e.g. in a patient's serum or via the skin prick test, before, during or after the treatment described herein.

In methods of the invention, the sensitivity of the patient to peanut protein may be reduced or abolished following the treatment. For example, the maximum oral dose of peanut allergen which is tolerated by a patient without the onset of allergic symptoms, or the median maximum oral dose of peanut allergen which is tolerated by a population of patients, may be increased by at least 3-fold, 5-fold, 10-fold, 20-fold, 50-fold, at least 500-fold, at least 750-fold or at least 1000-fold after the treatment relative to before the treatment.

Oral immunotherapy regimens require the regular administration of the allergen to a subject with an allergy thereto, in order for the cumulative effects of the therapy to be felt. The peanut allergen is therefore to be administered regularly to the subject during the dose escalation phase, and any maintenance phase, according to the treatment of the present invention. Preferably, the peanut allergen dose is therefore to be administered to the subject at least every 3 days, or more preferably at least every 2 days during the dose escalation and/or maintenance phase. In a yet further preferred embodiment, the peanut allergen is to be administered to the subject every day during the dose escalation phase and/or the maintenance phase, i.e. a daily dose is provided. A "daily" dose as used herein refers to a dose administered every 18 to 30 hours, optionally every 22 to 26 hours, optionally every 24 hours. Patient compliance is greater if the dose is administered at the same time each day, for example on waking, at lunch or before bed.

Irrespective of the frequency of the administration of the allergen, in some embodiments a probiotic is also administered regularly to subjects in the treatments of the present invention. The probiotic is also administered orally. Without wishing to be bound by theory, it is believed that probiotics may colonise the gut of a subject and interact with components of the subject's immune system and/or reduce intestinal inflammation following the administration of the probiotic. In order to ensure that the effects are not transient during the treatment, i.e. to ensure that the beneficial effects of the probiotic are felt by the subject during the course of the treatment of the present invention, regular administration of the probiotic is required. Thus, the treatment of the present invention may require that the probiotic is to be administered to the subject at least weekly (i.e. at least once per week) during the dose escalation phase. Beneficially, the probiotic may also be administered to the subject at least weekly during any maintenance phase. In particular embodiments, the probiotic may be administered to the subject at least once every three days during the dose escalation phase and/or the maintenance phase, and more preferably may be administered at least every two days, or daily.

If administered, it is preferred that the probiotic is to be administered at a dose sufficient to allow safe transit of sufficient probiotic cells through a subject's stomach that their beneficial effects may be felt by the subject. Probiotics are an emerging nutraceutical product, and doses of probiotics which are to be administered to allow probiotics to reach the gut in suitable numbers to provide health benefits to a subject are known and may vary accordingly between probiotics. Suitable doses may be any one of $1\times10^6$, $5\times10^6$, $1\times10^7$, $5\times10^7$ or $1\times10^8$ CFU to any one of $5\times10^8$, $1\times10^9$, $5\times10^9$, $1\times10^{10}$, $2\times10^{10}$, $5\times10^{10}$, $1\times10^{11}$ or $1\times10^{12}$ CFU, for example $1\times10^6$ to $1\times10^{12}$, $5\times10^6$ to $1\times10^{11}$, $1\times10^7$ to $5\times10^{10}$, $1\times10^8$ to $2\times10^{10}$, $1\times10^6$-$1\times10^8$, $1\times10^7$-$1\times10^9$, $1\times10^8$-$1\times10^{10}$, $1\times10^9$-$1\times10^{11}$ or $1\times10^{10}$-$1\times10^{12}$. However, doses of probiotics in the range of $1\times10^8$ CFU to $2\times10^{10}$ CFU are typically advised, and such doses of probiotics may preferably be administered in the treatments of the present invention. Doses within this range may, therefore, be administered at least weekly, or at least every three days, two days, or preferably daily, to subjects in accordance with the treatment of the present invention. In one embodiment the same dose of probiotic is used for every administration. However, in other embodiments the doses may optionally vary, for example the probiotic dose may increase during the course of the treatment, e.g. in line with increases made to the peanut allergen dose.

A "probiotic" as used herein refers to a microorganism that confers a health benefit to a host. In a preferred embodiment, the probiotic to be used is capable of inducing an increased number of tolerogenic dendritic cells, e.g. pDCs, CD103+ DCs or other tolerogenic DCs after in vivo administration. In particular, a probiotic capable of inducing an increased number of pDCs may be used. Such an increased number may result from proliferation, differentiation or increased recruitment to the circulation or the intestine of precursors or tolerogenic DCs (such as pDCs) per se. Preferably the increase results from proliferation or differentiation.

Food allergy is caused by a failure to develop tolerance to a food antigen. Tolerance is an active immune response to a food antigen, which results in the medium- or long-term capacity of the immune system not to develop an adverse reaction to that allergen. Whilst the precise mechanisms that lead to the development of allergy over tolerance are not fully understood, it is believed that factors such as the local immune milieu at the scene of first encounter with a food antigen may play a role, and that this might determine whether tolerance is achieved, or an allergy develops. Dendritic cells are believed to play a central role in determining whether tolerance is achieved, or an allergy develops. Dendritic cells function by processing and presenting antigens to naïve T cells with specificity for the antigen and directing the antigen-specific naïve T cells to differentiate along selective pathways of response. Without wishing to be bound by theory, the subtype of dendritic cell that presents the antigen to the T cell is believed to determine the direction of T cell differentiation. For example, activating DCs can direct the differentiation of naïve T cells into Th2 cells, which in turn lead to development of IgE antibody-producing B cells, mast cells and eosinophils, i.e. the cellular triad involved in allergic inflammation; whereas tolerogenic DCs, such as plasmacytoid DCs (pDCs), will direct the differentiation of naïve T cells into T regulatory cells (Treg), leading to a tolerance response.

Both non-allergic and allergic subjects, have detectable populations of both allergen-specific Th2 cells (that drive the allergic response) as well as allergen-specific Treg cells (that support tolerance); and it is believed that the overall balance of allergen-specific Th2: allergen-specific Treg cells in an individual determines the ensuing clinical phenotype of allergy versus tolerance in that individual. In the allergic subject, there is a predominance of allergen-specific Th2 cells whereas in the non-allergic tolerant subject there is a predominance of allergen-specific Treg cells.

For the majority of subjects, tolerance to foods occurs naturally. On first encounter with the antigen in the intestine, the predominant signal is provided by tolerogenic DCs, including pDCs which are abundant in the intestine and the overall immune response is therefore directed towards tolerance. This initial tolerance response sustains continuing allergen-specific tolerance through the production of immune factors which support continuing involvement of tolerogenic DC leading to further differentiation of allergen-specific naïve T cells into Treg with each subsequent allergen encounter.

In an individual who is allergic to an allergen, the natural process involving tolerogenic DCs has been inappropriately overridden by signals from activating DCs or other activating antigen presenting cells (e.g. Langerhan cells) which instead direct the immune response to allergen towards a Th2 allergic response, resulting in an allergy to that allergen. This initial allergy response sustains continuing allergy to the allergen by production of immune factors which support continuing involvement of activating DC or activating antigen presenting cells leading to further differentiation of allergen-specific naïve T cells into Th2 cells with each subsequent allergen encounter. The predominance of allergen-specific Th2 cells (over allergen-specific Treg cells) results in production of key immune factors central to the manifestation of an allergic reaction, allergen-specific IgE antibodies and mast cells. When the allergic subject is re-exposed to the allergen, the allergen binds to IgE antibodies on the surface of mast cells and cross-linking of adjacent mast cell bound IgE antibodies triggers the release of mediators including histamine and leukotrienes, which lead to the symptoms of an allergic reaction.

Without wishing to be bound by theory it is believed that the addition of probiotics to peanut OIT induces an increase in the number of tolerogenic cells (such as pDCs) and allows a subject to be capable of ingesting higher doses of the peanut allergen during the dose escalation phase without an increase in adverse events. One way this could be achieved is by pDCs supporting the differentiation of allergen-specific Treg cells, which in turn suppress the development of allergic reactions caused by exposure to peanut allergen during OIT. Treg may also inhibit intestinal inflammation, thereby limiting the gastrointestinal symptoms caused by peanut allergen exposure during OIT. Thus, preferably the administration of the probiotic may stimulate the production of tolerogenic DCs, or in other words, an increased number of tolerogenic DCs may be induced by or in response to the probiotic. The induction occurs in vivo but may be tested in vivo or in vitro.

Preferably, the tolerogenic DC is a plasmacytoid dendritic cell (pDC). Data is provided in Example 2 which illustrates that a wide variety of probiotics, including *Lactobacillus rhamnosus* GG, *Bifidobacterium lactis*, *Saccharomyces boulardi, E. coli* Nissle 1917, *Streptococcus thermophilus* and

*Bifidobacterium breve* induce pDCs, and these probiotics represent particularly preferred probiotics for use in the treatments of the present invention. However, many other beneficial intestinal bacteria (probiotics) are expected to induce pDCs and could also be used. The ability to induce pDCs is similar in allergic subjects and subjects with allergic disease (such as asthma, allergic rhinitis, eczema or food allergy, FIG. 5).

Tolerogenic DCs have a half-life of around 14 days. Consequently, if administered, the probiotic must be administered repeatedly throughout the oral immunotherapy regimen to ensure that pDC numbers remain increased and able to direct the differentiation of Treg with specificity for co-administered peanut allergens. Furthermore, probiotics have been shown to only transiently colonise the intestine, usually no longer detectable by 2 weeks after discontinuation of regular administration. As such, the dosing of probiotics as described hereinbefore is used, e.g. oral administration at least once a week.

A procedure for testing probiotics capable of inducing tolerogenic DCs is outlined in Example 2, and representative data demonstrating the induction of tolerogenic DCs by a number of different probiotics is provided. Briefly, a subject may be administered a dose of probiotic daily for two weeks, and PBMCs may be isolated from blood samples taken from a subject before and after administration of the probiotic and cultured in the presence or absence of heat-killed probiotic bacteria, before staining cells for one or more markers known to be associated with tolerogenic DCs and analysing the cultured PBMCs for the proportion of DCs present. According to this procedure, the ability for a probiotic to induce proliferation/differentiation/recruitment of pDC is demonstrated by an increased number of pDC in heat-killed probiotic stimulated cultures at day 14 as compared to day 0. The number of pDCs at each time point is calculated by subtracting the number of pDCs in unstimulated cultures from the number of pDCs in the heat-killed probiotic stimulated cultures. Alternately fresh PBMC's could be used to directly test for pDCs without the need to culture the cells.

In further preferred embodiments, the probiotic may be any probiotic microorganism that is a species of *Lactobacillus, Bifidobacterium, Escherichia, Saccharomyces, Streptococcus* or *Bacillus*. In a particularly preferred aspect the species is from *Lactobacillus, Bifidobacterium, Saccharomyces* or *Streptococcus*.

In one embodiment the probiotic microorganism is a species of *Lactobacillus*, selected from the list of *Lactobacillus acidophilus, Lactobacillus casei, Lactobacillus johnsonii, Lactobacillus lactis, Lactobacillus plantarum, Lactobacillus reuteri, Lactobacillus rhamnosus, Lactobacillus salivarius* and *Lactobacillus helveticus*.

In a particularly preferred embodiment, the probiotic is *Lactobacillus rhamnosus*, and in particular may be *Lactobacillus rhamnosus* GG. In other embodiments, the probiotic may be *Bifidobacterium lactis, Saccharomyces boulardi, E. coli* Nissle 1917, *Streptococcus thermophilus* or *Bifidobacterium breve*.

In some embodiments, the probiotic is a bacterial species selected from the group consisting of *Clostridium bolteae, Anaerotruncus colihominis, Sellimonas intestinales, Clostridium symbiosum, Blautia producta, Dorea longicatena, Erysipelotrichaceae bacterium, Subdolinogranulum* spp. *Ruminococcus torques, Clostridium innocuum, Flavinofractor plautii* and combination thereof.

In some embodiments, the probiotic is a microbial consortium as described in U.S. Pat. No. 10,265,349. In some embodiments, the microbial consortium may be (i) a preparation of a viable, culturable, anaerobic gut bacterial strain (s) that expresses exopolysaccharide, lipoteichoic acid (LTA), lipopolysaccharide (LPS) or other microbial adjuvant molecules that promote the development of regulatory T cells (Treg); (ii) a preparation of a viable, culturable, anaerobic gut bacterial strain(s) that produces butyrate and/or propionate fermentation products via fermentation of carbohydrates and other carbon sources in the gut lumen; (iii) a preparation of one or more viable, culturable, anaerobic gut bacterial strains that alone or in combination performs the full complement of bile acid transformations; (iv) a preparation of a viable, culturable, anaerobic gut bacterial strain that produces compounds capable of stimulating the aryl hydrocarbon receptor (AhR) receptor pathway in gut epithelial cells, antigen presenting cells and/or T cells to stimulate development of regulatory T cell responses; (v) a preparation of a viable, culturable, anaerobic gut bacterial strain(s) that produces compounds capable of stimulating the pregnane X receptor with beneficial effects upon gut barrier function and/or development of regulatory T cell responses; (vi) a preparation of a viable, culturable, anaerobic gut bacterial strain(s) that produces compounds capable of stimulating the RORgamma (RAR-related orphan receptor gamma) pathways to stimulate development of regulatory T cell responses via direct stimulation or RORgamma-activated pathways in gut antigen presenting cells and/or epithelial cells that then stimulate regulatory T cell responses; (vii) a preparation of viable, culturable, anaerobic gut bacterial strain(s) that stimulates host production of mucins and complex glycoconjugates that improve gut barrier function and colonization by protective commensal species; (viii) a preparation of a viable, culturable, anaerobic gut bacterial strain(s) that alters the gut luminal environment to reduce the deleterious activities of dysbiotic species promoting development of unhealthy allergic T cell responses to food antigens; (ix) a preparation of a viable, culturable, anaerobic gut bacterial strain(s) that alters the gut luminal environment to promote improved colonization by other members of the administered consortium for any of the above stated effects, and/or colonization by existing beneficial species in the patients underlying microbiota; (x) a preparation of a viable, culturable, anaerobic gut bacterial strain(s) that promotes the colonization or growth of a bacterial strain in a preparation of (i)-(ix) above, in vivo. In embodiments, the probiotic may be *Eubacterium rectale, Clostridium ramosum, Butyrovibrio crossatus, Roseburia intestinalis, Clostridium hylemonae, Hungatella hathawayi, Clostridium symbiosum, Faecalibacterium prausnitzii, Subdoligranulum variabile, Bacteroides* spp., *Bacteroides thetaiotaomicron, Bacteroides fragilis, Bacteroides ovatus, Parabacteroides goldsteinii, Parabacteroides merdae, Parabacteroides distasonis, Prevotella tannerae, Clostridium sardiniensis, Clostridium hiranonsis, Facealibacterium prausnitzii, Butyrovibrio* spp., *Eubacterium rectale, Roseburia intestinalis, Clostridium scindens, Clostridium* spp (e.g., *Clostridium ramosum, Clostridium scindens, Clostridium hiranonsis, Clostridium bifermentans, Clostridium leptum, Clostridium sardiniensis, Clostridium hathewayi, Clostridium nexile, Clostridium hylemonae, Clostridium glycyrrhizinilyticum, Clostridium lavalense, Clostridium fimetarium, Clostridium symbiosum, Clostridium sporosphaeroides* etc.), *Prevotella copri, Prevotella paludivivens*, and combinations thereof.

Administration of the peanut allergen and probiotic (if administered) is oral, i.e. via the mouth with delivery to the gastrointestinal tract.

In administering the peanut allergen in particular it is anticipated that each increased dose is administered in a clinical setting such as a hospital or under clinical supervision but that intervening daily doses between dose increases may be administered at home. Increasing the dose of the allergen in this way is a common feature of OIT regimens of the art.

The timing of administration of the peanut allergen and/or probiotic has been discussed hereinbefore. When considered relative to one another, if the treatment comprises administration of both the peanut allergen and probiotic, the probiotic and the allergen may be administered separately, sequentially or simultaneously to the subject. Accordingly, in particular embodiments of the present invention, for each administration of the allergen, the probiotic and the allergen may be administered simultaneously, separately or sequentially.

According to preferred embodiments, the probiotic and the allergen may be administered simultaneously in a single composition or as separate compositions.

According to certain embodiments of the present invention, when the probiotic and the allergen are administered in separate compositions and/or when the probiotic and the allergen are administered sequentially, for each administration of peanut allergen, the peanut allergen may be administered one minute, two minutes, three minutes, four minutes, five minutes, ten minutes, 30 minutes, 1 hour, 2 hours, 3 hours, 4 hours, 5 hours, 6 hours, 7 hours, 8 hours, 9 hours, 10 hours, 11 hours or more up to 12 hours before the probiotic. According to alternative embodiments, the probiotic may be administered one minute, two minutes, three minutes, four minutes, five minutes, ten minutes, 30 minutes, 1 hour, 2 hours, 3 hours, 4 hours, 5 hours, 6 hours, 7 hours, 8 hours, 9 hours, 10 hours, 11 hours or more up to 12 hours before the allergen.

According to yet further embodiments of the present invention, the separate and/or sequential administration of the probiotic and the allergen may comprise administering each of the two components separated by greater than 12 hours. Thus, according to certain embodiments, for each administration of the allergen, the allergen and the probiotic may be administered separately up to 7 days apart, more preferably up to 6, 5, 4, 3, 2 or 1 days apart. In certain embodiments, for each administration of peanut allergen, the probiotic may be administered up to 7, 6, 5, 4, 3, 2 or 1 day before the allergen. According to other embodiments, for each administration of the allergen, the allergen may be administered up to 7, 6, 5, 4, 3, 2, or 1 day before the probiotic.

As referred to herein "each" administration of the allergen refers to each dose (administered) of the allergen which is administered to the subject. However, this does not mean that for every dose (administered) of allergen a corresponding dose of probiotic is administered (if the treatment requires administration of peanut allergen and probiotic). Instead each allergen dose is associated with a dose of probiotic and it is to this dose that the discussed administration schedule applies. Thus, for example a single probiotic dose may be the dose associated with two or more allergen administrations providing they are administered within the time constraints discussed herein. In the rush phase, for example, multiple doses of allergen may be administered but only a single dose of probiotic. This is possible because the effects of the probiotic remain for the duration of the multiple allergen doses. Thus, according to certain representative embodiments, a dose or doses of the allergen may be administered separately to or independently from (e.g. after) the probiotic, provided that the probiotic is administered at least weekly to a subject according to the treatment described herein.

The term "allergen" as used herein refers to a substance capable of eliciting an allergic reaction, in particular the production of an antibody against the allergen, typically immunoglobulin E (IgE) but not limited to this, as the allergen may also elicit an allergic reaction that is non-IgE mediated. An immune response where IgE is produced may be referred to as a type I hypersensitivity response or an "IgE mediated allergic reaction" or "IgE mediated allergic response". An allergic response where IgE is not produced or is not the primary cause of symptoms may be referred to as a "non-IgE mediated allergic reaction" or "a mixed IgE/non-IgE mediated allergic reaction".

An "allergic subject" is a subject that, when exposed to an allergen, produces an allergic response. Allergic individuals may vary in the amount of allergen that will cause an allergic reaction and the threshold dose at which an allergic reaction is triggered in an individual is referred to as the reaction eliciting dose. An allergic individual's reaction eliciting dose can vary (by several fold) from time to time depending on various factors related to the host or the environment, such as having an intercurrent illness, asthma exacerbation, allergic rhinitis symptoms or exercising within hours of allergen ingestion but generally does not alter dramatically. In a preferred embodiment, an allergic subject's threshold for reaction to peanut allergen is the allergen equivalent of 50 mg peanut protein or less, preferably 100, 300, 500 or 600 mg or less, in a single dose.

An individual's reaction eliciting dose (threshold for reaction to peanut allergen) may be assessed by performing a food challenge, which involves the oral administration of increasing doses of peanut allergen at regular intervals. The dose at which the individual has an allergic reaction is identified as the reaction eliciting dose for that individual. Thus, for example, the dose of peanut allergen at which a subject experiences an allergic reaction may be assessed by performing food challenge and observing for a reaction within 2 hours of a challenge dose. Typically, a reaction will develop within 15 to 20 minutes of a dose of allergen. Symptoms of a reaction can include hives, swelling, itching, vomiting, abdominal pain, wheeze, stridor, difficulty breathing, pallor/floppiness in an infant or young child, hypotension, collapse. Criteria for confirming a reaction during a food challenge have been set out in the American Academy of Allergy Asthma and Immunology—European Academy of Allergy and Clinical Immunology PRACTALL consensus document.

A peanut allergen is a component of a peanut which acts as an allergen in a subject who has an allergy thereto (i.e. an allergic subject), and upon exposure to a sufficient quantity of peanut allergen, said subject will typically suffer an adverse response thereto. Typically, a peanut allergen is a protein found in peanuts, or more particularly, may be an antigen found within a protein found in peanuts. Yet more particularly, the allergen may be a particular epitope within such a protein. The term "peanut allergen" therefore encompasses any proteinaceous substance which may trigger an allergic reaction in a subject with a peanut allergy. According to particular embodiments of the present invention, the peanut allergen may be, or may be present in or derived from a peanut protein. As referred to herein "derived" allergens are those which are obtained from the peanut protein and are optionally modified but which retain the allergenic epitope.

Reference herein to "a peanut allergen" encompasses one or more peanut allergens, noting that a peanut contains multiple peanut allergens.

The peanut allergen may be a protein (or antigen or epitope) found naturally in peanuts. Thus, conveniently the allergen may be provided as peanut protein, e.g. in the form of peanuts, foods containing peanut such as peanut butter, or more preferably in the form of peanut flour or a defatted or partially defatted form thereof.

Particular peanut proteins are known to be associated with peanut allergy. Put another way, a subject with allergy to peanut may typically be allergic by virtue of an immune reaction to one or more particular proteins which are found in peanut. Without wishing to be bound by theory, such a subject may in particular have high levels of IgE against one or more epitopes present in peanut. According to particular embodiments of the present invention, the peanut allergen may be one or more of Ara h1 to Ara h9. More preferably, the peanut allergen may be one or more of Ara h1, h2, h3, h6, h8 or h9, which are allergens which are believed to be particularly common allergens for subjects suffering from peanut allergy. Yet more preferably, the peanut allergen may be Ara h2. Multiple allergens may be used in the treatment (e.g. by using peanut flour) and the subject may be allergic to one or more of the allergens thus presented.

However, according to further embodiments, the peanut allergen may be derived from a peanut protein e.g. a modified peanut protein (i.e. a modified form of a peanut protein), and thus in certain embodiments, the peanut allergen may be a modified form of a peanut protein, and more particularly may be a modified form of the particular peanut proteins outlined above.

According to particular embodiments, a modified peanut protein may be an engineered peanut protein. Such a protein may be modified relative to a protein found naturally in peanuts but may nevertheless still be an allergen towards which a subject suffering from peanut allergy is allergic, and which may be used in the treatments of the present invention. Thus, according to certain embodiments, an engineered peanut protein may comprise one or more amino acid insertions, deletions and/or substitutions relative to a protein found naturally in peanuts, and/or may be provided in the form of a fusion protein comprising a peanut protein linked to a second polypeptide which is not a peanut protein. Alternatively or additionally, the engineered peanut protein may be a fragment of a peanut protein, i.e. a polypeptide derived from a peanut protein, e.g. those as defined above. According to yet further embodiments, a peanut protein (or a modified form thereof) may be recombinantly expressed in a genetically modified host cell comprising a nucleotide sequence encoding a peanut protein and may preferably be isolated or purified therefrom prior to administration to a subject in the treatment of the present invention.

According to other embodiments, the peanut allergen (more particularly when provided as peanut or a peanut flour as defined herein) may be subjected to one or more processing steps prior to administration to a subject. For example, a peanut allergen may be subjected to one or more enzymatic treatments. Enzymatic treatments with proteases trypsin or elastase have been shown to decrease the allergenicity of certain tree nuts and reduce their IgE-binding capacity and binding to IgE of a soluble peanut fraction is reduced following hydrolysis with the endoprotease alcalase. The peanut allergen may therefore be a partially hydrolysed peanut protein. Alternatively or additionally, the peanut allergen may be subjected to treatment with acid, preferably at below pH 3.0 (e.g. with acetic acid at a pH or ~pH 1.0), and/or may be subjected to heat treatment e.g. by roasting, boiling or frying.

Reference is made herein to doses of the "allergen equivalent" to a particular mass of peanut protein in order to standardise the treatment of the present invention. As referred to herein peanut protein refers to the amount of peanut protein present in the immunotherapy reagent. Peanut protein is the total protein content of a peanut and contains all allergenic peanut proteins, including Ara h1 to h9. The amount of that product to be used in accordance with the invention is determined based on the allergen equivalence, i.e. to provide the same amount of allergen as the allergen present in the stated dose.

When the subject is allergic to more than one peanut allergen, preferably all peanut allergens to which the subject is allergic are administered. In that case, the allergen equivalent to a dose of peanut protein corresponds to a product that contains the same amount of all of the relevant allergens in that dose.

The peanut allergen may be administered in the form of a whole or part peanut, or it may be extracted, isolated and/or purified from a peanut. Preferably, peanut protein may be provided as a peanut extract, such as peanut flour. Preferably the flour is a powder comprising roughly 50% peanut protein and roughly 3.5% moisture.

Peanut flour is produced by crushing, grinding and/or milling whole peanuts. The flour may be partially or completely defatted to reduce the fat content. Defatting does not affect the allergenic peanut protein content of the flour. Peanut flour may be purchased from Byrd Mill (Ashland, VA, USA) or other similar supplier. The peanut flour may be from about 10% to about 15%, or about 12% defatted peanut flour milled from lightly roasted peanuts.

Reference to the equivalent of a dose of a peanut protein therefore includes the amount of peanut protein allergen in a purified or substantially purified or isolated form or when incorporated as part of a substance such as food, a biological system, or chemical composition. Peanuts are widely known to comprise about 25% w/w peanut protein, whereas peanut flour is known to comprise about 50% w/w peanut protein (although the precise values may vary depending on the source of the peanut allergen and factors such as whether the peanut allergen has been processed in any way). The peanut protein content of peanut flour may be readily determined using standard techniques. A dose of peanut allergen of 2000 mg peanut protein may be the equivalent of about 8000 mg peanuts (about eight to ten peanuts).

Other peanut extracts which contain peanut protein may also be used in the methods described herein. In some embodiments, total peanut protein may be isolated and/or purified from other constituents of peanuts for use as described herein.

In some embodiments, peanut protein may be administered as a whole peanut. This may be preferred, for example, for high incremental doses of peanut protein, such as 400 mg and 800 mg or more.

Peanut OIT doses may be prepared by Optima Ovest (Malaga, Australia) under GMP conditions or other similar facility. For example, peanut flour may be provided as set doses within capsules (for doses of 200 mg or less, sachets (doses of 400 mg to 1600 mg) and tubs of peanut flour with standardised measuring scoops (for doses of 200 mg or more).

Conveniently, the peanut allergen (optionally in the form of whole peanuts or a peanut flour as outlined above) may be provided without a carrier or mixed with a carrier in order to provide a composition for administration to a patient. Suitable whole peanuts include any form of roasted peanut, including salted and honey roast, and coated or embedded peanuts, for example peanuts coated or embedded in a food product, such as chocolate or yoghurt. Conveniently crushed nuts may also be used and presented inside a food product, such as a small biscuit, cake, chocolate, sweet or jam, or sprinkled on a yogurt (which according to certain embodiments may not contain a probiotic e.g. *L rhamnosus* GG).

Suitable carriers, when used, act to mask the peanut allergen (particularly when in the form of peanut flour) from the mouth and upper gastrointestinal tract and reduce or prevent swelling and/or irritation in these regions during the treatment. For example, a carrier may contain one or more lipids, carbohydrates or protein constituents. In particular embodiments, the carrier may be a food product (i.e. the peanut allergen may be administered in or on said food product), for example, a dairy or dairy substitute product (e.g. a corresponding soy-based product) such as a yoghurt, milkshake or chocolate, or may be provided in other foods such as apple sauce, or a pudding. For example, the peanut allergen may be provided as a powder or sprinkle for addition to such foods.

Alternatively, the peanut allergen may be provided in a composition for oral delivery such as in a capsule, sachet or tablet, each of which contains a predetermined amount of peanut allergen to provide the correct dose to the patient or subject. Oral delivery compositions may be useful, for example, in avoiding contact between the peanut allergen and the mouth and upper gastrointestinal tract.

Peanut Allergen Compositions

In some embodiments, the peanut allergen or the peanut protein is administered as a pharmaceutical composition. In some embodiments, the pharmaceutical composition comprises peanut flour and other pharmaceutically acceptable carriers. Pharmaceutically acceptable carriers, binders, fillers or diluents, lubricants and preservatives may be used to prepare the oral delivery compositions and are well known in the art. "Pharmaceutically acceptable" as referred to herein refers to ingredients that are compatible with other ingredients of the compositions (or products) as well as physiologically acceptable to the recipient. Pharmaceutical compositions may be used for the treatments described herein.

In some embodiments, the peanut allergen composition comprises peanut flour comprising peanut proteins. In some embodiments, the peanut proteins may be Ara h1, Ara h2, Ara h3, Ara h4, Ara h5, Ara h6, Ara h7, Ara h8, Ara h9, and combinations thereof, or an allergen equivalent thereof.

In some embodiments, the peanut allergen composition comprises peanut protein or an allergen equivalent thereof in an amount from about 0.1 mg to about 2000 mg, about 0.1 mg to about 1500 mg, about 0.1 mg to about 1000 mg, about 0.1 mg to about 500 mg, about 0.1 mg to about 250 mg, about 0.1 mg to about 100 mg, about 0.1 mg to about 50 mg, about 0.1 mg to about 10 mg, or about 0.1 mg to about 2 mg, about 0.1 mg to about 1 mg, about 0.1 mg to about 0.4 mg. Specific examples include about 0.1 mg, about 0.4 mg, about 0.5 mg, about 1 mg, about 2 mg, about 10 mg, about 100 mg, about 500 mg, about 1000 mg, about 2000 mg, and ranges between any of these values.

In some embodiments, the peanut allergen composition comprises peanut flour (having about 50% protein content) in an amount from about 1% to about 70% w/w, about 1% to about 60% w/w, about 1% to about 50% w/w, about 1% to about 40% w/w, about 1% to about 30% w/w, about 1% to about 15% w/w, about 1% to about 10% w/w, about 5% to about 70% w/w, about 8% to about 15% w/w, or about 9% to about 12% w/w.

Probiotic Compositions

If used, in some embodiments, the probiotic microorganism disclosed herein is formulated in a pharmaceutical composition. The composition may comprise pharmaceutically acceptable excipients, such as sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

In some embodiments, the probiotic microorganism is present in the compositions as lyophilized, spray-dried, spore form, or in vegetative form.

In some embodiments, the probiotic composition may further comprise a short chain fatty acid or a derivative thereof, a GPR109A ligand, a GPR43 ligand, a HDAC inhibitor, and combinations thereof.

In some embodiments, the probiotic composition comprises short-chain fatty acid or short-chain fatty acid derivative selected from the group consisting of: butyrate, isobutyrate, propionate, acetate, tributyrin, pivaloyloxymethyl butyrate, and monoacetone glucose 3-butyrate, and combinations thereof.

In some embodiments, the probiotic composition comprises a ligand that bind to GPR109A, a G-protein coupled receptor. Non-limiting examples of GPR109A ligand include pyridine-3-carboxylic acid (also known as niacin or Vitamin B3), a niacin derivative, 4,5-Dihydro-5-methyl-4-oxo-5-phenyl-2-furancarboxylic acid, 5-carboxy-2-methyl-1-oxidopyrazin-1-ium, GSK-256073, GSK256073, ARI-3037MO, INCB019602, INCB19602, MK-0354, MK-0354, a barbituric acid derivative, an anthranilic acid derivative, a pyrazole derivative, an isoxazole derivative, a xanthine derivative, a cycloalkane derivative, a pyrazolopyrimidine, a thyophene, and combinations thereof.

In some embodiments, the probiotic composition comprises a ligand that bind to GPR43, a G-protein coupled receptor. Non-limiting examples of GPR43 ligand include acetate, formate, phenylacetamide 1 [(S)-2-(4-chlorophenyl)-3-methyl-N-(thiazol-2-yl)butanamide], phenylacetamide 2 [(S)-2-(4-chlorophenyl)-N-(5-fluorothiazol-2-yl)-3-methylbutanamide], propionate, valerate, and combinations thereof.

In some embodiments, the probiotic composition comprises HDAC inhibitors selected from trichostatin A, (N-(2-aminophenyl)-N'-phenyl-octanediamide), 2-(4-butoxyphenyl)-N-hydroxyacetamide, MS-275, suberoylanilide hydroxamic acid, RG 2833, and combinations thereof.

In some embodiments, the probiotic composition comprises antigens purified from bacterial strains belonging to *Clostridium* Cluster IV, *Clostridium* Cluster XIVa, or *Clostridium* Cluster XVIII.

The probiotic compositions disclosed herein are formulated to be administered orally in the form of capsules, tablets, pills, sachets, liquids, powders, granules, fine granules, film-coated preparations, pellets, chewables, pastes, syrups, suspensions, elixirs, emulsions, and the like.

In some embodiments, the probiotic composition is formulated for delivery to the intestine. In some embodiments, the probiotic composition is formulated for delivery to the colon.

The probiotic may also be administered by way of a food product, or more preferably may be administered in a drink. The probiotic may therefore preferably be administered in water, cow's milk or soy milk, or other milk or drink. The probiotic may be provided as set doses e.g. within capsules or in a tub with a standardised measuring scoop. *Lactobacillus rhamnosus* GG (LGG) may be obtained from Chr Hansen (Denmark).

Additional agents may be used during the treatment to support the treatment. For example, the probiotic composition may be administered with a prebiotic which is known to support the growth of probiotic organisms. In any of the methods described herein, one or more antibiotics may be administered to the subject prior to administration of any of the probiotic or peanut allergen compositions described herein.

In further embodiments other agents such as anti-allergy drugs, such as antihistamines, steroids, bronchodilators, leukotriene stabilisers and mast cell stabilisers may be used during the treatment. Suitable anti-allergy drugs are well known in the art. Such agents may be useful in reducing allergic inflammation and increasing tolerance of the allergen.

In some embodiments, the administration of the compositions disclosed herein results in the suppression of the production of IgE antibodies. In some embodiments, administration of the compositions described herein results in an increase in the proliferation and/or accumulation of regulatory T cells (e.g. total Tregs or allergen-specific Tregs) in the subject. In some embodiments, administration of the compositions described herein results in an increase in the proliferation and/or accumulation of regulatory T cells (e.g. total Tregs or allergen-specific Tregs) at a particular site (e.g. the gastrointestinal tract) in the subject. In some embodiments, administration of the compositions described herein results in an increase in activity of regulatory T cells.

In some embodiments, administration of the compositions described herein results in an increase the proliferation and/or accumulation of regulatory T cells (e.g. total Tregs or allergen-specific Tregs) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, or more, as compared to the quantity of regulatory T cells in the subject (or particular site in the subject) prior to administration of the compositions.

In some embodiments, the compositions and methods described herein suppress one or more Th2 immune responses. In some embodiments, the compositions and methods described herein suppress the development or differentiation of Th2 cells (also referred to as type 2 helper T cells). In some embodiments, the compositions and methods described herein suppress the activity of Th2 cells. As will be evident by one of ordinary skill in the art, Th2 cells are a subject of CD4+ cells that produce IL-4, IL-5, IL-6, IL-10, and/or IL-13 and may be involved in promoting IgE antibody responses and/or eosinophil activity.

The subject referred to herein refers to an animal, particularly a mammal and more particularly a human with an allergy to an allergen, who can benefit from the treatments of the present invention. In a particularly preferred embodiment, the subject may be an adult. However preferably, the subject is not an adult, and in certain embodiments the subject may be under 18 years old, i.e. the subject may be a child. Yet more preferably, the subject may be a child under 12 years old, or may be a child under 6 years old. In a yet further embodiment, the subject may be from 6 years old, e.g. to 12 years old or 18 years old, and in another embodiment may be from 5 years old to 10 years old. In a particularly preferred embodiment, the child may be from 1 month to 10 years old or 12 years old. In an especially preferred embodiment, the child is less than 10 years old, less than 5 years old, or from 1 year old to 5 years old.

The methods described herein may be used for any patient with peanut allergy and are independent of the patient's sensitivity or challenge threshold to allergen, the weight or height of the patient and other factors.

In the course of making the present invention, it was unexpectedly observed that not only was it possible to increase the dose of the peanut allergen more quickly than has previously been described in the art, and to reduce the time required to achieve a maintenance dose in an oral immunotherapy regimen without an increase in side effects, but that the reduction in the length of time required to reach the same maintenance dose was found to improve the odds of subjects achieving sustained unresponsiveness. In particular, for every one-week reduction in the time to reach the maintenance dose compared to an oral immunotherapy regimen using a longer dose escalation phase, it was found that the odds of achieving sustained unresponsiveness was increased by about 9-11%. Thus, according to particular embodiments, the ability to reach the maintenance phase in a reduced length of time compared to an immunotherapy regimen using a longer dose escalation phase improves the odds of achieving sustained unresponsiveness.

Alternatively expressed, the reduction in time to reach the maintenance dose compared to the time taken to reach the maintenance dose in an oral immunotherapy regimen using a longer dose escalation phase to reach the same maintenance dose improves the odds of the subject achieving sustained unresponsiveness. In particular, reaching the maintenance dose in 24 weeks or less, or more particularly in 23, 22, 21 or 20 weeks or less improves the odds of the subject achieving sustained unresponsiveness compared to oral immunotherapy regimens using a longer dose escalation phase to reach the same maintenance dose.

As referred to herein the "odds of achieving sustained unresponsiveness" provides an indication of the probability that a subject will achieve sustained unresponsiveness as a result of the treatment of the invention. For each subject undertaking the treatment (or treatments of the prior art), their odds of achieving sustained unresponsiveness can be determined based on data generated from a population of individuals which undergo the treatment to which the new subject is to be subjected. The data allows the determination of the proportion of individuals within the population achieving sustained unresponsiveness and hence the probability that any new subject might have of achieving sustained unresponsiveness. Preferably for each week that the dose escalation phase is reduced (e.g. from 26 to 24 or from 32 to 24 weeks), the odds of sustained unresponsiveness is increased by at least 5%, preferably by 5-10%, and more preferably by about 7.5% for each week reduction.

The treatment of the present invention, in which the dose of peanut allergen is increased more quickly than in known methods, is associated with the surprising effect that the rate of adverse events suffered by the subjects during the oral immunotherapy regimen of the invention is comparable to (or lower than) the rate of adverse events in an oral immunotherapy regimen comprising the administration of a peanut allergen OIT alone or probiotic and a peanut allergen using a longer dose escalation phase and a longer time to reach a maintenance phase. This therefore provides the benefit that no more (or fewer) subjects being administered the therapy of the present invention suffer an adverse event during the build-up phase even though the allergen dose is increased more rapidly in treatments of the invention. Oral immunotherapy regimens typically require the increase in the dose of the allergen to be delayed (i.e. for a particular dose to be administered for a longer period of time) in the event that an adverse event is observed. As the treatment does not elicit any more adverse effects than known methods, the treatment can be readily conducted according to the protocols described hereinbefore.

In further embodiments of the invention, the treatment may be applied to a population of subjects. As described herein a population may be at least 5 individuals, e.g. at least 10 or 20 individuals, e.g. from 5-20 individuals.

Thus, according to a further aspect, the present invention provides a peanut allergen for use in the treatment of peanut allergy in a population of subjects, wherein the treatment comprises an oral immunotherapy regimen comprising a dose escalation phase in which the peanut allergen is to be administered in a dose which is increased in increments from an initial dose of the allergen equivalent of 5 mg peanut protein or less to a dose of the allergen equivalent of 200 mg peanut protein or more within 4 to 9 weeks from the administration of the initial dose, and the peanut allergen is to be administered orally, and wherein the treatment is to be administered to a population of subjects.

In a preferred embodiment a probiotic is provided to be administered orally at least once every week during the peanut allergen dose escalation phase.

In preferred aspects, the probiotic, peanut allergen, subject and/or oral immunotherapy regimen is as defined hereinbefore.

Preferably in said population said dose escalation from the allergen equivalent of 5 mg peanut protein or less to the allergen equivalent of 200 mg peanut protein or more is achieved within 4 to 9 weeks from the administration of the initial dose in more than 25% (e.g. more than 30, 40, 50, 60, 70, 75, 80, 85, 90 or 95%, such as from 50-75%) of the population. Preferably the same % of the population achieves the other stated doses (as described hereinbefore, including preferred doses) at the stated time intervals (as described hereinbefore, including preferred times).

In the alternative, preferably the median time of the population to achieve said dose escalation from the allergen equivalent of 5 mg peanut protein or less to the allergen equivalent of 200 mg peanut protein or more is 4 to 9 weeks from the administration of the initial dose. Preferably the median of other times (as described herein, including preferred times) is achieved by the population for the other stated doses (as described hereinbefore).

Disclosed herein is an improved oral immunotherapy regimen for treating peanut allergy in a subject in need thereof that comprises a reduced time frame of the build-up phase when compared to prior art after the surprising discovery that a shorter build-up phase may result in an increased likelihood of sustained unresponsiveness, no increased likelihood of adverse events, particularly moderate to severe adverse events, or a combination thereof.

The build-up phase in the prior art is considerably slower/longer than the present invention. An exemplary prior art build-up phase for peanut plus probiotic OIT is described in Tang et al., J Allergy Clin Immunol 135(3): 737-744, 2015 and shown below:

TABLE 1

| Peanut and probiotic OIT build-up phase-prior art-PPOIT1) | | |
| --- | --- | --- |
| Dose | Period of Dosing during Build-Up Phase (following Rush Phase) | Once Daily Peanut Protein Dose |
| 9 | Day 1 | 24 mg |
| 10 | Weeks 1-2 | 25 mg |
| 11 | Weeks 3-4 | 50 mg |
| 12 | Weeks 5-6 | 75 mg |
| 13 | Weeks 7-8 | 100 mg |
| 14 | Weeks 9-10 | 125 mg |
| 15 | Weeks 11-12 | 150 mg |
| 16 | Weeks 13-14 | 200 mg |
| 17 | Weeks 15-16 | 260 mg |
| 18 | Weeks 17-18 | 330 mg |
| 19 | Weeks 19-20 | 425 mg |
| 20 | Weeks 21-22 | 550 mg |
| 21 | Weeks 23-24 | 715 mg |
| 22 | Weeks 25-26 | 925 mg |
| 23 | Weeks 27-28 | 1.2 g |
| 24 | Weeks 29-30 | 1.55 g |
| 25 | Weeks 31-32 | 2.0 g |

During the build-up phase, the peanut protein is orally administered once daily to a subject in need thereof starting at about 24 mg on day 1, and then is increased the following day to 25 mg and every two weeks thereafter as shown in Table 1 until a maintenance dose is reached.

An additional example of a prior art build-up phase without probiotic is found in the PALISADE study (Vickery 2018 NEJM, supra.) in which the build-up phase of the OIT treatment was over 26 weeks to reach a dose of 300 mg.

In contrast, the embodiments of the present invention are directed to a method of treating a peanut allergy in a subject in need thereof, wherein the method utilizes a build-up phase of about 9 weeks to about 24 weeks, preferably about 16 weeks as shown below, reaching a dose of 2000 mg:

TABLE 2

| Peanut OIT protocol build-up phase-invention-PPOIT2 and PPOIT3 | | |
| --- | --- | --- |
| Dose | Period of Dosing during Build-Up Phase (immediately following Rush Phase) | Once Daily Peanut Protein Dose |
| 9 | Day 1 | About 25 mg |
| 10 | Weeks 1-2 | About 50 mg |
| 11 | Weeks 3-4 | About 100 mg |
| 12 | Weeks 5-6 | About 200 mg |
| 13 | Weeks 7-8 | About 400 mg |
| 14 | Weeks 9-10 | About 800 mg |
| 15 | Weeks 11-12 | About 1.2 g |
| 16 | Weeks 13-14 | About 1.6 g |
| 17 | Weeks 15-16 | About 2.0 g |

As used herein, the term "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. In embodiments or claims where the term comprising is used as the transition phrase, such embodiments can also be envisioned with replacement of the term "comprising" with the terms "consisting of" or "consisting essentially of."

The methods described in the Examples form further preferred aspects of the invention. All combinations of the preferred features described above are contemplated, particularly as described in the Examples.

BRIEF DESCRIPTION OF THE DRAWINGS

The invention will now be described by way of non-limiting Examples with reference to the drawings in which.

EXAMPLES

Figure 1:
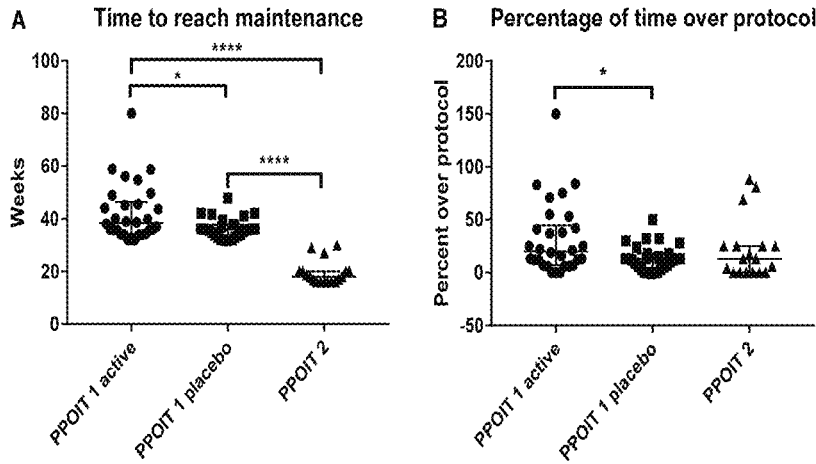
FIG. 1 shows the time in weeks to reach the 2000 mg peanut protein maintenance dose (FIG. 1A) and the percentage of time the build-up phase extended longer than the expected 32 weeks for the standard build-up schedule and the expected 16 weeks for the rapid build-up schedule (FIG. 1B) with medians and interquartile ranges for the standard build-up schedule compared with the rapid build-up schedule. * P<0.05, **** P<0.0001. The Mann-Whitney test was used to determine statistical differences.

Example 1—Comparison of Outcomes for a Protocol with Standard Time to Maintenance Dose (PPOIT-001) and a Protocol with Reduced Time to Maintenance (PPOIT-002)

In this Example peanut OIT protocols were compared in which a standard administration protocol (PPOIT1) and a protocol in which the time to maintenance dose of OIT was reduced (PPOIT2) were used.

Materials and Methods

Study Population

In the PPOIT-001 trial, 62 peanut allergic children, aged 1 to 10 years, were enrolled to the randomized, double-blind placebo controlled trial which combined the probiotic *Lactobacillus rhamnosus* GG (single dose of $2\times10^{10}$ cfu taken daily just before ingestion of peanut OIT) and peanut OIT for a total of 18 months, the first 8 months consisting of the dose-escalation phase comprising a rush day followed by a build-up phase (time to maintenance 32 weeks). In PPOIT-002, 20 peanut allergic children, were enrolled in an open pilot study of the probiotic *Lactobacillus rhamnosus* GG (single dose of $2\times10^{10}$ cfu taken daily before ingestion of peanut OIT) and peanut OIT where the dose escalation phase was shortened to 4 months (time to maintenance 16 weeks).

Children enrolled in PPOIT-001 study were 1 to 10 years of age, with a confirmed diagnosis of peanut allergy as defined by either a positive food challenge to peanut in the past 2 years and a positive SPT or CAP-RAST to peanut, or a positive food challenge or a history of reaction to peanut ever and a positive SPT≥8 mm or a CAP-RAST≥15U/l to peanut.

Children enrolled in PPOIT-002 study were 1 to 12 years of age, with a confirmed diagnosis of peanut allergy as defined by a failed DBPCFC to peanut and a positive SPT or sIgE to peanut at screening or in the preceding 3 months.

Study Conduct

The participants of the PPOIT-001 study were randomised to either receive a peanut OIT together with the probiotic *L rhamnosus*, or placebo with placebo. In PPOIT-002 all participants received active treatment. The treatment began with a rush day (day 0) and the Rush dosing schedule was the same for both studies as shown in Table 3. Before initiating the Rush phase, participants received a single dose of probiotic or placebo (1 scoop dissolved into water). Thereafter, participants received increasing doses of peanut (or placebo OIT), sprinkled onto food every 30 minutes until a final dose of 12 mg peanut protein (cumulative dose 24 mg peanut protein or placebo) was reached. If a participant reacted to one of the doses during the rush phase, the rush schedule was ceased and they commenced the build-up phase at the dose immediately below the reaction-eliciting dose during the rush day, starting on the day after the rush day (i.e. day 1). The remaining rush doses that were not completed on day 0 were incorporated into the build-up phase and subsequent dose increases proceeded through all remaining doses of the rush dosing schedule followed by the doses in the build-up schedule.

Rush day was followed by the build-up phase. The two different build-up schedules for PPOIT-001 and PPOIT-002 are shown in Table 4 and Table 5, respectively. During the build-up phase, the daily dose of peanut OIT or placebo was increased every 2 weeks until a maintenance dose of 2 g was reached. Peanut protein or placebo was taken sprinkled onto food and the dose of probiotic or placebo was mixed with water and taken immediately prior to the OIT or placebo. Each dose increase was administered in hospital under medical supervision.

The dose adjustment rules were similar in both studies and included guidelines for how dosing should be continued if a participant reacted to a dose. If the reaction was mild or moderate (not anaphylaxis) and occurred within 3 days of the scheduled day of dose increase, the updosing would be deferred and the dose would be repeated before increasing, or if the reaction occurred more than 3 days prior to the scheduled day of dose increase, the updosing would proceed according to protocol. If an anaphylaxis reaction occurred, then the immediate next dose would be reduced to the previous dose amount and continued for at least 10 days before proceeding with a dose increase. If a serious anaphylaxis reaction (e.g. reduced blood pressure or loss of consciousness) occurred, then OIT would be discontinued. Time taken for each subject to reach each dose under the PPOIT-002 schedule is shown in Table 11.

Adverse events (AE) were defined as any untoward medical occurrence that occurred in a participant which did not necessarily have a relationship with the investigational product. Details regarding each AE were prospectively collected and documented on each study visit or when advised by the patient throughout the study in their study diary. The information included a description of the event, onset and stop date of the event, severity of the event, as well as suspected relationship to the study treatment. The PPOIT-001 study originally categorised all reactions that met the definition of anaphylaxis (any reaction involving airway or circulation, irrespective of how mild) as a serious adverse event (SAE). Recently, NIH/NIAID Consortium of Food Allergy Research (CoFAR) developed a standardised tool for categorisation of allergic reactions. This tool was adopted for the PPOIT-002 study and was subsequently applied to re-categorise the allergic AEs from PPOIT-001, to allow direct comparison of AE events in the two studies.

The CoFAR categorisation allocates the grading of moderate or severe to most anaphylaxis events and only those reactions that are immediately life threatening are labelled as SAE.

Briefly, the CoFAR tool grades events from 1 to 5, where grade 1 events were mild with symptoms that may include pruritus, swelling or rash or abdominal discomfort, grade 2 events were moderate with symptoms that may include persistent hives, wheezing without dyspnoea or abdominal discomfort/increased vomiting, grade 3 events were severe with symptoms that may include bronchospasm with dyspnoea, severe abdominal pain, throat tightness with hoarseness and transient hypotension, grade 4 events were life threatening and grade 5 resulted in death. Grade 4 and 5 were graded as SAE. The relationship of an AE to study product was assessed using the following categories; probably related, possibly related, unlikely to be related, unrelated.

All randomised participants were included when assessing AEs, irrespective of if and when they withdrew from the study. AEs that were categorized as unrelated to study product or unlikely to be related to study product were excluded from the present study's analyses. For the comparison between PPOIT-001 and PPOIT-002 only moderate and severe AEs and SAEs were included. Two assessors reviewed AE raw data from both PPOIT-001 and PPOIT-002 studies and applied the tool developed by CoFAR to grade severity and attribution of each event. The categorisations were then compared and if consensus reached, the categorisation was accepted. If consensus was not reached, a third independent assessor reviewed and provided final assessment.

TABLE 3

| Peanut OIT protocol rush day (PPOIT-001 and 002) | | |
| --- | --- | --- |
| Dose | Peanut protein | Cumulative dose peanut protein |
| 1 | 0.1 mg | 0.1 mg |
| 2 | 0.2 mg | 0.3 mg |
| 3 | 0.4 mg | 0.7 mg |
| 4 | 0.8 mg | 1.5 mg |
| 5 | 1.5 mg | 3.0 mg |

TABLE 3-continued

| Peanut OIT protocol rush day (PPOIT-001 and 002) | | |
| --- | --- | --- |
| Dose | Peanut protein | Cumulative dose peanut protein |
| 6 | 3.0 mg | 6.0 mg |
| 7 | 6.0 mg | 12 mg |
| 8 | 12 mg | 24 mg |

TABLE 4

| Peanut OIT protocol build-up phase-PPOIT-001 | | |
| --- | --- | --- |
| Dose | Time following rush day at which the dose commences | Peanut protein |
| 9 | 1 day | 24 mg |
| 10 | 2 weeks | 25 mg |
| 11 | 4 weeks | 50 mg |
| 12 | 6 weeks | 75 mg |
| 13 | 8 weeks | 100 mg |
| 14 | 10 weeks | 125 mg |
| 15 | 12 weeks | 150 mg |
| 16 | 14 weeks | 200 mg |
| 17 | 16 weeks | 260 mg |
| 18 | 18 weeks | 330 mg |
| 19 | 20 weeks | 425 mg |
| 20 | 22 weeks | 550 mg |
| 21 | 24 weeks | 715 mg |
| 22 | 26 weeks | 925 mg |
| 23 | 28 weeks | 1.2 g |
| 24 | 30 weeks | 1.55 g |
| 25 | 32 weeks | 2.0 g |

TABLE 5

| Peanut OIT protocol build-up phase-PPOIT-002 | | |
| --- | --- | --- |
| | Time following rush day at which the dose commences | Peanut protein |
| 9 | 1 day | 25 mg |
| 10 | 2 weeks | 50 mg |
| 11 | 4 weeks | 100 mg |
| 12 | 6 weeks | 200 mg |
| 13 | 8 weeks | 400 mg |
| 14 | 10 weeks | 800 mg |
| 15 | 12 weeks | 1.2 g |
| 16 | 14 weeks | 1.6 g |
| 17 | 16 weeks | 2.0 g |

Calculations

Using the dates for a participant's rush day visit and subsequent build-up visits, time to reach maintenance phase and days on each dose were calculated. Time to reach maintenance was expressed as a percentage of the optimal schedule according to protocol and calculated by dividing each participant's actual time to reach maintenance phase with the optimum number of weeks it should have taken them had they progressed through the build-up protocol without deviating due to reactions or being rescheduled for other reasons. The denominator was 32 weeks for the PPOIT-001 groups and 16 weeks for PPOIT-002. The number of delayed build-up visits was extracted from the data by coding for any days on dose that was over 14 days. This would indicate a delayed build-up visit. The number of delayed build-up visits as a percentage of the total number of build-up visits was calculated by dividing the number of delayed build-up visits by the total number of build-up visits the participant had had. Delayed days were calculated by adding all days over 14 days on a dose for each participant together into a total sum of delayed days. Information on dosing on rush day, days on dose and number of missed doses was used to calculate the total cumulative dose taken during the rush day and build-up phase for each participant. To calculate the average dose taken by a participant each week of the build-up phase, the cumulative dose was divided by the number of weeks the participant was on build-up. The number of AEs, their character, severity grade, and relationship to study product was collected from the AE databases.

Statistical Analysis

Statistical analysis was done using Graphpad Prism version 7 (GraphPad Software, Inc. La Jolla, CA, USA). The primary aims of the study were to compare time to reach maintenance, cumulative OIT dose taken during build-up, and number of moderate and severe adverse events between the three groups: PPOIT-001 active, PPOIT-001 placebo, and PPOIT-002. As an expansion of these aims, percentage of time over optimal protocol schedule, number and percentage of delayed build-up visits and total number of delayed days was compared as well. For the time to reach maintenance and delayed days analyses, only participants who reached maintenance were included, as dropouts did not have complete data for these variables. For the comparison of adverse events all participants were included irrespective of if and when they withdrew from the study. For each comparison three Mann-Whitney U test analyses were made comparing PPOIT-001 active vs PPOIT-001 placebo, PPOIT-001 active vs PPOIT-002, and PPOIT-001 placebo vs PPOIT-002. Mann-Whitney U test was chosen since the data was not normally distributed.

Between group comparisons were adjusted for four possible confounders; age, gender, diagnosis of asthma, and SPT wheal size. The subgroups are shown in Table 6. Comparisons across all three groups were performed with Kruskall-Wallis H test and two-group comparisons were performed with Mann-Whitney U test.

Univariate and multivariate regression analyses were performed to investigate the relationships between build-up duration and SU.

Ethics

PPOIT-001 and PPOIT-002 were approved by the Royal Children's Hospital Human Ethics Research Committee (HREC).

Results

In PPOIT-001, 62 children were randomized to either receive active peanut OIT with probiotic *L rhamnosus* (N=31) or placebo with placebo (N=31). In PPOIT-002, 20 children were assigned to receive active peanut OIT and probiotic *L rhamnosus* with a shortened build-up phase. The baseline demographics for the three groups are shown in Table 6. Baseline demographics between the groups were similar with the exception of asthma, age, gender and SPT wheal size. Based on these demographics all three groups were split into subgroups to confirm whether there were important differences between these subgroups (see Table 7). There were no significant differences between the subgroups.

TABLE 6

| Demographic characteristics at study entry | | | |
|---|---|---|---|
| | PPOIT 1 active group (N = 31) | PPOIT 1 placebo group (N = 31) | PPOIT 2 (N = 20) |
| Age (y) | | | |
| Median (IQR) | 6 (4.3 to 7.5) | 5.6 (3.4 to 8) | 7.8 (5.8 to 10.73) |
| Male sex | | | |
| n (%) | 17 (54.8) | 20 (64.5) | 14 (70.0) |
| History of doctor-diagnosed eczema (ever)* | | | |
| n (%) | 24 (77.4) | 24 (77.4) | 16 (94.1) |
| History of doctor-diagnosed asthma (ever) | | | |
| n (%) | 16 (51.6) | 14 (45.2) | 6 (30.0) |
| Peanut-induced SPT wheal size (mm) | 18 | 16 | 11 |
| Median (IQR) | (13 to 22) | (12.5 to 20) | (9 to 15.25) |

TABLE 7

| Subgroup stratifications used in adjusted analyses | | | |
|---|---|---|---|
| Age (y) | Gender | Asthma | SPT-wheal size (mm) |
| ≤5 | Male | Yes | ≤10 |
| <5 | Female | No | <10 |

In the PPOIT-001 active group, 1 child withdrew during the build-up phase because of regular abdominal pain after taking the doses. In the PPOIT-001 placebo group 2 children withdrew, 1 because the family was unable to commit to the study protocol, and 1 because the mother was concerned for the safety and wellbeing of the child after an SAE. In the PPOIT-002 group 2 children withdrew, 1 because the child did not want to continue taking doses and 1 because the child had recurrent abdominal pain in association with doses after updosing to the 100 mg/day dose.

Time to Reach Maintenance was Shorter for Subjects Treated Using PPOIT-002

As shown in FIGS. 1A and in Table 8, the median time to reach maintenance phase was 38.4 weeks (IQR, 34.3 to 46.4) for PPOIT-001 active, 36.0 weeks (IQR, 33.4 to 37.8) for PPOIT-001 placebo, and 18.0 weeks (IQR, 16.0 to 20.0) for PPOIT-002. There was a significant difference between all three groups, PPOIT-001 active vs. PPOIT-001 placebo (P=0.03), PPOIT-001 active vs. PPOIT-002 (P<0.0001), and PPOIT-001 placebo vs. PPOIT-002 (P<0.0001).

As shown in FIG. 1B and Table 8, the median percentage of time by which a participant exceeded the optimum time to reach maintenance phase (32 weeks for PPOIT-001, 16 weeks for PPOIT-002) was 20% (IQR, 7 to 45%) for PPOIT-001 active, 13% (IQR, 4 to 18%) for PPOIT-001 placebo, and 13% (IQR, 0 to 25%) for PPOIT-002. There was a significant difference between PPOIT-001 active and PPOIT-001 placebo (P=0.03), while the values for the other comparisons were not significant, PPOIT-001 active vs. PPOIT-002 (P=0.18), PPOIT-001 placebo vs. PPOIT-002 (P=0.82).

PPOIT-002 was Associated with Fewer Delayed Build-Up Visits and Fewer Number of Delayed Updosing Days The median number of delayed build-up visits attributable to all reasons (including reactions to treatment and logistic reasons) was 5 (IQR, 3 to 7) for PPOIT-001 active, 4 (IQR, 3 to 6) for PPOIT-001 placebo, and 1 (IQR, 0 to 2) for PPOIT-002. There was a significant difference between PPOIT-001 active and PPOIT-002 (P<0.0001), and between PPOIT-001 placebo and PPOIT-002 (P<0.0001).

For PPOIT-002, the median number of build-up visits that were delayed due to treatment related reactions was 0 (IQR, 0 to 1). The median percentage of build-up visits that were delayed due to treatment was 0% (IQR, 0 to 13%).

The median percentage of build-up visits that were delayed was 31% (IQR, 19 to 44%) for PPOIT-001 active, 25% (IQR, 19 to 38%) for PPOIT-001 placebo, and 13% (IQR, 0 to 22%) for PPOIT-002. There was a significant difference between PPOIT-001 active and PPOIT-002 (P<0.0001), and PPOIT-001 placebo and PPOIT-002 (P=0.002).

The median total number of days a participant exceeded their dosing protocol (e.g. stayed on a dose for longer than 14 days) was 48 days (IQR, 18.5 to 87) for PPOIT-001 active, 29 days (IQR, 13 to 50) for PPOIT-001 placebo, and 14 days (IQR, 0 to 19.5) for PPOIT-002. There was a significant difference between all three groups, PPOIT-001 active vs. PPOIT-001 placebo (P=0.04), PPOIT-001 active vs. PPOIT-002 (P<0.0001), and PPOIT-001 placebo vs. PPOIT-002 (P=0.001).

The results are summarised in FIGS. 2A, B and C, and percentage calculations are provided in Table 8.

Cumulative Dose Taken During Build-Up

The median cumulative dose taken during build-up phase was 108.50 g (IQR, 95.44 to 126.20) for PPOIT-001 active, 97.49 g (IQR, 92.64 to 108.60) for PPOIT-001 placebo, and 61.31 g (IQR, 59.40 to 62.34) for PPOIT-002. There was a significant difference between all three groups, PPOIT-001 active vs. PPOIT-001 placebo (P=0.02), PPOIT-001 active vs. PPOIT-002 (P<0.0001), and PPOIT-001 placebo vs. PPOIT-002 (P<0.0001).

The median average dose taken per week in the build-up phase was 2.77 g (IQR, 2.46 to 3.12) for PPOIT-001 active, 2.89 g (IQR, 2.65 to 2.96) for PPOIT-001 placebo, and 3.45 g (IQR, 3.11 to 3.65) for PPOIT-002. There was a significant difference between PPOIT-001 active vs PPOIT-002 (P<0.0001), and PPOIT-001 placebo vs. PPOIT-002 (P<0.0001).

Figure 3:
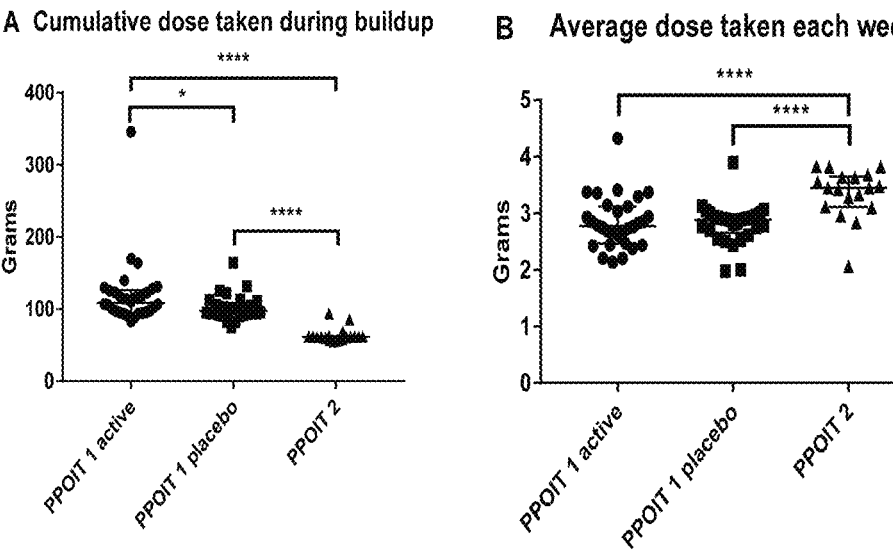
FIG. 3 plots cumulative dose taken during build-up (FIG. 3A) and average dose taken each week (FIG. 3B) with medians and interquartile ranges. * P<0.05, **** P<0.0001. The Mann-Whitney test was used to determine statistical differences.

The results are summarised in FIGS. 3A and B and Table 8.

PPOIT-002 had Fewer Moderate or Severe AEs During Build-Up Phase Compared to PPOIT-001

Figure 4:
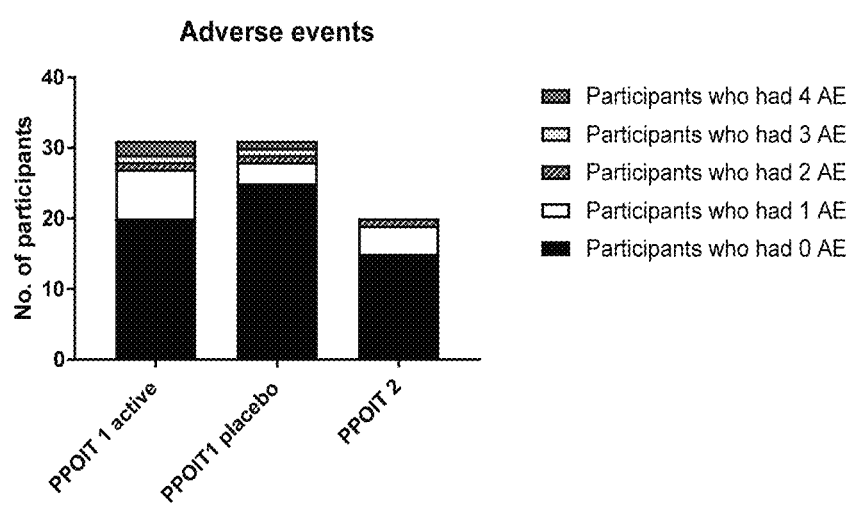
FIG. 4 shows the number of participants with moderate and severe adverse events (AEs) during rush day and build-up phase in the standard build-up schedule and the rapid build-up schedule. The different shadings show how many participants experienced a certain number of moderate to severe AEs.

Data on moderate and severe AEs during build-up phase were available for both PPOIT-001 and PPOIT-002 and were compared. AEs determined to be unlikely or unrelated to study product were excluded. As shown in FIG. 4 and Table 9, at least 1 moderate or severe AE was reported in 35.5% of children in the PPOIT-001 active group, 19.4% in the PPOIT-001 placebo group, and 25.0% in the PPOIT-002 group. The total number of moderate and severe AEs were 20 in the PPOIT-001 active group, 12 in the PPOIT-001 placebo group, and 6 in the PPOIT-002 group. The number of moderate and severe AEs per participant did not differ significantly by group, median 1.5 (IQR, 0-1) for the PPOIT-001 active group, 0 (IQR, 0-0) for the PPOIT-001 placebo group, and 0 (IQR, 0-0.75) for the PPOIT-002 group. During build-up a total of 0.23% (20/8577) of doses resulted in a moderate or severe reaction in the PPOIT-001 active group, 0.16% (12/7364) in the PPOIT-001 placebo group, and 0.24% (6/2449) in the PPOIT-002 group.

During the build-up phase, there was one SAE recorded that was related to study product in the PPOIT-001 placebo group and was an episode of severe abdominal pain and throat tightness. There were no SAE during build-up phase for active PPOIT-001 group or the PPOIT-002 group.

For the PPOIT-002 group, 3 out of the moderate and severe AEs during build-up phase occurred on a build-up day and 3 occurred during home dosing. All of the moderate and severe AEs in the PPOIT-002 group occurred during the first three weeks of the build-up phase (data not shown).

Table 10 shows the frequency of AEs for PPOIT-001 and PPOIT-002 and Table 11 shows the time taken for each subject to reach each dose under the PPOIT-002 schedule.

TABLE 8

Time to reach maintenance, cumulative dose peanut or placebo taken during build-up phase, and delayed build-up visits and days. Kruskall-Wallis test performed to determine p-values

| | PPOIT 1 active (N = 30) | PPOIT 1 placebo (N = 29) | PPOIT 2 (N = 18) | P-value |
|---|---|---|---|---|
| Time to reach maintenance (weeks) | 38.4 | 36 | 18 | <0.0001 |
| Median (IQR) | (34.3 to 46.4) | (33.4 to 37.8) | (16 to 20) | |
| Percentage of time over protocol | 20 | 13 | 13 | 0.0886 |
| Median (IQR) | (7 to 45) | (4 to 18) | (0 to 25) | |
| Cumulative dose taken during build-up (g) | 108.5 | 97.49 | 61.31 | <0.0001 |
| Median (IQR) | (95.44 to 126.2) | (92.64 to 108.6) | (59.40 to 62.34) | |
| Average dose taken each week (g) | 2.77 | 2.89 | 3.45 | <0.0001 |
| Median (IQR) | (2.46 to 3.12) | (2.65 to 2.96) | (3.11 to 3.65) | |
| Delayed days on dose | 48 | 29 | 14 | <0.0001 |
| Median (IQR) | (18.5 to 87) | (13 to 50) | (0 to 19.5) | |
| No. of delayed build-up visits | 5 | 4 | 1 | <0.0001 |
| Median (IQR) | (3 to 7.25) | (3 to 6) | (0 to 2) | |
| Percentage of delayed build-up visits for any reason | 31 | 25 | 13 | 0.0003 |

TABLE 8-continued

| | PPOIT 1 active (N = 30) | PPOIT 1 placebo (N = 29) | PPOIT 2 (N = 18) | P-value |
|---|---|---|---|---|
| | Time to reach maintenance, cumulative dose peanut or placebo taken during build-up phase, and delayed build-up visits and days. Kruskall-Wallis test performed to determine p-values | | | |
| Median (IQR) | (19 to 44) | (19 to 38) | (0 to 22) | |
| No. of build-up visits delayed due to treatment related reactions | N/A | N/A | 0 | |
| Median (IQR) | | | (0 to 1) | |
| Percentage of build-up visits delayed due to treatment related reactions | N/A | N/A | 0 | |
| Median (IQR) | | | (0 to 13) | |

TABLE 9

Characteristics of severe and moderate AEs

| | | PPOIT 1 active group (N = 31) | PPOIT 1 placebo group (N = 31) | PPOIT 2 (N = 20) |
|---|---|---|---|---|
| Patients who experienced ≥ 1 AE | n (%) | 11 (35.5) | 6 (19.4) | 5 (25) |
| No. of AEs per patient | | | | |
| 0 | n (%) | 20 (64.5) | 25 (80.6) | 15 (75) |
| 1 | n (%) | 7 (22.6) | 3 (9.7) | 4 (20) |
| 2 | n (%) | 1 (3.2) | 1 (3.2) | 1 (5) |
| 3 | n (%) | 1 (3.2) | 1 (3.2) | 0 (0) |
| 4 | n (%) | 2 (6.5) | 1 (3.2) | 0 (0) |
| Total no. of AEs | n | 20 | 12 | 6 |
| Median (IQR) | | 0 (0 to1) | 0 (0 to 0) | 0 (0 to 0.75) |

TABLE 9-continued

Characteristics of severe and moderate AEs

| | | PPOIT 1 active group (N = 31) | PPOIT 1 placebo group (N = 31) | PPOIT 2 (N = 20) |
|---|---|---|---|---|
| No. of AEs by time point | | | | |
| Modified rush day | n (%) | 1 (5) | 1 (8.3) | 1 (16.7) |
| Build-up phase | n (%) | 19 (95) | 11 (91.7) | 5 (83.3) |
| Home dosing | n (%) | N/A | N/A | 3 (50) |
| Updosing day | n (%) | N/A | N/A | 3 (50) |

TABLE 10

Frequency of AEs as a percentage of total doses

| | | PPOIT 1 active group (N = 31) | PPOIT 1 placebo group (N = 31) | PPOIT 2 (N = 20) |
|---|---|---|---|---|
| Moderate AEs | % (n) | 0.22 (19 of 8577) | 0.15 (11 of 7364) | 0.20 (5 of 2449) |
| Severe AEs | % (n) | 0.01 (1 of 8577) | 0.01 (1 of 7364) | 0.04 (1 of 2449) |
| SAEs | % (n) | 0 | 0.01 (1 of 7364) | 0 |

TABLE 11

Time taken for each subject to reach each dose under the PPOIT2 schedule.

| Patient no. | days to 25 mg | days to 50 mg | days to 100 mg | days to 200 mg | days to 400 mg | days to 800 mg | days to 1200 mg | days to 160 0mg | days to 2 g |
|---|---|---|---|---|---|---|---|---|---|
| 01 | 1 | 14 | 28 | 42 | 57 | 70 | 84 | 98 | 112 |
| 02 | 1 | 14 | 28 | 42 | 63 | 77 | 91 | 105 | 119 |
| 03 | 1 | 14 | 28 | 42 | 56 | 70 | 85 | 98 | 112 |
| 04 | 1 | 14 | 28 | 42 | 56 | 70 | 84 | 98 | 112 |
| 05 | 1 | 14 | 33 | 51 | 60 | 75 | 89 | 103 | 117 |
| 06[a] | 91 | 105 | 126 | 140 | 154 | 168 | 182 | 196 | 210 |
| 07 | 1 | 14 | 30 | 44 | 72 | 98 | 112 | 126 | 140 |
| 09 | 1 | 14 | 28 | 42 | 56 | 70 | 84 | 98 | 112 |
| 10[b] | 1 | 70 | 84 | 98 | 136 | 140 | 161 | 175 | 203 |
| 12[c] | 1 | 42 | 56 | 70 | 84 | 98 | 112 | 126 | 140 |
| 13 | 1 | 14 | 28 | 56 | 70 | 84 | 98 | 112 | 126 |
| 14 | 1 | 14 | 28 | 42 | 56 | 70 | 84 | 98 | 112 |

TABLE 11-continued

Time taken for each subject to reach each dose under the PPOIT2 schedule.

| Patient no. | days to 25 mg | days to 50 mg | days to 100 mg | days to 200 mg | days to 400 mg | days to 800 mg | days to 1200 mg | days to 160 0mg | days to 2 g |
|---|---|---|---|---|---|---|---|---|---|
| 16 | 1 | 19 | 33 | 61 | 75 | 89 | 103 | 117 | 131 |
| 17[d] | 42 | 56 | 70 | 84 | 98 | 112 | 126 | 140 | 189 |
| 18 | 1 | 28 | 56 | 70 | 84 | 98 | 112 | 126 | 140 |
| 19 | 1 | 28 | 42 | 56 | 70 | 84 | 98 | 112 | 126 |
| | | | | Summary statistics | | | | | |
| mean | 9.1875 | 29.625 | 45.375 | 61.375 | 77.9375 | 88.86 | 103.59 | 117.82 | 134.36 |
| median | 1 | 14 | 31.5 | 53.5 | 70 | 84 | 98 | 112 | 126 |
| IQR | 1-1 | 14-31.5 | 28-56 | 42-70 | 56.75-84 | 70-98 | 84.75-112 | 98-126 | 112-140 |
| | | | | tests for normality (performed on SPSS) | | | | | |
| Kolmogorov-Smirnov | | | | | | 0.026 | | 0.016 | 0.017 | 0.001 |
| Shapiro-Wilk | | | | | | 0.002 | | 0.001 | 0.001 | 0.001 |

Footnote to Table 11:
[a]reacted to 0.8 mg on RUSH day
[b]reacted during BU to 50 mg
[c]reacted during BU to 50 mg
[d]reacted to 1.5 mg on RUSH day Likelihood of Achieving Sustained Unresponsiveness at the End-of-Treatment.

At the end of 18 months of treatment for both PPOIT 001 and PPOIT 002, the presence of sustained unresponsiveness (SU) was tested by double blind placebo controlled peanut challenge.

Using pooled data from PPOIT-001 active group and PPOIT-002, a univariate regression analysis was performed to determine whether the duration of the build-up phase was associated with the likelihood of achieving sustained unresponsiveness at the end-of-treatment. We found that a shorter build-up phase was associated with a significantly increased likelihood of achieving sustained unresponsiveness. Specifically, for every week that the build-up phase is longer, the likelihood or more specifically the odds of a subject achieving sustained unresponsiveness was 7.5% (1-0.925) lower, p=0.026 (see Table 12). Moreover, the median time in build-up phase was 11 weeks shorter in those who achieved sustained unresponsiveness compared to those who did not. In contrast, the total cumulative dose of peanut protein received during OIT and the dose reached on rush day were not associated with likelihood or odds of achieving sustained unresponsiveness. Univariate regression analyses showed that asthma at study entry and allergic rhinitis at study entry also influenced the likelihood or odds of achieving SU. A logistic regression model was therefore run to estimate the effects of asthma, allergic rhinitis and build-up duration on SU. This revealed that Build-up duration remained a significant predictor of SU. Specifically, in this model including both baseline asthma and allergic rhinitis, the likelihood or odds of achieving SU were 1.1 time greater for every 1 week reduction in build-up duration.

TABLE 12

| Correlation between build-up time and sustained unresponsiveness | Odds Ratio of achieving SU | p value | 95% CI |
|---|---|---|---|
| For every 1 week that Build-up time is increased (unadjusted univariate regression analysis) | 0.925 | 0.015 | 0.87-0.99 |
| For every 1 week that Build-up time is increased (Logistic regression model including baseline asthma and allergic rhinitis) | 0.91 | 0.025 | 0.84-0.99 |

Discussion

The purpose of this study was to compare the time to maintenance dose in PPOIT-001 (32 weeks) with that of PPOIT-002 (16 weeks). Specifically, the time to reach maintenance, delays in scheduled build-ups, cumulative dose taken during Rush and build-up phase, and number of adverse events were compared. This study found that the PPOIT-002 group's build-up phase was either equal or superior to both PPOIT-001 active and PPOIT-001 placebo build-up phase in terms of tolerability and frequency of adverse events.

The time to reach maintenance was significantly shorter for the PPOIT-002 group. This is to be expected because the schedule was half as long as PPOIT-001. In addition, the PPOIT-002 build-up schedule was well tolerated despite being shorter. Had the new build-up schedule not been well tolerated, then delays because of reactions would have put the median time to reach maintenance for the PPOIT-002 group (which was 18 weeks) closer to the PPOIT-001 active (38 weeks) and PPOIT-001 placebo (36 weeks) groups. When adjusting for the different build-up schedules by only looking at the median percentage of time that the participants exceeded the optimum time to reach maintenance, one can still see that PPOIT-002 (13% over optimum time) is equal to the PPOIT-001 placebo group (13%) and superior to the PPOIT-001 active group (20%).

Figure 2:
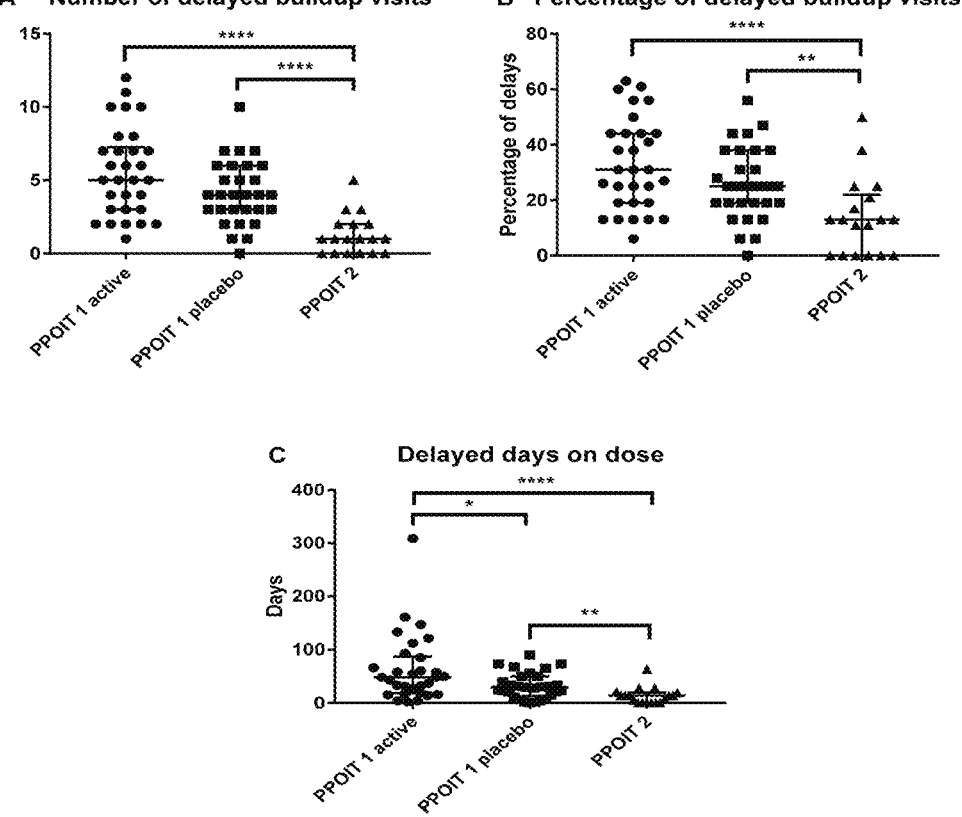
FIG. 2 shows the number of delayed build-up visits (FIG. 2A), percentage of delayed build-up visits (FIG. 2B), and delayed days on dose (FIG. 2C) with medians and inter-quartile range for the standard build-up schedule and the rapid build-up schedule. * P<0.05, ** P<0.01, P<0.0001. The Mann-Whitney test was used to determine statistical differences.

When comparing protocol deviations in the form of delayed build-up visits and number of delayed days FIG. 2 shows that the PPOIT-002 group deviated significantly less from the build-up protocol than both PPOIT-001 active and PPOIT-001 placebo. When only looking at the PPOIT-002 group it is clear that the median number of build-up visits that were delayed because of treatment related reactions is 0, meaning that the majority of build-up visits were delayed due to logistic reasons (e.g. public holidays, family being unable to attend, study team unable to accommodate scheduled visit) and the more rapid dose escalation protocol of PPOIT-002 was not associated with an increased number of adverse reactions that resulted in delayed build-up visits. A longer build-up phase equals more build-up visits that could in theory be delayed because of logistic reasons, which could be one of the reasons why the PPOIT-001 participants deviated more from protocol since they had twice as many build-up visits to attend. The very few number of build-up visits in PPOIT-002 that were delayed because of treatment show that the build-up was well tolerated and did not often lead to complications in the form of reactions that would force a protocol deviation and delay.

The number of AEs were lower in the PPOIT-002 group compared with the PPOIT-001 active group, although there was overall a very small number of AE that occurred: 20 (0.21% of doses given) in PPOIT-001 active, 12 (0.16% of doses given) for PPOIT-001 placebo, and 6 (0.24% of doses given) for PPOIT-002. At the very least, PPOIT-002 was non-inferior compared to PPOIT-001 in terms of safety and tolerability despite incorporating a more rapid dose escalation regimen. The cumulative dose taken during build-up phase is naturally smaller for PPOIT-002 as they were on build-up for half the time that subjects in PPOIT-001 active were. When looking at the average dose taken each week, PPOIT-002's is higher since the updosing was steeper with doses being doubled up until the 800 mg dose. When calculating what the optimum dose taken for the entire treatment course is (assuming a participant follows the dosing protocol and does not miss any doses) then the total cumulative dose would be 654 g for PPOIT-001 (32 weeks build-up and 40 weeks maintenance), and 845 g for PPOIT-002 (16 weeks build-up and 56 weeks maintenance).

The multi-dimensional approach provided herein provides more comprehensive understanding of the tolerability and safety of the new dose escalation schedule for PPOIT-002 when compared to PPOIT-001. Time to reach maintenance can be used to assess the tolerability of the treatment together with the percentage of time over optimum, and number of delayed build-up visits. Had the new dose escalation schedule been poorly tolerated then the time to reach maintenance would have been longer, the percentage of time over optimum would be higher, and there would have been more delayed build-up visits.

When comparing the moderate to severe AEs for PPOIT-001 and PPOIT-002, it was unexpectedly observed that PPOIT-002 had substantially similar rates of moderate to severe AEs despite the fact that the build-up phase in PPOIT-002 was half the period of time. The rates of AEs from PPOIT-001 and PPOIT-002 are only for the rush and build-up phases of the treatment and may therefore be lower than what they would have been had AEs from the entire treatment span been included (i.e. rush, build-up and maintenance phase). However, most peanut OIT studies that have stratified AE rates based on treatment phase, have found that the majority of AEs occur in the beginning of treatment, during the rush day and build-up phase and therefore it is unlikely that the AE rates would be significantly higher than shown here.

Compared to many of these studies the AE reporting in PPOIT-002 and PPOIT-001, is robust and gives an accurate image of the AEs that occurred during the studies being based on the CoFAR severity grading scale.

Previous peanut OIT schedules have applied gradual dose escalation to avoid AEs as most reactions occur during the build-up phase particularly on days when the dose is increased. Therefore, the prior art has shifted to slower dosing schedules in order to minimise the rate of AEs during dose escalation—for example a recent large multicentre trial of 300 mg OIT applied a build-up phase of 26 weeks to reach 300 mg (PALISADE study—Vickery 2018 NEJM, supra.). The improved safety profile of PPOIT-002 is believed to be due to the faster build-up schedule of peanut OIT since that was the only parameter of dosing that was modified. While it is possible that the probiotic enabled the faster build-up schedule to be successfully applied, it is apparent that the only change between PPOIT-001 and PPOIT-002 was the faster build-up schedule (completed in half the time compared with the PPOIT-001 schedule). For peanut OIT to be implemented in a clinical setting it has to be practical. A long build-up phase where participants have to visit the hospital every two weeks for updosing is both demanding on families and resource intensive since there has to be a doctor and nurse present for each visit. A shorter build-up with steeper dose increases means fewer visits and less resources spent, something that has until now not proven feasible because of a higher rate of AEs and less tolerability. However, the findings in this study surprisingly suggest that using a faster build-up schedule may be possible without compromising safety. Furthermore, the shorter build-up was unexpectedly associated with a higher likelihood or odds of achieving sustained unresponsiveness. The comparison done in our study between PPOIT-001 and PPOIT-002, where the only thing that was changed was the dose escalation schedule, indicates that a shorter dose escalation schedule is possible for treating peanut allergy without reducing tolerability and compromising safety.

Example 2: Determination of Induction of pDCS by Probiotics

This example reports the results of experiments in which the effects of probiotics on the number of circulating plasmacytoid dendritic cells (pDC) after oral administration of the probiotic for 2 weeks in healthy adults with or without allergic disease were examined.

Materials and Methods

Administration of Probiotics 120 healthy adults were recruited. Six different commercially available probiotics were tested (Table 13). Each probiotic was administered to 20 healthy adults as a daily standard dose for 2 weeks. Participants were assigned sequentially to receive one of the six probiotics. Subjects were considered 'healthy' in that they were generally well without serious illness and not taking immunomodulatory therapies. Presence of allergic disease was not an exclusion criteria, as 40%-50% of the Australian population are affected by one or more of the allergic conditions (asthma, allergic rhinitis, eczema, food allergy). To determine if the effects of probiotics were similar in adults with and without allergic disease, subjects were subdivided into those without allergic disease and those with allergic disease. Details of the allergic diseases present in the healthy adults is shown in Table 14.

TABLE 13

| Probiotic dosages | |
|---|---|
| Probiotic | Dose |
| *Lactobacillus rhamnosus* GG | 20 billion CFU/day |
| *Bifidobacterium lactis* | 10 billion CFU/day |
| Yeast (*Saccharomyces boulardii*) | 10 billion CFU/day |
| *E. coli* Nissle 1917 | 1 billion CFU/day |
| *Streptococcus thermophilus* | 20 billion CFU/day |
| *Bifidobacterium breve* | 20 billion CFU/day |

TABLE 14

Description of allergic disease amongst tested subjects.

| | All subjects N = 120 | LGG N = 20 | B. lactis N = 20 | S. boulardii N = 20 | E. coli Nissle 1917 N = 20 | S. thermo-philus N = 20 | B. breve N = 20 |
|---|---|---|---|---|---|---|---|
| Age years median (SD) | 35.5 (9.8) | 32.5 (9.6) | 37.5 (11.0) | 34.0 (7.8) | 39.5 (8.8) | 38.0 (9.0) | 31.0 (12.2) |
| Female sex n (%) | 95 (79) | 17 (85) | 17 (85) | 18 (90) | 5 (75) | 4 (80) | 0 (0) |
| Food allergy n (%) | 2 (2) | 0 (0) | 2 (10) | 0 (0) | 0 (0) | 0 (0) | 0 (0) |
| Asthma n (%) | 25 (21) | 2 (10) | 3 (15) | 6 (30) | 3 (15) | 5 (25) | 6 (30) |
| Eczema n (%) | 17 (14) | 3 (15) | 6 (30) | 4 (20) | 3 (15) | 1 (5) | 0 (0) |
| Allergic rhinitis n (%) | 38 (32) | 6 (30) | 8 (40) | 7 (35) | 7 (35) | 5 (25) | 5 (26.3) |
| Any allergic disease n (%) | 58 (48) | 9 (45) | 12 (60) | 13 (65) | 8 (40) | 7 (35) | 9 (45) |
| No allergic disease n (%) | 62 (52) | 11 (55) | 8 (40) | 7 (35) | 12 (60) | 13 (65) | 11 (55) |

Blood Collection

A 20 mL blood sample was collected prior to probiotic administration (day 0) and after 14 days of probiotic administration (day 14). Blood samples were processed by density gradient centrifugation within 2 hours of collection to separate the plasma and peripheral blood mononuclear cells (PBMCs). PBMCs were cryopreserved and stored in liquid nitrogen for future batched analyses.

Cell Culture for 48 hrs

PBMCs were thawed using the ThawSTAR Automated Cell Thawing System (MedCision, San Rafael, CA). Upon thawing, cells were added dropwise to 10 ml of cold RPMI (Gibco Life Technologies, Grand Island, NY) with 2% Fetal Bovine Serum (FBS) and spun at 400 g for 5 mins. Supernatant was removed and cells were resuspended in 1 ml of 2% FBS in RPMI in preparation for counting. Cell counts were determined by trypan blue exclusion using TC20 automated cell counter (Biorad, Hercules, CA).

PBMC cultures were set up in round bottom 96-well plate with 200,000 cells/well incubated with or without antigen (heat-killed probiotic or media alone) in AIM-V serum free medium (Gibco Life Technologies, Grand Island, NY) with $4 \times 10^{-5}$ M 2-mercaptoethanol for 48 hrs at 37° C. in 5% $CO_2$.

Flow Cytometric Analysis of pDC

Prior to analyses, plates were spun at 400 g, 4° C. Supernatant was removed and placed in another 96-well plate and frozen at −80° C. for future analysis. Cells remained in the wells they were cultured in, 200 μl of PBS was added to each well and plates spun at 400 g, 4° C. Plates were 'flicked' into the sink to remove PBS wash. One hundred microliters of Fixable Viability Dye 510 (BD Biosciences, San Jose, CA) prepared at 0.5 μl/ml in PBS was added to each well, mixed thoroughly and incubated at room temperature (RT), light protected for 15 mins. One hundred microliters of FACS buffer (2% FBS in PBS) was added to each well and plates spun at 400 g, 4° C. and flicked. Antibody cocktail consisting of anti-human HLA DR BB515, CD123 PerCPy5.5, CD11c PE-Cy7, CD1c-PE, lineage (CD3, CD19, CD20 APC-H7 and CD56) APC-Cy7, CD14 V450 and CD16 BUV395 (all antibodies purchased from BD Biosciences, San Jose, CA except for CD123 and CD56 which were from Biolegend, San Diego, CA) were added to each well at a predetermined titre (Table 15) in 40 μl of FACS buffer, mixed thoroughly and incubated for 20 mins on ice. Unbound antibody was washed out in 200 μl of FACS buffer, plates spun and flicked, then 150 μl of FACS buffer added to each well for analysis on the Fortessa X-20 high throughput system (HTS) (BD Biosciences, San Jose, CA.) Compensation controls for each fluorophore were prepared on anti-mouse Ig CompBeads (BD Biosciences, San Jose, CA) with compensation performed by BD FACS-DIVA software (BD Biosciences, San Jose, CA). About 200,000 events were collected per well.

TABLE 15

Antibody titres, fluorophore, clone, vendor and catalogue number.

| Antibody | Fluorophore | Dilution | Clone | Vendor | Cat# |
|---|---|---|---|---|---|
| HLA DR | BB515 | 1:200 | G46-6 | BD | 564516 |
| CD123 | PerCPCy5.5 | 1:20 | 7G3 | BD | 558714 |
| CD11c | PE-Cy7 | 1:100 | B-Ly6 | BD | 561356 |
| CD1c | PE | 1:40 | F10/21A3 | BD | 564900 |
| Lineage (CD3, CD19, CD20, CD56) | APC-H7 | | | BD | |
| CD3 | APC-H7 | 1:100 | SK7 | BD | 560176 |
| CD19 | APC-H7 | 1:100 | SJ25C1 | BD | 560177 |
| CD20 | APC-H7 | 1:100 | 2H7 | BD | 560734 |
| CD56 | APC-Cy7 | 1:100 | NCAM | Biolegend | 362512 |
| CD14 | V450 | 1:200 | MOP9 | BD | 560349 |
| CD16 | BUV395 | 1:200 | 3G8 | BD | 563785 |
| Live/dead BV510 | BV510 | | | | 564406 |

Fortessa X-20 HTS settings
Sample Flow Rate (μl/sec) 2.5
Sample Volume (μl) 125
Mixing Volume (μl) 100
Mixing Speed (μl/sec) 200
Number of Mixes 3
Wash Volume (μl) 400

Post-Acquisition Analysis

Post-acquisition analysis was performed by FlowJo v10.3 (FlowJo, LLC, Ashland, OR). pDC were identified as HLA-DR+Lineage-(CD3, CD19, CD20, CD56) CD14-CD16-CD11c-CD123+ cells. The number of pDC in HK probiotic stimulated cultures was calculated by subtracting the proportion of pDC in unstimulated cultures from the proportion of pDC in HK probiotic stimulated cultures to adjust for nonspecific variation in baseline pDC numbers between subjects and across different time points.

Statistical Analysis

Data are presented as the median and interquartile range for each time point.

Results

Effect of In Vivo Probiotic Supplementation on pDC Proportions in Peripheral Blood Median proportions of pDC in PBMC cultures from healthy adults were increased in all probiotic groups at day 14 (14 days after treatment) compared with day 0 (Table 16).

pDC proportions increased by 2-fold from day 1 to day 14 with LGG (from 8.49 to 17.56%), *B. lactis* (increase from 6.31 to 11.54), *S. boulardii* (from 1.85 to 3.12%) and *E. coli* Nissle 1917 (from 3.76 to 7.21%) and increased by 4 fold from day 1 to day 14 with *S. thermophilus* (from 0.45 to 1.91) and *B. breve* (from 0.61 to 2.45).

Figure 5:
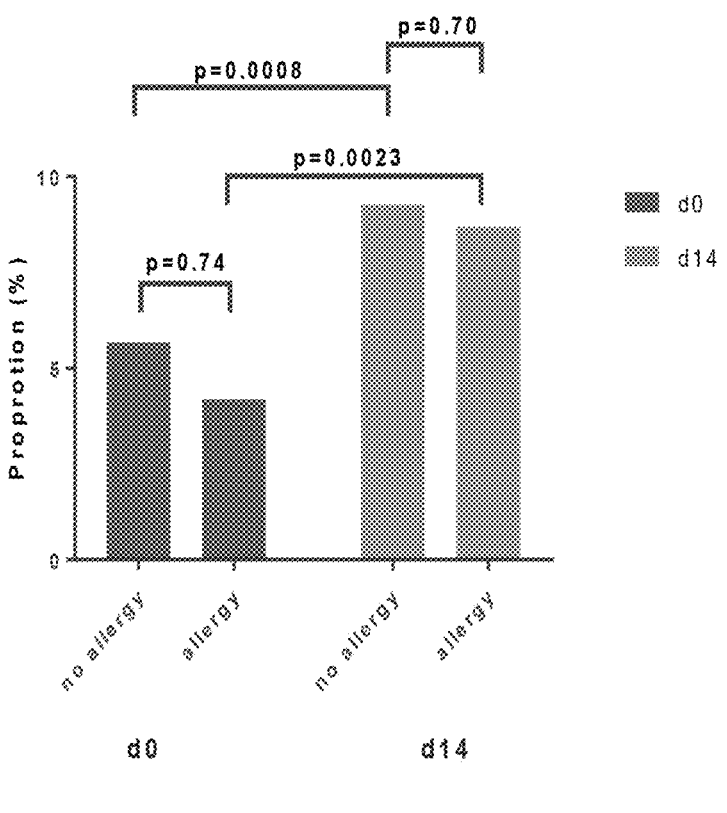
FIG. 5 shows the proportions of pDCs in adults with (n=58) and without (n=62) allergic disease before and after 14 days of treatment with probiotics. The Mann-Whitney test was used to determine statistical differences between subjects with and without allergic disease and the Wilcoxon matched-pairs signed rank test was used to determine the statistical differences between subjects assessed on day 0 or day 14.

The effects of probiotics on pDC proportions were then examined according to presence or absence of allergic disease to determine if probiotic effects were similar for healthy adults with and without allergic disease. At both day 0 (before probiotic treatment) and at day 14 (after probiotic treatment), the proportions of pDCs in adults with and without allergic disease were similar (and not significantly different, p>0.05), indicating that probiotic induction of pDCs is not altered by the presence of allergic disease (FIG. 5).

TABLE 16 pDC proportions in PBMC cultures from healthy adults treated with probiotic for 14 days

| Probiotic | Pre-treatment (day 0) median | IQR 25-75% percentile | Post-treatment (day 14) median | IQR 25-75% percentile | Fold-change |
|---|---|---|---|---|---|
| LGG | 8.49 | 2.61-13.08 | 17.56 | 6.10-23.78 | 2.1 |
| *B. lactis* | 6.31 | 2.39-13.26 | 11.54 | 4.61-23.75 | 1.8 |
| *S. boulardii* | 1.85 | 0.48-2.53 | 3.12 | 0.97-5.06 | 1.7 |
| *E. coli* Nissle 1917 | 3.76 | 2.40-6.52 | 7.21 | 4.63-13.97 | 1.9 |
| *S. thermophilus* | 0.45 | −2.02-2.22 | 1.91 | −1.93-7.36 | 4.2 |
| *B. breve* | 0.61 | −0.26-3.19 | 2.45 | 1.1-7.12 | 4.0 |

The data show that oral administration of six different probiotics from different genera to healthy adults for 14 days leads to systemically detectable increases in pDC proportions. The effect of oral probiotic administration on the pDC response capacity was assessed by measuring the number of pDC generated in vitro (in HK probiotic stimulated cultures to mimic the in vivo exposure) before and after the oral administration of probiotic. The data show that the production of pDC is greater after 14 days of probiotic supplementation compared with day 0. The increases in pDC numbers following 14 days of oral administration of probiotic are consistent with an increased capacity to induce antigen-specific Treg which in turn inhibit the allergic response (Colonna et al, Nat Immunol 5:1219-1226, 2004; Akdis and Akdis, WAO J. 8:17, 2015). pDC present encountered antigens to antigen-specific naïve T cells and direct the naïve T cells to differentiate into regulatory T cells (Treg). The effects of probiotics on pDCs was similar in adults with and without allergic disease (FIG. 5).

Example 3—Comparison of PPOIT-003 Data to Prior Art

PPOIT-003 was a 3 arm multicentre randomised controlled clinical trial conducted using the same build-up protocol as PPOIT-002. Subjects were randomised to receive one of three interventions-placebo, probiotic added to peanut OIT, and peanut OIT without probiotic. The treatment period was 18 months, after which patients were tested for both desensitization and sustained unresponsiveness (SU), using the same food challenge as used in PPOIT2.
Comparison of SU Rates Achieved Following Peanut OIT (without Probiotic) Using the Shorter Build-Up Regimen with the Prior Art (Vickery 2014 Supra.)

A randomised trial was conducted comparing probiotic peanut OIT vs peanut OIT alone vs placebo (PPOIT-003 study). OIT alone induced SU in 50.6% of subjects compared with 5.1% of placebo treated subjects. This rate of SU with peanut OIT is higher than what has been reported when OIT was administered using a longer duration in a similar population of subjects with similar age and peanut SPT wheal size (Table 17). This suggests that peanut OIT administered using a shorter duration led to a higher rate of SU compared with peanut OIT administered using a longer duration. Furthermore, the prior study of peanut OIT using a longer duration also used a higher maintenance dose and shorter period of allergen elimination before testing for SU, which are both considered to increase the likelihood or odds of achieving SU.

TABLE 17

Comparison of OIT arm in PPOIT-003 study with OIT Prior art

| | PPOIT-003 study OIT (n = 83) | PPOIT-003 study Placebo (n = 39) | Vickery 2014 supra OIT (n = 39) |
|---|---|---|---|
| Build-up duration | 16 weeks to 2000 mg | 16 weeks to 2000 mg | 20 weeks to 300 mg followed by 4-5 years to 4000 mg |
| SU (ITT) | 50.6% (42/83) | 5.1% (2/39) | 30.8% (12/39) |
| SU measure | 8-week SU 5000 mg | 8-week SU 5000 mg | 4-week SU 4000 mg |
| OIT maintenance dose | 2000 mg | 2000 mg | 4000 mg |
| Age range (median) | 1-10 years (5.7 years) | 1-10 years (5.9 years) | 1-16 years |
| Peanut SPT mm Mean (SD) | 12.6 (5.20) | 12.7 (5.82) | Approx. 12.5 |

Previous studies have suggested that longer total duration of treatment and higher maintenance OIT dose allow an increase in the sustained unresponsive (SU) rate. Therefore, the higher SU rate in a similar age group of patients demonstrated with peanut OIT in the PPOIT-003 study, despite shorter overall duration of the treatment and lower maintenance dose was surprising. It is postulated this surprising result is due to the more rapid initial dosing to achieve 2000 mg in as little as 16 weeks.
Comparison of Safety and Tolerability of Peanut OIT Using a Shorter Build-Up Duration with the Prior Art

TABLE 18

Comparison of safety events in the OIT arm of the PPOIT-003 study with the OIT arm of the PALISADE study (Vickery 2018 NEJM, supra.)

| | PPOIT-003 Study | | PALISADE Study | |
|---|---|---|---|---|
| | OIT n=83 | Placebo n=39 | AR101 n=372 | Placebo n=124 |
| Gastrointestinal | | | | |
| Abdominal pain | 54.2% (45) | 33.3% (13) | 52.2% (194) | 24.2% (30) |
| Vomiting | 31.3% (26) | 17.9% (7) | 41.4% (154) | 24.2% (30) |
| Respiratory | | | | |
| Cough | 22.9% (19) | 0% (0) | 40.9% (152) | 33.9% (42) |
| Dyspnea | 1.2% (1) | 5.1% (2) | 11.8% (44) | 4.0% (5) |

TABLE 18-continued

Comparison of safety events in the OIT arm of the
PPOIT-003 study with the OIT arm of the
PALISADE study (Vickery 2018 NEJM, supra.)

| | PPOIT-003 Study | | PALISADE Study | |
|---|---|---|---|---|
| | OIT n=83 | Placebo n=39 | AR101 n=372 | Placebo n=124 |
| Multiple respiratory symptoms Skin and subcutaneous | 10.8% (9) | 5.1% (2) | Not reported | Not reported |
| Urticaria | 54.2% (45) | 46.2% (18) | 38.4% (143) | 24.2% (30) |
| Serious Adverse Events (SAEs) | 4.8% | 0% | 5.6% | 1.6% |
| Overall withdrawal rate | 20.5%* | 10.3% | 21.0% | 7.3% |
| Withdrawals due to AE's | 3.6% | 0% | 11.6% | 2.4% |

*PPOIT-003 OIT withdrawal rate includes 4 subjects who withdrew from treatment but remained on study. The rate of study withdrawals was 15.7% (13/83).

The greatly increased peanut OIT dosing schedule in PPOIT-003 (2000 mg reached within 16 weeks compared with 300 mg reached in 24 weeks in PALISADE) would have been expected to result in an increased number of adverse events. We have compared-Proportion of subjects reporting TEAEs involving GI, Respiratory and Skin (SOC and PT), as well as total SAEs, overall withdrawal rates and withdrawals due to AEs. It is surprising that even without the probiotic these events are not increased.

The exposure adjusted incidence rate of AEs can also be used to compare safety of the shortened schedule with slower schedules. Exposure adjusted incidence rate of AEs is calculated by dividing the number of AEs by the actual years of treatment, allowing direct comparison of treatments where there is variation in duration of treatment. Table 19 compares the exposure adjusted incidence of AEs reported with peanut OIT (2000 mg maintenance dose) administered using a shorter duration (in the PPOIT-003 study) to peanut OIT administered using a longer and lower 300 mg maintenance dose (in the PALISADE study). The exposure adjusted incidence rate of AEs is approximately 4 times lower with the faster schedule despite reaching a 6-7 fold higher maintenance dose.

TABLE 19

Comparison of exposure adjusted incidence rate of AEs in the OIT arm of the PPOIT-003 study with the OIT arm of the PALISADE clinical trial (Vickery 2018 NEJM, supra).

| | PPOIT-003 trial 2000 mg maintenance dose | | | PALISADE trial 300 mg maintenance dose | | |
|---|---|---|---|---|---|---|
| | Number of TEAEs | Years of Exposure (on treatment) | Exposure adjusted rate | Number of TEAEs | Years of Exposure (on treatment) | Exposure adjusted rate |
| OIT | 1228 | 108.0 | 11.4 | 12489 | 307.0 | 40.7 |
| Placebo | 116 | 55.5 | 2.1 | 617 | 108.8 | 5.7 |

Comparison of the Effect of Inclusion of the Probiotic on Safety Signals

In the PPOIT003 study, a direct comparison of the effect of adding the probiotic to peanut OIT can be made by comparing subjects receiving probiotic peanut OIT vs those receiving peanut OIT alone. The rate of withdrawals, dose adjustments during build-up phase, proportion of subjects reporting AEs, exposure adjusted incidence rate of AEs can provide information on the tolerability and safety of the treatment schedule.

All oral immunotherapy protocols allow for dose adjustments where a child has a severe reaction to the dose being given. In these circumstances the dose is reduced for a period of time. As a result, the number of dose adjustments occurring during the escalation phase gives an indication of how well tolerated the treatment was in that cohort.

TABLE 20

Comparison of dose adjustments in the PPOIT-003 study in subjects receiving probiotic with peanut OIT (PPOIT) and peanut OIT alone (OIT)

| | PPOIT (n = 79) | OIT (n = 83) | Placebo (n = 39) |
|---|---|---|---|
| Subjects requiring dose adjustment during build-up | 10.1% (8) | 16.9% (14) | 12.8% (5) |
| Total number of dose adjustments | 12 | 16 | 8 |
| Dose at which adjustment occurred, % (n) | 16.7% (2) | 56.3% (9) | 75.0% (6) |
| 3 mg-400 mg | | | |
| 800 mg-2000 mg | 83.3% (10) | 43.8% (7) | 25.0% (2) |

The number of withdrawals from a study or from treatment provides an indication of tolerability of a treatment. In the PPOIT-003 study, there were fewer withdrawals in subjects receiving Probiotic together with OIT compared with subjects receiving OIT alone (Table 21)

TABLE 21

Comparison of withdrawals in the PPOIT003 study in subjects receiving peanut OIT with probiotic (PPOIT) and peanut OIT alone (OIT)

| | PPOIT (n = 79) | OIT (n = 83) | Placebo (n = 39) |
|---|---|---|---|
| Withdrawals* | 12.7% (10) | 20.5% (17) | 10.3% (4) |
| Withdrawals due to AE | 2.6% (2) | 3.6% (3) | 0.0% (0) |

*Includes 6 subjects who withdrew from treatment but remained on study - 2 in the PPOIT group and 4 in OIT group.

Effects in 1-5 Year Olds

The beneficial effect of the probiotic was particularly pronounced in children between the ages of 1 and 5 years as shown in Tables 22 & 23 which show a comparison of the withdrawal rates and adverse events in the 1 to 5 year age group in subjects treated with probiotic+OIT (PPOIT) and OIT alone. Results show that in this younger age group, the probiotic improves tolerability of the peanut OIT treatment (fewer withdrawals), likely due to a protective effect against systemic and gastrointestinal side effects.

TABLE 22

| Comparison of withdrawals in the 1-5 year old age group | | | |
|---|---|---|---|
| Reason for withdrawal | PPOIT n = 41 | OIT n = 43 | Placebo n = 20 |
| Total | 4.9% (2/41) | 18.6% (8/43) | 10.0% (2/20) |
| Adverse event | 0.0 (0) | 2.4 (1) | 0.0 (0) |
| Lack of patient compliance | 2.4 (1) | 4.7 (2) | 0.0 (0) |
| Patient/Caregivers decision | 2.4 (1) | 7.0 (3) | 5.0 (1) |
| Relocated while in the study | 0.0 (0) | 0.0 (0) | 5.0 (1) |
| Study is an inconvenience | 0.0 (0) | 0.0 (0) | 0.0 (0) |
| Other (specify) | 0.0 (0) | 4.7 (2) | 0.0 (0) |

TABLE 23

| Comparison of adverse events in the 1-5 year old age group | | | |
|---|---|---|---|
| Children aged 1-5 years | PPOIT N = 41 | OIT N = 43 | Effect size (Delta) |
| Related Moderate/Severe AEs | | | |
| Number of subjects | 10 (24.4%) | 20 (46.5%) | 22% reduction |
| Number of events | 27 | 43 | 37% reduction |
| Exposure adjusted incidence* | 0.439 | 0.667 | 0.228 reduction |
| Related Moderate/Severe Systemic Reactions | | | |
| Number of subjects | 9 (22%) | 17 (39.5%) | 17.5% reduction |
| Number of events | 16 | 30 | 46.7% reduction |
| Exposure adjusted incidence* | 0.260 | 0.465 | 0.205 reduction |
| GI Disorders (All TEAEs) | | | |
| Number of subjects | 29 (70.7%) | 29 (67.4%) | 3.3% increase |
| Number of events | 156 | 214 | 27% reduction |
| Exposure adjusted incidence* | 2.537 | 3.318 | 0.781 reduction |
| Immune disorders (All TEAEs) | | | |
| Number of subjects | 23 (56.1%) | 28 (65.1%) | 9% reduction |
| Number of events | 97 | 161 | 40% reduction |
| Exposure adjusted incidence* | 1.577 | 2.496 | 0.919 reduction |

Example 4—Effect of PPOIT and OIT on Peanut sIgE Levels

Peanut sIgE is responsible for the presence of allergy to peanut and initiates the cascade of immune changes that lead to symptoms of an allergic reaction. Peanut sIgE provides a biomarker for clinical peanut allergy. The absence of peanut sIgE, or a negative test results for peanut sIgE<0.35 kU/L, is a highly specific marker for absence of IgE mediated allergy to peanut. Conversely, although presence of peanut sIgE on its own does not necessarily result in clinical peanut allergy, the higher the level of peanut sIgE the greater the likelihood of clinical allergy.

In the PPOIT-003 randomised trial described in Example 3, serum levels of peanut sIgE were measured by Immuno-Cap (Phadia) at baseline (T0), end-of-treatment (T1), 8 weeks post-treatment (T2) and 12 months post-treatment (T3). At baseline, the levels of sIgE were similar across the three treatment groups. The results are shown in Table 24, with groups compared in a pairwise fashion using the Wilcoxon Rank Sum.

At T1, peanut sIgE levels were significantly lower in the PPOIT group (6.6 kU/L) compared to the Placebo group (14.5 kU/L) (p=0.0460) and in the OIT group (3.2 kU/L) compared to the Placebo group (14.5 kU/L) (p=0.0057), but not significantly different between PPOIT and OIT groups (6.6 kU/L and 3.2 kU/L respectively, p=0.2484).

At T2, peanut sIgE levels declined further in both the PPOIT group (3.7 kU/L) and the OIT group (2.7 kU/L) and remained significantly lower compared with the Placebo group (18.0 kU/L) (p=0.009 and p=0.001, respectively). There was no significant difference in peanut sIgE levels between the PPOIT and OIT groups (p=0.3700).

The median changes from baseline in peanut sIgE at T1 for the PPOIT group (−5.0 kU/L) and the OIT group (−2.2 kU/L) were both significantly greater than for the Placebo group (0.3 kU/L) (p<0.0001 and p=0.0005, respectively). There was no significant difference in median change from baseline for peanut sIgE at T1 between PPOIT and OIT (p=0.2507). At T2, the median change from baseline in peanut sIgE remained significantly greater in the PPOIT group (−2.7 kU/L) and the OIT group compared to the Placebo group (2.4 kU/L) (both p<0.0001). There was no significant difference in median change from baseline in peanut sIgE between PPOIT and OIT groups (p=0.6331).

These results show that treatment with both PPOIT and OIT modulated the underlying peanut specific allergic immune response. Other studies of Peanut OIT have not shown significant reductions in peanut sIgE after 1-2 years of treatment, with reductions usually only being achieved after 4 or more years of treatment.

TABLE 24

| Serum Peanut sIgE levels before and after treatment in PPOIT-003 trial | | | | |
|---|---|---|---|---|
| | PPOIT N = 79 | OIT N = 83 | Placebo N = 39 | P value PPOIT vs Placebo | P value OIT vs Placebo |
| sIgE T0 Baseline | | | | | |
| n | 76 | 81 | 38 | | |
| Median | 11.1 | 11.0 | 18.0 | 0.942 | 0.438 |
| Min, Max | 0.1, 1115.8 | 0.1, 1861.0 | 0.2, 306.0 | | |
| Q1, Q3 | 1.9, 92.5 | 2.0, 44.0 | 3.8, 59.7 | | |

TABLE 24-continued

| | PPOIT N = 79 | OIT N = 83 | Placebo N = 39 | P value PPOIT vs Placebo | P value OIT vs Placebo |
|---|---|---|---|---|---|
| sIgE T1 Timepoint | | | | | |
| n | 62 | 63 | 32 | 0.003 | <0.0001 |
| Median | 4.5 | 3.5 | 26.0 | | |
| Min, Max | 0.0, 903.3 | 0.0, 867.6 | 0.4, 532.6 | | |
| Q1, Q3 | 1.3, 25.8 | 1.0, 18.8 | 9.1, 77.7 | | |
| sIgE T2 Timepoint | | | | | |
| n | 61 | 61 | 24 | 0.038 | 0.007 |
| Median | 4.3 | 2.9 | 14.8 | | |
| Min, Max | 0.1, 966.1 | 0.1, 664.8 | 0.0, 1259.0 | | |
| Q1, Q3 | 1.1, 23.0 | 0.7, 20.7 | 2.9, 112.8 | | |
| sIgE T3 Timepoint | | | | | |
| n | 65 | 61 | 23 | 0.02 | 0.001 |
| Median | 5.4 | 1.9 | 14.6 | | |
| Min, Max | 0.0, 714.0 | 0.1, 419.0 | 0.0, 596.0 | | |
| Q1, Q3 | 0.8, 21.3 | 0.5, 15.5 | 2.1, 100.0 | | |
| Change from Baseline, End-of-treatment | | | | | |
| n | 61 | 62 | 31 | <0.0001 | <0.0001 |
| Median | −4.6 | −2.2 | 4.1 | | |
| Min, Max | −407.7, 65.6 | −993.4, 82.8 | −58.5, 344.2 | | |
| Q1, Q3 | −64.9, −0.5 | −15.3, 1.6 | −0.5, 28.8 | | |
| Change from Baseline, 8 weeks post-treatment | | | | | |
| n | 59 | 60 | 23 | <0.0001 | <0.0001 |
| Median | −3.5 | −2.1 | 2.2 | | |
| Min, Max | −408.7, 380.7 | −1196.2, 27.6 | −11.1, 1181.7 | | |
| Q1, Q3 | −38.5, −0.1 | −16.1, −0.1 | −0.6, 49.0 | | |
| Change from Baseline, 12 months post-treatment | | | | | |
| n | 62 | 60 | 23 | 0.007 | 0.021 |
| Median | −5.8 | −4.1 | −0.7 | | |
| Min, Max | −407.5, 36.6 | −1442.0, 3.9 | −156.9, 581.4 | | |
| Q1, Q3 | −42.1, −1.0 | −20.9, −1.0 | −10.4, 7.0 | | |

REFERENCES

Wood, JACI; vol. 27(3): 151-159, 2017.
Vickery et al., JACI; 133(2): 468-75, 2014.
PALISADE Study led by Vickery, N Engl. J Med. 2018 Nov. 22; 379(21): 1991-2001.
U.S. Pat. No. 10,265,349.
Tang et al., J Allergy Clin Immunol 135(3): 737-744, 2015.
Colonna et al, Nat Immunol 5:1219-1226, 2004.
Akdis and Akdis, WAO J. 8:17, 2015.
Macginnitie et al., (2017) J Allergy Clin Immunol. 139:873-81.
Anagnostou et al., (2014) Lancet; 383:1297-304.
Schneider et al., (2013) J. Allergy Clin Immunol. 132: 1368-74.

The invention claimed is:

1. A method of treating peanut allergy in a subject allergic or intolerant to peanut allergen, the method comprising administering a peanut allergen to said subject by an oral immunotherapy regimen comprising a dose escalation phase comprising a rush phase and a buildup phase, wherein during the dose escalation phase the peanut allergen is administered in a dose which is increased in increments from an initial dose of peanut allergen equivalent to up to 5 mg peanut protein, to a dose of peanut allergen equivalent to at least 400 mg peanut protein, within 6 to 10 weeks from administration of the initial dose of peanut allergen, wherein in the rush phase, the peanut allergen is administered in a dose which is increased in increments from the initial dose to a dose of the allergen equivalent of at least 12 mg peanut protein within 1 hour to 1 day from administration of the initial dose, and wherein the subject has not received an anti-IgE antibody prior to administration of the initial dose of peanut allergen and does not receive an anti-IgE antibody during the dose escalation phase.

2. The method of claim 1, wherein during said dose escalation phase the dose of peanut allergen is increased in increments to a dose of peanut allergen equivalent to at least 800 mg peanut protein within 8 to 13 weeks from administration of the initial dose.

3. The method of claim 1, wherein the dose escalation phase comprises a series of roughly doubling dose increments from the initial dose of peanut allergen to the dose of at least 400 mg or 800 mg.

4. The method of claim 1, wherein the dose escalation phase is 8 to 24 weeks and a final dose is reached at the end of the dose escalation phase.

5. The method of claim 1, wherein a final dose is reached at the end of the dose escalation phase and said treatment further comprises a maintenance phase following completion of the dose escalation phase, in which the peanut allergen is administered at a set maintenance dose which is ±10% of the final dose reached at the end of the dose escalation phase, wherein (i) the maintenance dose is the peanut allergen equivalent of at least 400 mg peanut protein, and (ii) the duration of the maintenance phase is at least 2 weeks following the completion of the dose escalation phase.

6. The method of claim 1, wherein:

the peanut allergen dose is administered every day during the buildup phase.

7. The method of claim 5, wherein:

the peanut allergen dose is administered every day during the maintenance phase.

8. The method of claim 1, wherein the rush phase is completed in 1 to 12 hours from administration of the initial dose.

9. The method of claim 1, wherein (i) the peanut allergen is, or is present in, or derived from, a peanut protein, (ii) the peanut allergen is provided as peanut protein, as peanut flour or a defatted form thereof, (iii) the peanut allergen is provided as one or more isolated peanut allergens selected from the group consisting of Ara h1, Ara h2, Ara h3, Ara h5, Ara h6, Ara h7, Ara h8, Ara h9, Ara h10, Ara h11, Ara h12, Ara h13, Ara h14, Ara h15, Ara h16 and Ara h17 or a modified form of any one or more thereof, or (iv) the peanut allergen is provided as Ara h2 or a modified form thereof.

10. The method of claim 1, wherein the peanut allergen is administered in or on apple sauce, pudding, yoghurt or chocolate.

11. The method of claim 1, wherein the subject is:

(i) an adult;

(ii) less than 18 years old;

(iii) less than 10 years old;

(iv) less than 5 or 6 years old;

(v) from 1 month to 12 years old;

(vi) from 6 to 12 years old; or (vii) from 1 to 5 years old.

12. The method of claim 1, wherein a reduced duration of dose escalation phase compared to oral immunotherapy regimens using a longer dose escalation phase to reach a same maintenance dose improves the likelihood or odds of the subject achieving sustained unresponsiveness.

13. The method of claim 1, wherein during said dose escalation phase the dose of peanut allergen is increased in increments to a dose of peanut allergen equivalent to at least 2 g peanut protein within 16 to 24 weeks from administration of the initial dose.

14. The method of claim 1, wherein a final dose is reached at the end of the dose escalation phase and said treatment further comprises a maintenance phase following completion of the dose escalation phase, in which the peanut allergen is administered at a set maintenance dose which is ±10% of the final dose reached at the end of the dose escalation phase, wherein:

(i) the maintenance dose is the peanut allergen equivalent of at least 800 mg peanut protein, and (ii) the duration of the maintenance phase is at least 26 weeks following the completion of the dose escalation phase.

15. The method of claim 1, wherein a final dose is reached at the end of the dose escalation phase and said treatment further comprises a maintenance phase following completion of the dose escalation phase, in which the peanut allergen is administered at a set maintenance dose which is ±10% of the final dose reached at the end of the dose escalation phase, wherein:

(i) the maintenance dose is the peanut allergen equivalent of at least 2000 mg peanut protein, and (ii) the duration of the maintenance phase is at least 60 weeks following the completion of the dose escalation phase.

16. The method of claim 1, wherein the peanut allergen dose is administered every 2 or 3 days during the buildup phase.

17. The method of claim 5, wherein the peanut allergen dose is administered every 2 or 3 days during the maintenance phase.

18. The method of claim 12, wherein using a dose escalation phase of 8 to 12 weeks to reach a maintenance dose of 400 mg or more improves the likelihood or odds of the subject achieving sustained unresponsiveness compared to oral immunotherapy regimens using a longer dose escalation phase to reach the same maintenance dose.

19. The method of claim 12, wherein using a dose escalation phase of 8 to 14 weeks to reach a maintenance dose of 800 mg or more improves the likelihood or odds of the subject achieving sustained unresponsiveness compared to oral immunotherapy regimens using a longer dose escalation phase to reach the same maintenance dose.

20. The method of claim 12, wherein using a dose escalation phase of 16 to 24 weeks to reach a maintenance dose of 2000 mg or more improves the likelihood or odds of the subject achieving sustained unresponsiveness compared to oral immunotherapy regimens using a longer dose escalation phase to reach the same maintenance dose.

* * * * *